(12) United States Patent
Klueh et al.

(10) Patent No.: US 10,405,961 B2
(45) Date of Patent: *Sep. 10, 2019

(54) COATED SURGICAL MESH, AND CORRESPONDING SYSTEMS AND METHODS

(71) Applicant: Cell and Molecular Tissue Engineering, LLC, Avon, CT (US)

(72) Inventors: Ulrike W. Klueh, Avon, CT (US); Donald L. Kreutzer, Avon, CT (US)

(73) Assignee: Cell and Molecular Tissue Engineering, LLC, Avon, CT (US)

( * ) Notice: Subject to any disclaimer, the term of this patent is extended or adjusted under 35 U.S.C. 154(b) by 31 days.

This patent is subject to a terminal disclaimer.

(21) Appl. No.: 15/255,484

(22) Filed: Sep. 2, 2016

(65) Prior Publication Data

US 2017/0143876 A1    May 25, 2017

Related U.S. Application Data

(63) Continuation-in-part of application No. 13/828,854, filed on Mar. 14, 2013, now abandoned, and a continuation-in-part of application No. 14/485,313, filed on Sep. 12, 2014, now Pat. No. 9,717,583, and a continuation-in-part of application No. PCT/US2015/049718, filed on Sep. 11, 2015.

(51) Int. Cl.
| | | |
|---|---|---|
| A61B 5/00 | (2006.01) | |
| A61F 2/00 | (2006.01) | |
| A61L 31/10 | (2006.01) | |
| A61L 31/16 | (2006.01) | |
| C08L 89/00 | (2006.01) | |
| A61M 5/158 | (2006.01) | |
| A61B 5/145 | (2006.01) | |

(52) U.S. Cl.
CPC ............ *A61F 2/0063* (2013.01); *A61L 31/10* (2013.01); *A61L 31/16* (2013.01); *A61M 5/158* (2013.01); *A61B 5/14532* (2013.01); *A61B 5/686* (2013.01); *A61B 2562/18* (2013.01); *A61F 2240/001* (2013.01); *A61F 2250/0067* (2013.01); *A61L 2300/414* (2013.01); *A61L 2300/64* (2013.01); *A61M 2005/1581* (2013.01); *A61M 2205/0205* (2013.01)

(58) Field of Classification Search
None
See application file for complete search history.

(56) References Cited

U.S. PATENT DOCUMENTS

| | | |
|---|---|---|
| 4,685,900 A | 8/1987 | Honard et al. |
| 4,715,858 A | 12/1987 | Lindstrom |
| 4,829,000 A | 5/1989 | Kleinman et al. |
| 4,902,295 A | 2/1990 | Walthall et al. |
| 4,997,443 A | 3/1991 | Walthall et al. |
| 5,131,907 A | 7/1992 | Williams et al. |
| 5,165,407 A | 11/1992 | Wilson et al. |
| 5,265,608 A | 11/1993 | Lee et al. |
| 5,284,140 A | 2/1994 | Allen et al. |
| 5,411,527 A | 5/1995 | Alt |
| 5,490,962 A | 2/1996 | Cima et al. |
| 5,609,629 A | 3/1997 | Fearnot et al. |
| 5,653,755 A | 8/1997 | Ledergerber |
| 5,711,861 A | 1/1998 | Ward et al. |
| 5,798,113 A | 8/1998 | Dionne et al. |
| 5,814,091 A | 9/1998 | Dahlberg et al. |
| 5,834,001 A | 11/1998 | Dionne et al. |
| 5,893,888 A | 4/1999 | Bell |
| 5,932,459 A | 8/1999 | Sittinger et al. |
| 5,936,061 A | 8/1999 | Andersson et al. |
| 6,139,574 A | 10/2000 | Vacanti et al. |
| 6,143,501 A | 11/2000 | Sittinger et al. |
| 6,211,144 B1 | 4/2001 | Havelund |
| 6,212,416 B1 | 4/2001 | Ward et al. |
| 6,264,992 B1 | 7/2001 | Voytik-Harbin et al. |
| 6,284,284 B1 | 9/2001 | Naughton |
| 6,303,765 B1 | 10/2001 | Bandman et al. |
| 6,328,762 B1 | 12/2001 | Anderson et al. |
| 6,466,810 B1 | 10/2002 | Ward et al. |
| 6,489,292 B1 | 12/2002 | Havelund et al. |
| 6,497,729 B1 | 12/2002 | Moussey et al. |
| 6,572,878 B1 | 6/2003 | Blaine |
| 6,589,224 B2 | 7/2003 | Winchester |

(Continued)

FOREIGN PATENT DOCUMENTS

| | | |
|---|---|---|
| WO | 1997015655 | 5/1997 |
| WO | 1997019344 | 5/1997 |

(Continued)

OTHER PUBLICATIONS

Klueh et al., Basement Membrane-Based GlucoseSensor Coatings Enhance Continuous Glucose Monitoring in Vivo, Journal of Diabetes Science and Technology 2015, vol. 9(5) 957-965.*

Apaja-Sarkkinen et al., "Immunohistochemical study of basement membrane proteins and type III procollagen in myelofibrosis.," Br J Haematol., Jul. 1986, 63(3):571-530, Abstract.

Kalebic et al., "Basement membrane collagen: degradation by migrating endothelial cells.," Science., Jul. 15, 1983, 221(4607):281-3, Abstract.

(Continued)

*Primary Examiner* — Louise W Humphrey
*Assistant Examiner* — Srikanth Patury
(74) *Attorney, Agent, or Firm* — Alix, Yale & Ristas, LLP

(57) ABSTRACT

Disclosed herein are medical products, including a surgical mesh, with a layer of dehydrated modified basement membrane preparation formed thereon. The basement membrane has been modified before dehydration of remove low molecular weight components. In some embodiments, the basement membrane is crosslinked. Methods of making and using the products also are disclosed.

18 Claims, 55 Drawing Sheets

(56) References Cited

U.S. PATENT DOCUMENTS

| | | | |
|---|---|---|---|
| 6,596,296 B1 | 7/2003 | Nelson et al. |
| 6,642,015 B2 | 11/2003 | Vachon et al. |
| 6,673,596 B1 | 1/2004 | Sayler et al. |
| 6,716,246 B1 | 4/2004 | Gonzalez |
| 6,824,561 B2 | 11/2004 | Soykan et al. |
| 6,858,222 B2 | 2/2005 | Nelson et al. |
| 6,884,428 B2 | 4/2005 | Binette et al. |
| 7,033,603 B2 | 4/2006 | Nelson et al. |
| 7,048,856 B2 | 5/2006 | Fissell, IV et al. |
| 7,137,968 B1 | 11/2006 | Burrell et al. |
| 7,153,265 B2 | 12/2006 | Vachon |
| 7,163,920 B2 | 1/2007 | Dhanaraj et al. |
| 7,303,814 B2 | 12/2007 | Lamberti et al. |
| 7,396,537 B1 | 7/2008 | Krupnick et al. |
| 7,433,727 B2 | 10/2008 | Ward et al. |
| 7,514,095 B2 | 4/2009 | Nelson et al. |
| 7,799,767 B2 | 9/2010 | Lamberti et al. |
| 8,053,423 B2 | 11/2011 | Lamberti et al. |
| 8,062,654 B2 | 11/2011 | Nelson et al. |
| 2001/0000802 A1 | 5/2001 | Soykan et al. |
| 2002/0110585 A1 | 8/2002 | Godbey et al. |
| 2003/0009131 A1 | 1/2003 | Van Antwerp et al. |
| 2003/0087311 A1 | 5/2003 | Wolf |
| 2003/0099682 A1 | 5/2003 | Moussy et al. |
| 2003/0138950 A1 | 7/2003 | McAllister et al. |
| 2003/0139333 A1 | 7/2003 | Pawliuk et al. |
| 2004/0006070 A1 | 1/2004 | Hassenbusch et al. |
| 2004/0126881 A1 | 7/2004 | Ronfard |
| 2004/0234510 A1* | 11/2004 | Mochitate ............... A61L 27/20 424/93.7 |
| 2004/0234525 A1 | 11/2004 | Wayner |
| 2005/0019419 A1* | 1/2005 | Badylak ............... C12N 5/0068 424/553 |
| 2005/0031689 A1 | 2/2005 | Shults et al. |
| 2005/0098500 A1 | 5/2005 | Collins et al. |
| 2005/0175705 A1* | 8/2005 | Wu ...................... C12N 5/0068 424/488 |
| 2005/0267441 A1 | 12/2005 | Douglas |
| 2006/0068208 A1 | 3/2006 | Tapsak et al. |
| 2006/0198871 A1 | 9/2006 | Wong |
| 2006/0201996 A1* | 9/2006 | Hodde ................... A61K 35/24 228/101 |
| 2006/0234369 A1 | 10/2006 | Sih |
| 2006/0252981 A1 | 11/2006 | Matsuda et al. |
| 2007/0077265 A1 | 4/2007 | Klueh et al. |
| 2007/0077272 A1 | 4/2007 | Li et al. |
| 2007/0084144 A1 | 4/2007 | Labrecque et al. |
| 2007/0224137 A1 | 9/2007 | Detmar et al. |
| 2008/0096799 A1 | 4/2008 | Nestor |
| 2008/0206440 A1 | 8/2008 | Cottone |
| 2008/0267958 A1 | 10/2008 | Jalkanen et al. |
| 2009/0004239 A1 | 1/2009 | Ladet et al. |
| 2009/0099436 A1 | 4/2009 | Brister et al. |
| 2009/0270978 A1 | 10/2009 | Virkler et al. |
| 2009/0275645 A1 | 11/2009 | Laguens et al. |
| 2009/0311240 A1 | 12/2009 | Mittermayr et al. |
| 2009/0317469 A1 | 12/2009 | Johnson et al. |
| 2010/0185219 A1* | 7/2010 | Gertzman ............. A61L 31/005 606/151 |
| 2010/0203023 A1* | 8/2010 | Johnson ............. A61L 27/3604 424/93.7 |
| 2011/0020435 A1 | 1/2011 | Maggio |
| 2011/0139617 A1 | 6/2011 | Franser et al. |
| 2011/0152820 A1 | 6/2011 | Chattaraj et al. |
| 2011/0166673 A1 | 7/2011 | Patel et al. |
| 2011/0168170 A1 | 7/2011 | Patton et al. |
| 2011/0293562 A1 | 12/2011 | Prieto Valtuena et al. |
| 2012/0076868 A1 | 3/2012 | Lamberti et al. |
| 2012/0093759 A1 | 4/2012 | Vachon |
| 2012/0149758 A1 | 6/2012 | Al Mahmood |
| 2012/0196800 A1 | 8/2012 | Naver et al. |
| 2012/0252724 A1 | 10/2012 | Schoettle et al. |
| 2012/0277148 A1 | 11/2012 | Weiss |
| 2012/0295846 A1 | 11/2012 | Hagendorf et al. |
| 2012/0316107 A1 | 12/2012 | Weiss |
| 2013/0109039 A1 | 5/2013 | Kristensen et al. |
| 2014/0073704 A1 | 3/2014 | Ju et al. |

FOREIGN PATENT DOCUMENTS

| | | |
|---|---|---|
| WO | 1999048541 | 9/1999 |
| WO | 2000078929 | 12/2000 |
| WO | 2002086107 | 10/2002 |
| WO | 2003072155 | 9/2003 |
| WO | 2003072157 | 9/2003 |
| WO | 2012018680 | 2/2012 |
| WO | 2013023051 | 2/2013 |

OTHER PUBLICATIONS

Glaser et al., "Degradation of basement membrane components by vascular endothelial cells: role in neovascularization.," Ciba Found Symp., 1983, 100:150-162, Abstract.

Bartone et al., The reaction of the urinary tract to catgut and reconstituted collegan sutures, The Journal of Urology, vol. 101, Mar. 1969, pp. 411-416.

Ratner et al., "Biomaterials Science: an Introduction to materials in Medicine,"10 pp (including cover, copyright page, and 445-446 and 60-64).

International Search Report and Written Opinion for PCT/US2015/049718, dated Feb. 1, 2016.

International Preliminary Report on Patentability for PCT/US2014/025738, dated Sep. 15, 2015.

International Search Report and Written Opinion for PCT/US2014/025738, dated Aug. 22, 2014.

"Sensors for Medicine and Science Changes Company Name to Senseonics," Senseonics, Oct. 16, 2012, 2 pages.

"First Implantable Continuous Sensor to Achieve High Accuracy Performance in People with Diabetes," Senseonics, Sep. 12, 2011, 2 pages.

Mercandetti et al., Implants, Soft Tissue, AlloDerm, Medscape Reference, 2011.

Supplementary EP Search Report for Application No. 04816945.2 dated Sep. 4, 2009.

Cao et al., The topographical effect of electrospun nanofibrous scaffolds on the in vivo . . . , 2009 Wiley Periodicals, Inc. J. Biomed. Mater. Res., pp. 1151-1159.

Barbosa et al., Evaluation of the effect of the degree of acetylation on the inflammatory response to 3D porous chitosan scaffolds, 2009 Wiley Periodicals, Inc., pp. 20-28.

Yoshioka et al., Imporvement of Bicompatibility of Chitosan Fiber Modified by Ca-Phosphate Deposition . . . , Materials Transactions, vol. 50, No. 6 (2009), pp. 1269-1272.

S.F. Badylak et al., Extracellular martix as a biological scaffold martial: Structure and function, Acta Biomaterialia 5 (2009), pp. 1-13.

Gellynck et al., Biocompatibility and biodegradability of spider egg sac silk, J Mater Sci: Mater Med (2008) 19:2963-2970.

Wang et al., "Electrochemical Sensors for Clinical Analysis," Sensors 2008, 8, pp. 2043-2081.

Jiang et al., Phagocyte responses to degradable polymers, 207 Wiley Periodicals, Inc. J Biomed Mater Res 82A: 494-497, 2007.

Ceonzo et al., Polygycolic acid induced inflammation: Role of hydrosis and resulting complement activation1, NIH Tissue Eng. Feb. 2006; 12(2): 301-308.

International Search Report and Written Opinion for PCT/US2004/037302, dated Nov. 9, 2005.

Butler et al., Reduction of Adhesions with Composite Alloderm/Polypropylene Mesh Implants for Abdominal Wall Reconstruction, Plastic and Reconstructive Surgery, vol. 114, No. 2, pp. 464-473, 2004.

Jimenez, M.D. et al., "Tissue and cellular approaches to wound repair," The American Journal of Surgery 187, (Suppl. to May 2004), pp. 56S-64S.

Ward et al., "The Effect of Local Subcutaneous Delivery of Vascular Endothelial Growth Factor . . . ," Diabetes Technology & Therepeutics, vol. 6, No. 2, 2004, pp. 137-145.

(56) References Cited

OTHER PUBLICATIONS

Klueh et al., "Use of vascular endothelial cell growth factor gene . . . ," Journal of Biomedical Materials Research, Part A, vol. 67A, Issue 4, pp. 1072-1086, Dec. 15, 2003.
Abstract, "Use of vascular endothelial cell growth factor gene transfer to enhance . . . ," 2003 Society for Biomaterials 29th Annual Meeting Transactions, Apr. 30, 2003.
Feldman et al., "A Continuous Glucose Sensor Based on Wired EnzymeTM Technology—Results from a . . . ,"Diabetes Technology & Therepeutics, vol. 5, Nov. 5, 2003, pp. 769-779.
Altman et al., Silk-based biomaterials, Biomaterials 24 (2003) 401-416.
Matrigel, BD Biosciences Product sheet 2002.
Vandevord et al., Evaluation of the biocompatibility of a chitosan scaffold in mice, 2001 John Wiley & Sons, Inc. J. Biomed. Mater. Res. 59: 585-590, 2002.
Gerritsen et al., Influence of inflammatory cells and serum on the performance of implantable glucose sensors, Journal of Biomedical Materials Research, vol. 54, 69-75 (2001).
Ueno et al., Topical formulations and wound healing applications of chitosan, Advanced Drug Delivery Reviews 52 (2001) 105-115.
Ueno et al., Chitosan accelerates the production of osteopontin from polymorphonuclear leukocytes, Biomaterials 22 (2001) 1667-1673.
Wisniewski et al., Methods for reducing biosensor membrane biofouling, Colloids and Surfaces B: Biointerfaces 18 (2000), Relevant portions pp. 197-198, 204-205, 212-213.
Wisniewski et al., "Characterization of implantable biosensor membrane biofouling, "Fresenius J Anal Chem (2000) 366:611-621.
Hubbell, Bioactive biomaterials, Current Opinion in Biotechnology 1999, 10:123-129, Relevant portion p. 125.
Magnusson, Fibronectin: Structure, Assembly and Cardiovascular Implications, Arteriosclerosis, Thrombosis, and Vascular Biology, 1998, 18: 1363-1370.
Ibim et al., Poly(anhydride-co-imides): in vivo biocompatibility in a rat model, Biomaterials 19 (1998) 941-951.
Eriksson et al., "Removal of toxic preservatives in pharmaceutical preparations of insulin by the use of . . . ," Biotechnology Techniques, vol. 12, No. 4, Apr. 1998, pp. 329-334.
Oh et al., "VEGF and VEGF-C: Specific Induction of Angiogensis and Lymphangiogenesis in the Differentiated Avian Chorioallan . . . ," Development Biology, 188, pp. 96-109 (1997).
Maragoudakis et al., "Basement membrane biosynthesis as a target for developing inhibitors of angiogenesis with anti-tumor . . . " Kidney Int., Jan. 1993, 43(1):147-150, Abstract.
Grant et al., "Interaction of endothelial cells with a laminin A chain peptide (SIKVAV) in vitro and induction . . . ," J Cell Physiol., Dec. 1992, 153(3):614-625, Abstract.
Kibbey et al., "Role of the SIKVAV site of laminin in promotion of angiogenesis and tumor growth: an in vivo . . . ," J Natl Cancer Inst., Nov. 1992, 84(21).1633-1638, Abstract.
Passaniti et al., "A simple, quantitative method for assessing angiogenesis and antiangiogenic agents using reconstituted . . . ," Lab Invest., Oct. 1992, 67(4):519-528, Abstract.
Kaneko, "[Relationship between endothelial cells and extracellular matrix: investigation using the model of . . . ," Nippon Geka Hokan., Mar. 1, 1992, 61(2):134-149, Abstract.
Jerdan et al., "Extracellular matrix of newly forming vessels-an immunohistochemical study," Microvasc. Res., Nov. 1991, 42(3):255-265, Abstract.
Schultz et al., "Neovascular growth factors.," Eye (Lond)., 1991, 5 (Pt 2):170-180, Abstract.
Couchman et al., Fibronectin-Cell Interactions, Journal Investigative Dermatology, 94:7S-14S, 1990.
Nicosia et al., "Modulation of microvascular growth and morphogenesis by reconstituted basement membrane in gel . . . ," In Vitro Cell Dev Biol., Feb. 1990, 26(2):119-128, Abstract.
Brasken et al., "Fibronectin, laminin, and collagen types I, III, IV and V in the healing rat colon anastomosis," Ann Chir Gynaecol., 1990, 79(2):65-71.
Mori et al.,"Capillary growth from reversed rat aortic segments cultured in collagen gel.," Acta Pathol Jpn., Dec. 1998, 38(12):1503-1512, Abstract.
Maragoudakis et al., "Inhibition of basement membrane biosynthesis prevents angiogenesis.," J Pharmacol Exp Ther., Feb. 1988, 244(2):729-733, Abstract.
Folkman et al., "A heparin-binding angiogenic protein-basic fibroblast growth factor-is stored within basement membrane.," Am J Pathol., Feb. 1988, 130(2):393-400, Abstract.
Maragoudakis et al., "Rate of basement membrane biosynthesis as an index to angiogenesis.," Tissue Cell., 1988, 20(4):531-539, Abstract.
Form et al., "Endothelial cell proliferation during angiogenesis. In vitro modulation by basement membrane components.," Lab Invest., Nov. 1986, 55(5):521-530, Abstract.

\* cited by examiner

FIGURE 6
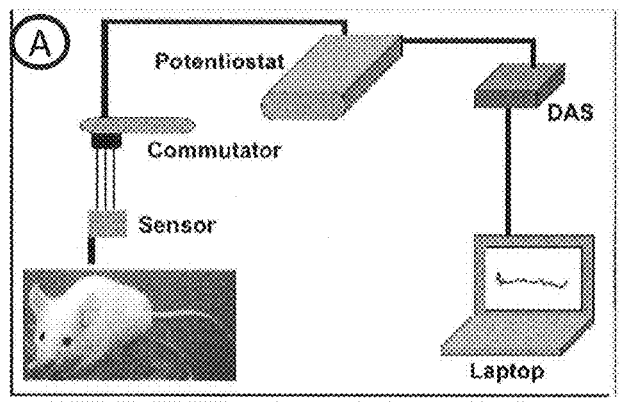
Fig. 6A
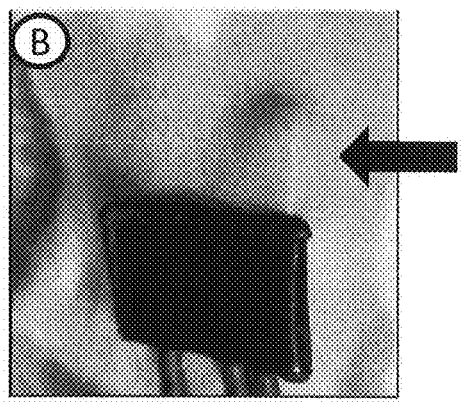
Fig. 6B
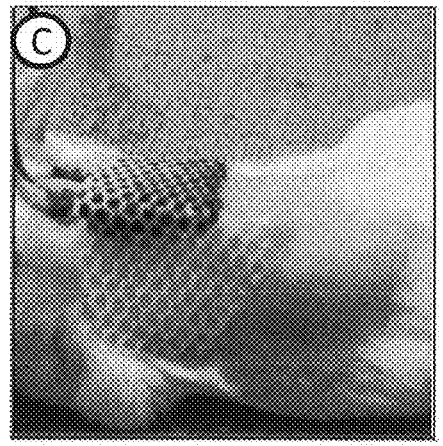
Fig. 6C
Fig. 6D 28 day Glucose Sensor Function in untreated normal C57B/6 mice

FIGURE 7E-7H
28 day Glucose Sensor Function in saline injected normal C57B/6 mice
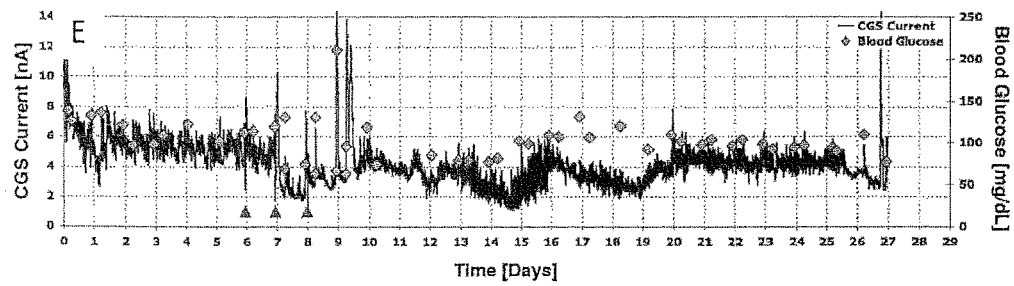
Fig. 7E
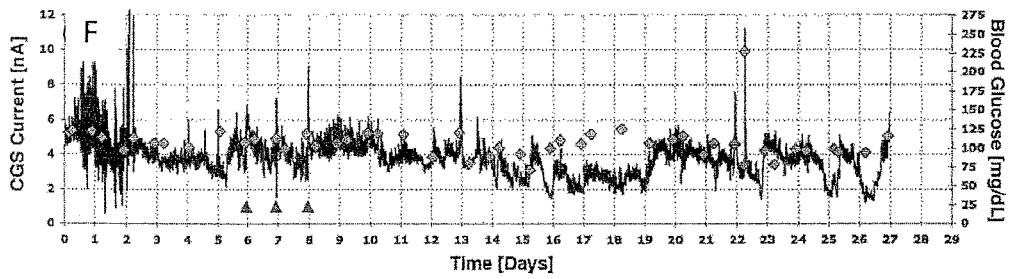
Fig. 7F
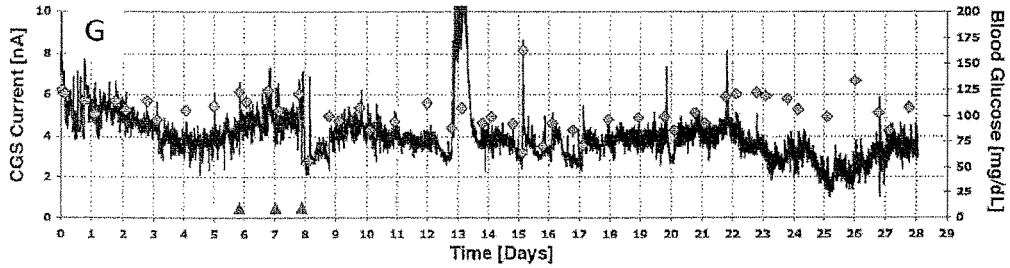
Fig. 7G
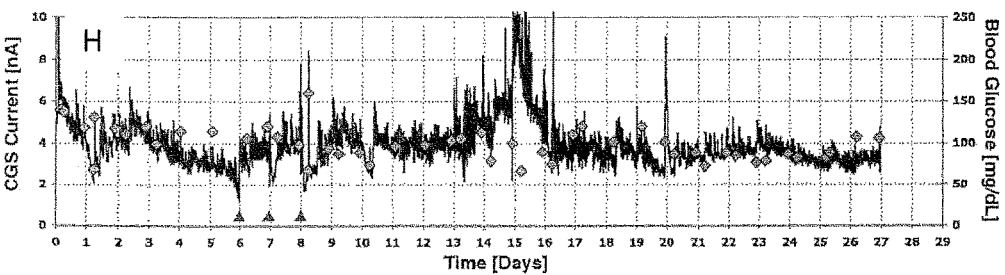
Fig. 7H

FIGURE 7I-7L
28 day Glucose Sensor Function in Adv-LacZ adenovirus injected C57B/6
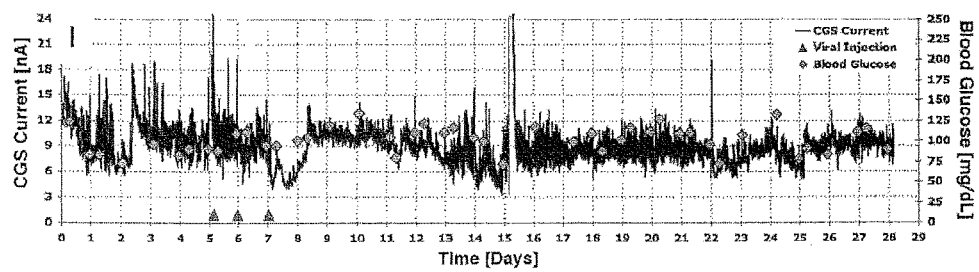
Fig. 7I
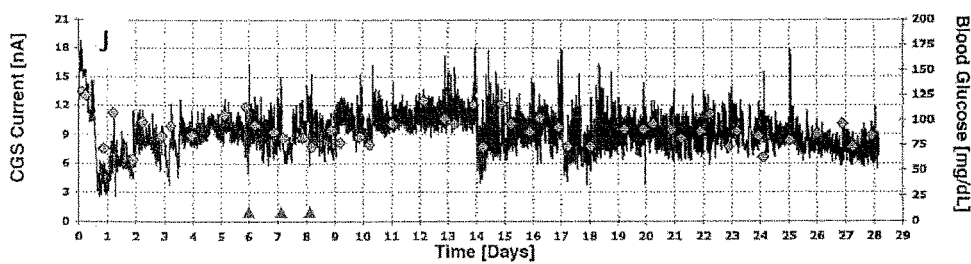
Fig. 7J
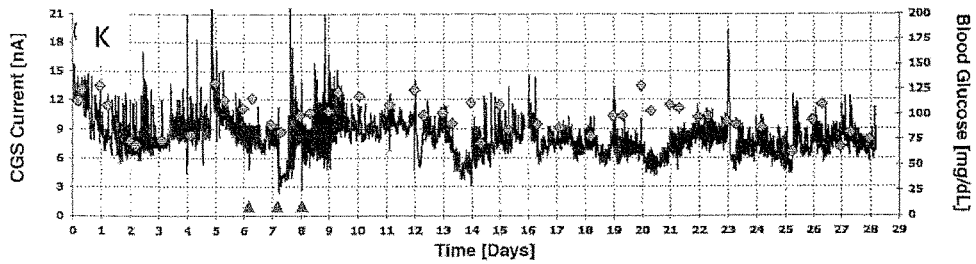
Fig. 7K
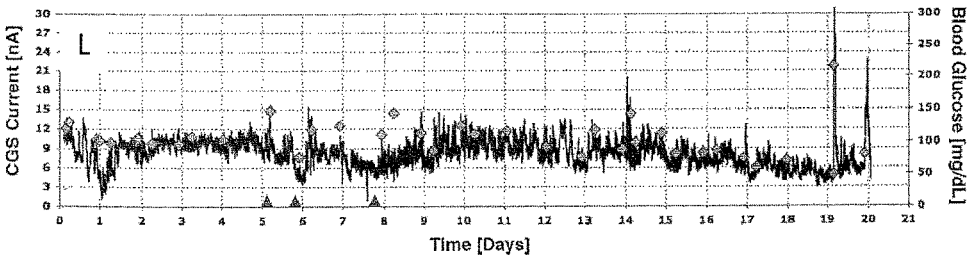
Fig. 7L

FIGURE 7M-7P
28 day Glucose Sensor Function in Adv-VEGFa adenovirus injected C57B/6 mice
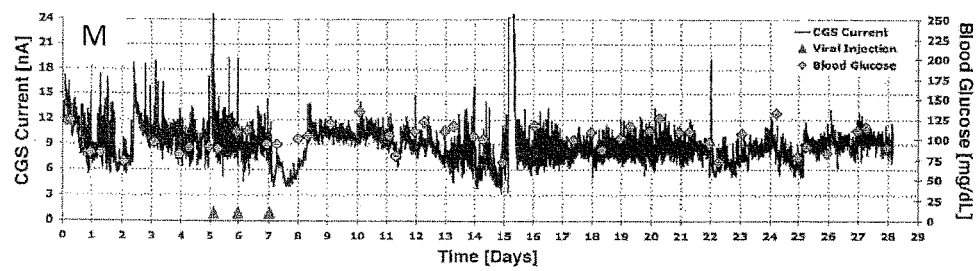
Fig. 7M
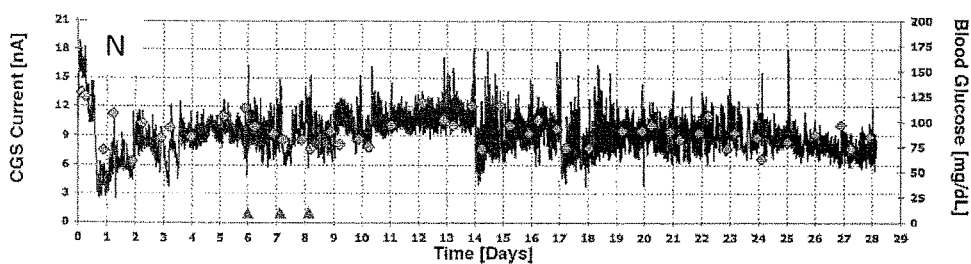
Fig. 7N
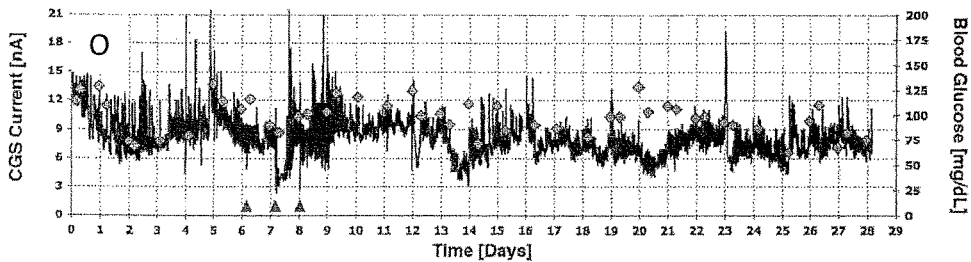
Fig. 7O
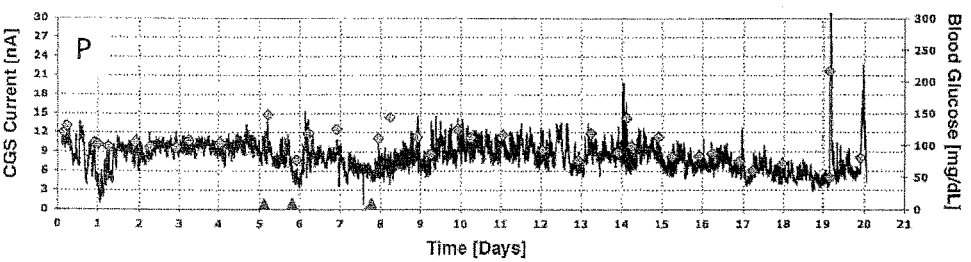
Fig. 7P Blood Vessel MARD trend analysis at Sensor Implantation Sites from Normal, Saline Injected, Adv-LacZ Injected, and Adv-VEGFa Injected Blood Vessel Density Boxplot at Sensor Implantation Sites from Normal, Saline Injected, Adv-LacZ Injected, and Adv-VEGFa Injected.

FIGURE 10

| Total mean MARD data | No Inj.: C57BL/6 Average Mean MARD = 23.50 +/- 9.83% (n=26) | Saline: C57BL/6 Average Mean MARD = 24.91 +/- 15.74% (n=16) | Adv-LacZ: C57BL/6 Average Mean MARD = 31.49 +/- 14.50% (n=23) | Adv-VEGFa: C57BL/6 Average Mean MARD = 17.44 +/- 5.72% (n=15) |
|---|---|---|---|---|
| No Inj.: C57BL/6 Average Mean MARD = 23.50 +/- 9.83% (n=26) | | p = 0.3343 | p = 0.0135 | p = 0.0178 |
| Saline: C57BL/6 Average Mean MARD = 24.91 +/- 15.74% (n=16) | | | p = 0.0986 | p = 0.0378 |
| Adv-LacZ: C57BL/6 Average Mean MARD = 31.49 +/- 14.50% (n=23) | | | | p = 0.0001 |
| Adv-VEGFa: C57BL/6 Average Mean MARD = 17.44 +/- 5.72% (n=15) | | | | |

FIGURE 13A

Relative contribution of percent area as *blood* vessel to improvement in average Mean Absolute

| Histology of Back Tissue | Total mean MARD data | Week 1 mean MARD data | Cumulative 2 weeks mean MARD data | Cumulative 3 weeks mean MARD data | Cumulative 4 weeks mean MARD data |
|---|---|---|---|---|---|
| MARD/% area bv (B) | -7.661 | -2.537 | -5.539 | -7.922 | -9.120 |
| Standard Error (SE) | 2.754 | 3.221 | 3.282 | 3.018 | 2.771 |
| Significance (p) | p = 0.013 | p = 0.442 | p = 0.111 | p = 0.018 | p = 0.005 |
| Correlation ($R^2$) | .313 | .035 | .151 | .301 | .404 |

FIGURE 13B

Statistical comparison of lymphatic and blood vessel counts per square millimeter.

| Histology of Back Tissue | |
|---|---|
| Ratio #/mm² LV/BV | 1.063 |
| Standard Error | .250 |
| Significance | 0.0001 |
| $R^2$ | .328 |
| Sample Size | 39 |

FIGURE 13C

Relative contribution of percent area as *lymph* vessel to improvement in average Mean Absolute Relative Difference (MARD) values for all data combined (total) and cumulative one, two, three, and four weeks

| Histology of Back Tissue | Total mean MARD data | Week 1 mean MARD data | Cumulative 2 weeks mean MARD data | Cumulative 3 weeks mean MARD data | Cumulative 4 weeks mean MARD data |
|---|---|---|---|---|---|
| MARD/% area lv (B) | -3.674 | 0.791 | -2.388 | -3.435 | -4.291 |
| Standard Error (SE) | 1.715 | 1.949 | 1.903 | 1.845 | 1.704 |
| Significance (p) | 0.0461 | 0.6896 | 0.2264 | 0.0801 | 0.0237 |
| Correlation ($R^2$) | .203 | .009 | .085 | .169 | .297 |

FIGURE 13D

Relative contribution of percent area as *blood or lymph* vessel to improvement in average Mean Absolute Relative Difference (MARD) values for all data combined (total) and cumulative one, two, three, and four weeks

| Histology of Back Tissue | Total mean MARD data | Week 1 mean MARD data | Cumulative 2 weeks mean MARD data | Cumulative 3 weeks mean MARD data | Cumulative 4 weeks mean MARD data |
|---|---|---|---|---|---|
| MARD/% area bv (B) | -6.360 | -7.090 | -5.522 | -7.837 | -7.134 |
| Standard Error (SE) | 4.156 | 4.636 | 5.368 | 4.936 | 4.743 |
| MARD/% area lv (B) | -1.047 | 3.665 | -.013 | -.063 | -1.279 |
| Standard Error (SE) | 2.455 | 2.739 | 3.084 | 2.836 | 2.586 |
| Significance (p) | 0.0455 | 0.3213 | 0.2926 | 0.0681 | 0.0297 |
| Correlation ($R^2$) | .320 | .132 | .151 | .301 | .395 |

FIGURE 16
Fig. 16A
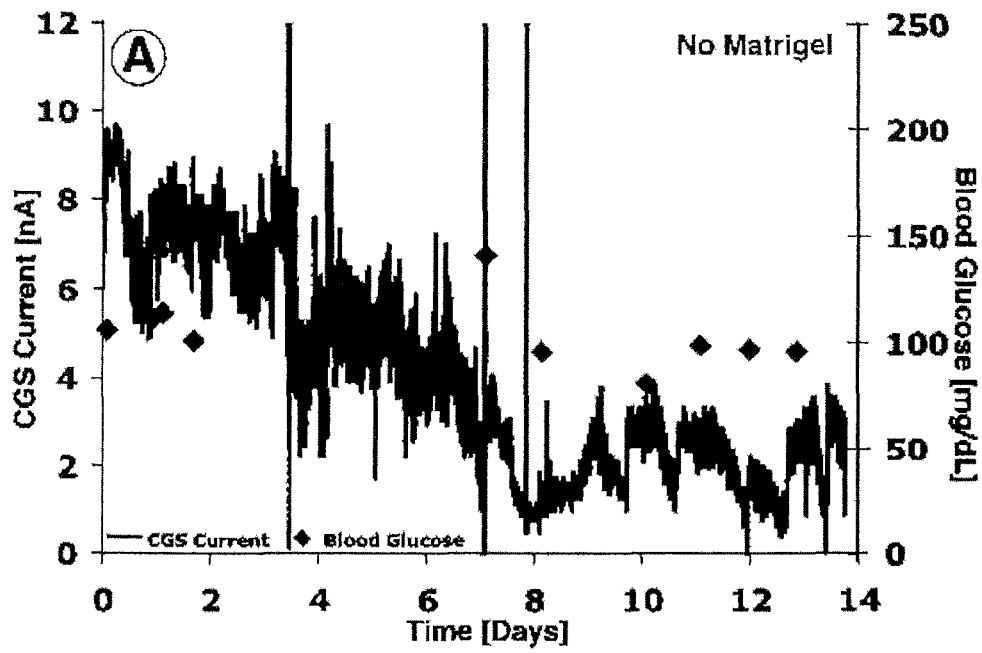
Fig. 16B
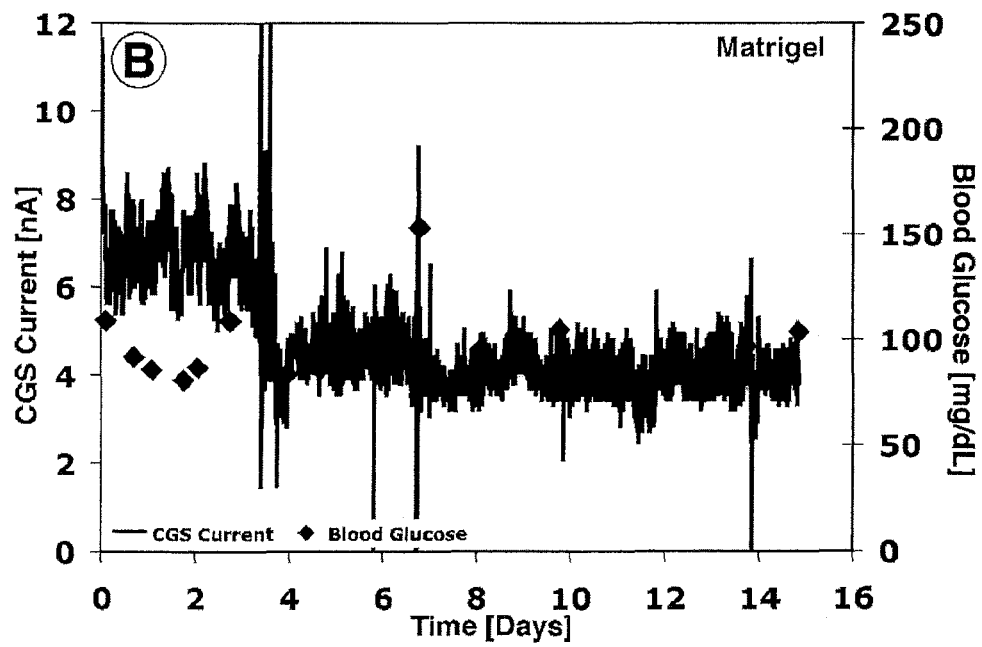

FIGURE 18
18A Functionality of Air-Dried Adenovector-Matrigel Coatings
GFP-Adeno + Matrigel > Coat Sensor > "Dry" > Cells
BF
F
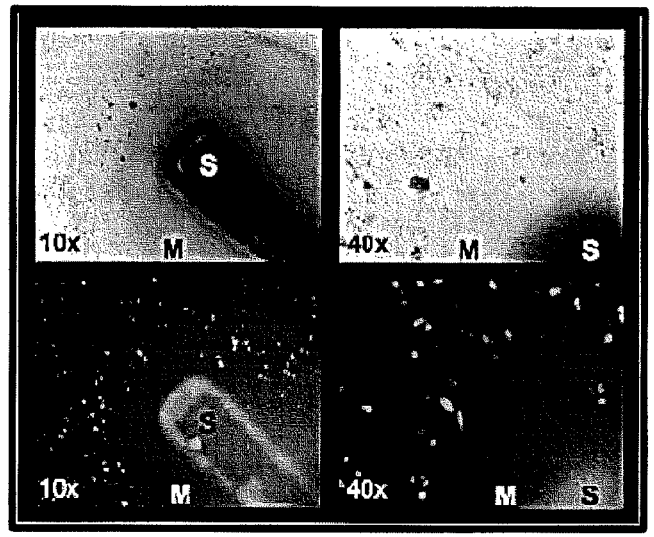
S denotes sensor; M denotes Matrigel
Fig. 18A
18B Functionality of Air-Dried Adenovector-Collagen Coatings
GFP-Adeno + Collagen > Coat Sensor > "Dry" > Cells
BF
F
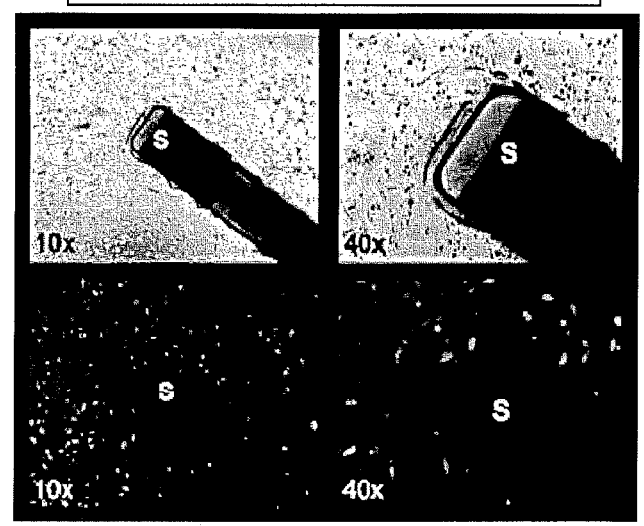
S denotes sensor
Fig. 18B

FIGURE 19
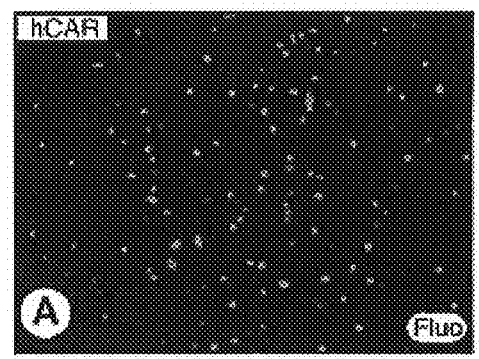
Fig. 19A
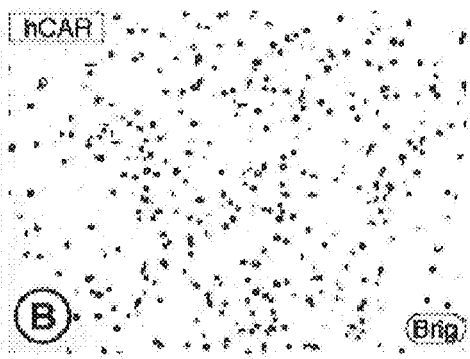
Fig. 19B
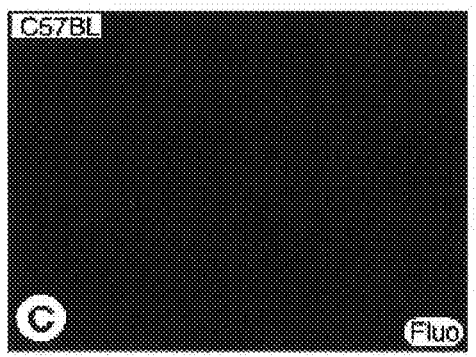
Fig. 19C
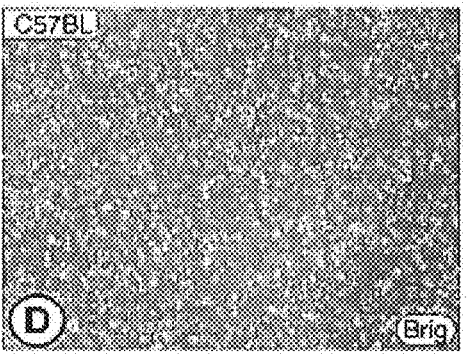
Fig. 19D

FIGURE 20
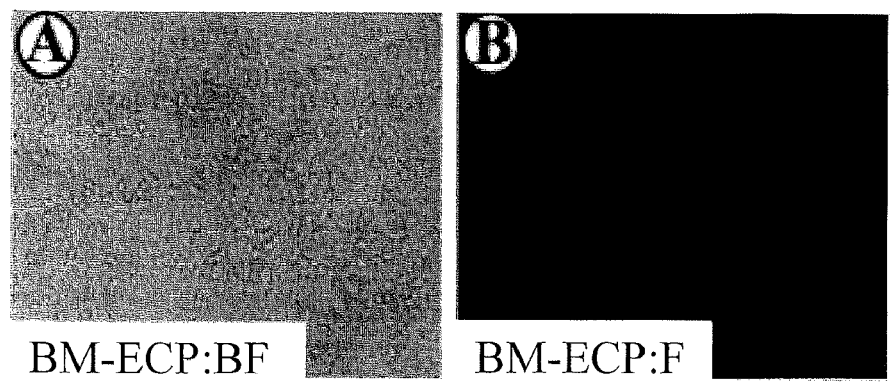
BM-ECP:BF
Fig. 20A
BM-ECP:F
Fig. 20B
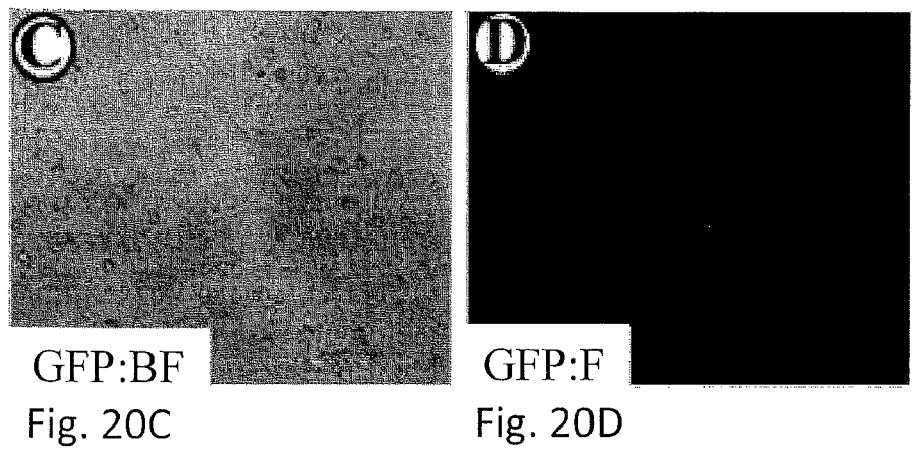
GFP:BF
Fig. 20C
GFP:F
Fig. 20D
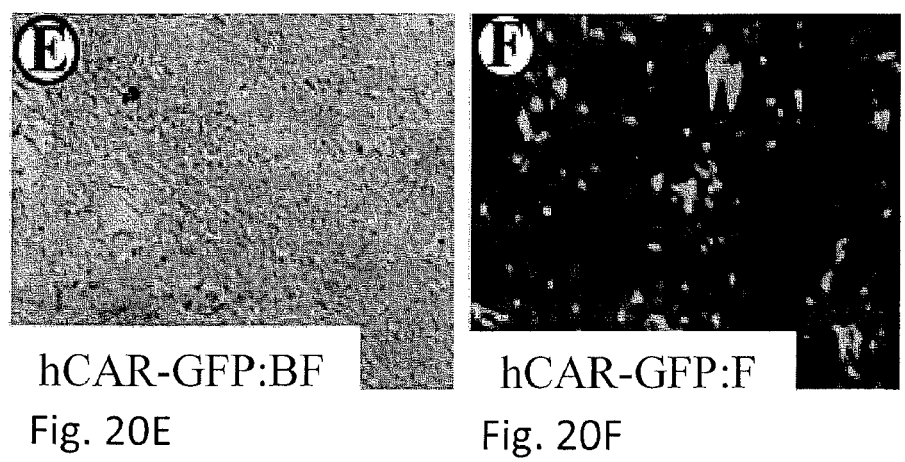
hCAR-GFP:BF
Fig. 20E
hCAR-GFP:F
Fig. 20F

*In Vitro* expression of hHGF in BM-ECP cells

*In Vitro* Expression of hVEGF in Human A375 cells +/- PR39

FIGURE 23
HCAR Adenovirus plus P39 Adenovirus Enhances Angiogenic Factor Expression in Mouse Fat Cells
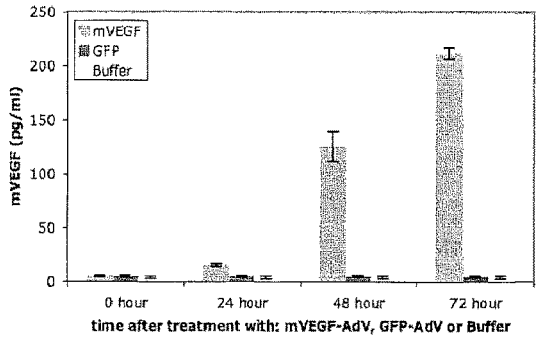
Figure 23A. mVEGF Expression Induced by mVEGF-AdV in Fat Cells
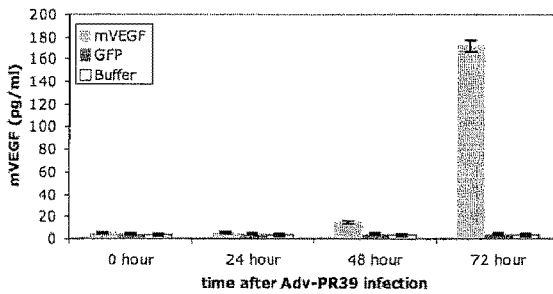
Figure 23B. mVEGF Expression induced by PR-39-AdV in Fat cells
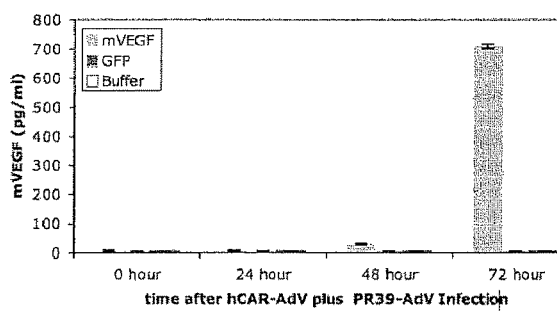
Figure 23C. mVEGF Expression induced by hCAR AdV plus PR-39 AdV in Fat Cells

FIGURE 24

List of Angiogenic Factors and Aniogenesis Related-Proteins

| | | |
|---|---|---|
| Activin A | FGF-7/KGF | PD-ECGF |
| ADAMTS-1 | GDNF | PDGF-AA |
| Angiogenin | GM-CSF | PDGF-AB/PDGF-BB |
| Angiopoietin-1 | HB-EGF | Persephin |
| Angiopoietin-2 | HGF | CXCL4/PF4 |
| Angiostatin/Plasminogen | IGFBP-1 | P/GF |
| Amphiregulin | IGFBP-2 | Prolactin |
| Artemin | IGFBP-3 | Serpin B5/Maspin |
| Tissue Factor/Factor III | IL-1 beta | Serpin E1/PAI-1 |
| CXCL 16 | CXCL8/IL-8 | Serpin F1/PEDF |
| DPPIV/CD26 | LAP (TGF-beta 1) | TIMP-1 |
| EGF | Leptin | TIMP-4 |
| EG-VEGF | CCL2/MCP-1 | Thrombospondin-1 |
| Endoglin/CD105 | CCL3/MIP-1 alpha | Thrombospondin-2 |
| Endostatin/Collagen XVIII | MMP-8 | uPA |
| Endothelin-1 | MMP-9 | Vasohibin |
| FGF acidic | NRG1-beta 1 | VEGF |
| FGF basic | Pentraxin 3 | VEGF-C |
| FGF-4 | | |

Figure 27 Glucose Sensors with collars and sleeves with no additives

Figure 28 Glucose Sensors with anti-microbial and or TRMs Containing collars and sleeves Figure 30 Glucose sensor Figure 31. Glucose Sensor with collars Containing anti-microbial agents and or TRMs

FIGURE 32. cannula with collars alone or containing, anti-microbial agents and or TRMs t = time post implantation

Figure 33 insulin infusion set with no collars

Figure 34 insulin infusion set with collar

Collar sleeve

FIGURE 38
Dialysis protocol for basement membrane (BM) preparations

Contents of commercial basement membrane preparations:
Basement membrane (10-20 mg / ml)
Media (DMEM or RPMI1640: >10-15mg/ml of salts, glucose, amino acids)
Liquid (water)

Dialysis of BM in 2000M.W. cut off dialysis membrane for 24 hr. (1/25 dilution) at 4C

Second Dialysis of BM in 2000M.W. cut off dialysis membrane for 24 hr. (1/25 dilution) at 4C

Final Dialysis dilution of BM 1/625: 0.016 to 0.024 mg/ml salts, glucose, amino acids

Use this dialyzed BM for coating devices

FIGURE 39

Typical formulation of DMEM and RPMI1640

From Sigma Chemical Co.

RPMI-1640 Media Formulation

- RPMI-1640 Medium
- RPMI-1640 Medium Dutch Modification
- RPMI-1640 Medium HEPES Modification
- RPMI-1640 Medium Modified
- RPMI-1640 Medium Auto-Mod™ for Autoclaving

RPMI-1640 Medium

| Component | R0883 [1x] g/L |
|---|---|
| Inorganic Salts | |
| Calcium Nitrate • 4H$_2$O | 0.1 |
| Magnesium Sulfate (anhydrous) | 0.04884 |
| Potassium Chloride | 0.4 |
| Sodium Bicarbonate | 2 |
| Sodium Chloride | 6 |
| Sodium Phosphate Dibasic (anhydrous) | 0.8 |
| Amino Acids | |
| L-Alanyl-L-Glutamine | — |
| L-Arginine | 0.2 |
| L-Asparagine (anhydrous) | 0.05 |
| L-Aspartic Acid | 0.02 |
| L-Cystine • 2HCl | 0.0652 |
| L-Glutamic Acid | 0.02 |
| L-Glutamine | — |
| Glycine | 0.01 |
| L-Histidine | 0.015 |
| Hydroxy-L-Proline | 0.02 |
| L-Isoleucine | 0.05 |
| L-Leucine | 0.05 |
| L-Lysine • HCl | 0.04 |
| L-Methionine | 0.015 |
| L-Phenylalanine | 0.015 |
| L-Proline | 0.02 |
| L-Serine | 0.03 |
| L-Threonine | 0.02 |
| L-Tryptophan | 0.005 |
| L-Tyrosine • 2Na • 2H$_2$O | 0.02883 |
| L-Valine | 0.02 |
| Vitamins | |
| D-Biotin | 0.0002 |
| Choline Chloride | 0.003 |
| Folic Acid | 0.001 |
| myo-Inositol | 0.035 |
| Niacinamide | 0.001 |
| p-Aminobenzoic Acid | 0.001 |
| D-Pantothenic Acid (hemicalcium) | 0.00025 |
| Pyridoxine • HCl | 0.001 |
| Riboflavin | 0.0002 |
| Thiamine • HCl | 0.001 |
| Vitamin B$_{12}$ | 0.000005 |
| Other | |
| D-Glucose | 2 |
| Glutathione (reduced) | 0.001 |
| Phenol Red • Na | 0.0053 |
| Add | |
| L-Glutamine | 0.3 |
| Sodium Bicarbonate | — |

Dulbecco's Modified Eagle's Medium (DME) Formula

| Component | D0422 [1x] g/L | D1145 [1x] g/L |
|---|---|---|
| Inorganic Salts | | |
| Calcium Chloride | 0.2 | 0.2 |
| Ferric Nitrate • 9H$_2$O | 0.0001 | 0.0001 |
| Magnesium Sulfate (anhydrous) | 0.09767 | 0.09767 |
| Potassium Chloride | 0.4 | 0.4 |
| Sodium Bicarbonate | 3.7 | 3.7 |
| Sodium Chloride | 6.4 | 6.4 |
| Sodium Phosphate Monobasic (anhydrous) | 0.109 | 0.109 |
| Amino Acids | | |
| L-Arginine • HCl | 0.084 | 0.084 |
| L-Cystine • 2HCl | — | 0.0626 |
| Glycine | 0.03 | 0.03 |
| L-Histidine • HCl • H$_2$O | 0.042 | 0.042 |
| L-Isoleucine | 0.105 | 0.105 |
| L-Leucine | 0.105 | 0.105 |
| L-Lysine • HCl | 1.46 | 0.146 |
| L-Methionine | — | 0.03 |
| L-Phenylalanine | 0.066 | 0.066 |
| L-Serine | 0.042 | 0.042 |
| L-Threonine | 0.095 | 0.095 |
| L-Tryptophan | 0.016 | 0.016 |
| L-Tyrosine • 2Na •2H$_2$O | 0.10379 | 0.6351 |
| L-Valine | 0.094 | 0.094 |
| Vitamins | | |
| Choline Chloride | 0.004 | 0.004 |
| Folic Acid | 0.004 | 0.004 |
| myo-Inositol | 0.0072 | 0.0072 |
| Niacinamide | 0.004 | 0.004 |
| D-Pantothenic Acid (hemicalcium) | 0.004 | 0.004 |
| Pyridoxal • HCl | — | — |
| Pyridoxine • HCl | 0.004 | 0.004 |
| Riboflavin | 0.0004 | 0.0004 |
| Thiamine • HCl | 0.004 | 0.004 |
| Other | | |
| D-Glucose | 4.5 | 4.5 |
| Phenol Red • Na | 0.0159 | — |
| Pyruvic Acid • Na | 0.11 | — |
| Add | | |
| L-Glutamine | 0.584 | 0.584 | back to top

FIGURE 40
In vitro evaluation of pre and post dialyzed basement membrane (BM): crystal formation upon drying Fig. 40A 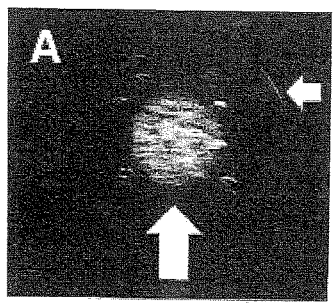
Fig. 40B 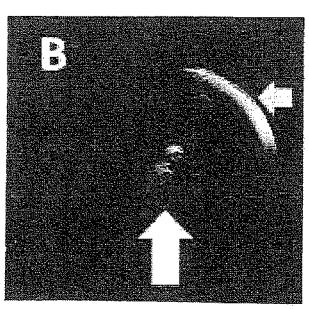
Fig. 40C 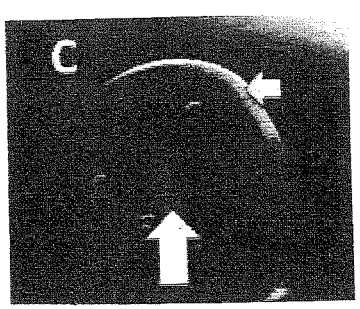

No dialysis | After 1<sup>st</sup> dialysis | After 2<sup>nd</sup> dialysis step

| Pre-dialysis BM: crystal formation After drying (24hr. | 1<sup>st</sup> Post-dialysis BM: no crystal formation After drying (24hr. 37C) | 2<sup>nd</sup> Post-dialysis BM: no crystal formation After drying (24hr. 37C) |

1. White arrows indicate area of crystal formation (red circle) as well as lack of crystal formation (C.)
2. Yellow arrows designate edge of dried protein layer (BM

FIGURE 41

In vivo evaluation of pre and post dialyzed basement membrane (BM): tissue reaction in mouse skin

Pre-dialysis BM

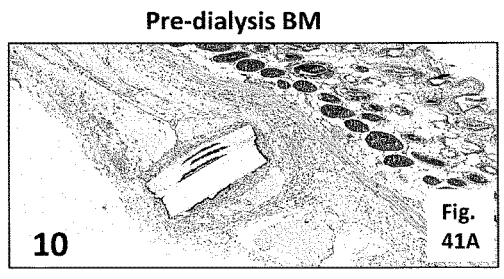

Fig. 41A

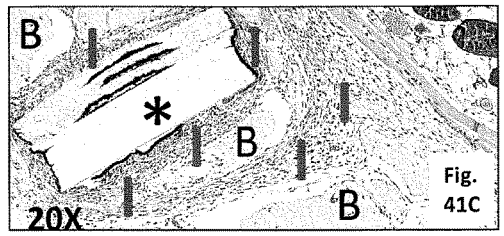

Fig. 41C

* = Sensor, B = BM; I = inflammation

Glucose sensor coated with Pre-dialysis BM and drying (24hr. 37C) Followed by implantation in subcutaneous tissue of mouse followed by histopathologic evaluation (H&E)
Results: tissue injury and inflammation with extensive degradation of the basement membrane

Post-dialysis BM

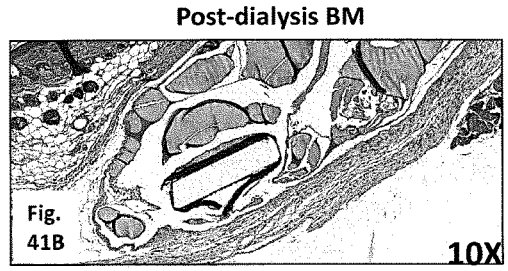

Fig. 41B

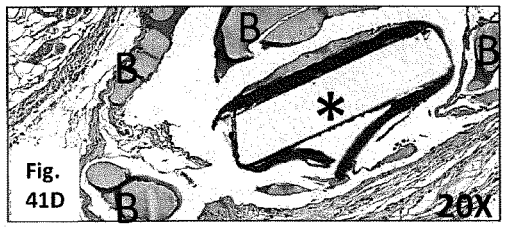

Fig. 41D

* = Sensor, B = BM; I = inflammation

Glucose sensor coated with Post-dialysis BM and drying (24hr. 37C) Followed by implantation in subcutaneous tissue of mouse followed by histopathologic evaluation (H&E)
Results: little tissue injury or inflammation with little degradation of the basement membrane

Figure 47
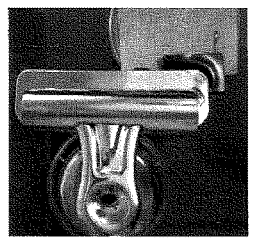
Fig. 47A
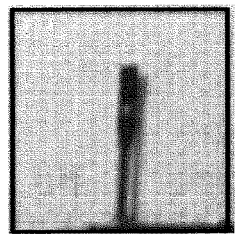
Fig. 47B
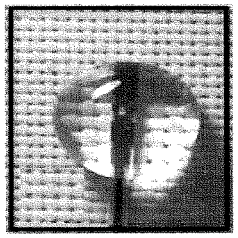
Fig. 47C
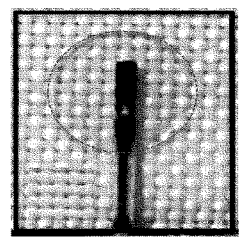
Fig. 47D
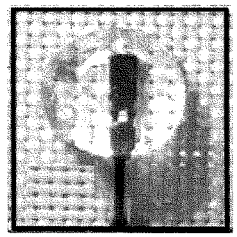
Fig. 47E
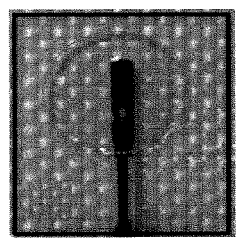
Fig. 47F
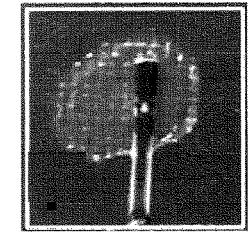
Fig. 47G
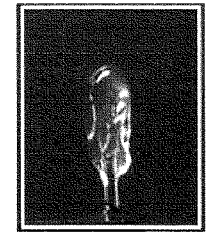
Fig. 47H
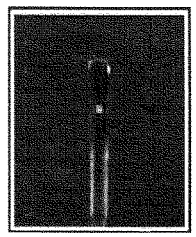
Fig. 47I
Fig. 47J
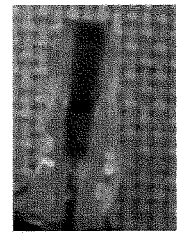
Fig. 47K
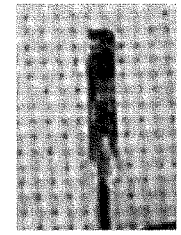
Fig. 47L Trend Analysis of First Week Abbott Sensor MARDs, Coated with Non-Cross-linked Cultrex and Cross-linked Cultrex along with Uncoated Control CD-1 Mice Characterization of the presence and distribution of macrophages at glucose sensor sites in vivo

FIGURE 52

| mean MARD data student *t*-test and Mann-Whitney U-test Comparisons | Day 7 | Day 14 | Day 21 | Day 28 | All weeks together |
|---|---|---|---|---|---|
| Cultrex CD-1 vs CD-1 Control | 0.0768 | 0.0058 | 0.0303 | 0.1774 | 0.0114 |
| X-Cultrex CD-1 vs Cultrex CD-1 | 0.0014 | 0.0000 | 0.0001 | 0.0148 | 0.0000 |
| X-Cultrex CD-1 vs CD-1 Control | 0.0000 | 0.0000 | 0.0000 | 0.0004 | 0.0000 |
| ANOVA and K-W tests for all 3 groups | 0.0000 | 0.0000 | 0.0000 | 0.0022 | 0.0000 |

FIGURE 53

| Total mean MARD data student *t*-test | CD-1 Control average mean MARD-20.52 +/- 6.58% n=39 | Cultrex CD-1 average mean MARD- 16.70 +/- 5.29% n=34 | X-Cultrex CD-1 average mean MARD- 10.59 +/- 2.94% n=26 |
|---|---|---|---|
| CD-1 Control average mean MARD-20.52 +/- 6.58% n=39 | --------------- | 0.0114 | 0.0000 |
| Cultrex CD-1 average mean MARD- 16.70+/- 5.89% n=34 | | --------------- | 0.0000 |
| X-Cultrex CD-1 average mean MARD- 10.59+/- 2.94% n=26 | | | --------------- |

COATED SURGICAL MESH, AND CORRESPONDING SYSTEMS AND METHODS

STATEMENT WITH REGARD TO FEDERAL SPONSORED RESEARCH & DEVELOPMENT

Some of the embodiments described herein may have been made with Government support under Grants awarded by the National Institute of Health. The Government may have certain rights in the described embodiments.

RELATED APPLICATIONS

This application claims priority from co-pending International Application No. PCT/US15/49718 filed Sep. 11, 2015, U.S. application Ser. No. 14/485,313 filed Sep. 12, 2014, and U.S. application Ser. No. 13/828,854 filed Mar. 14, 2013.

BACKGROUND

The embodiments disclosed herein generally relate to implantable devices and more particularly to systems and methods for improving performance of implantable devices.

The performance and accuracy of transcutaneous and implantable sensors is believed to be affected by biofouling, tissue reactions at or near the site of the sensor, and reduction of analyte access due to inflammation, blood vessel regression and fibrous encapsulation. In addition to causing problems with sensor function, tissue reactions and sensitivities due to the presence of transcutaneous and totally implantable sensors can cause discomfort to a user, and can lead to inflammation and infection.

In diabetic patients, determination and effective management of blood glucose levels is critical to minimizing diabetes related complications. Traditionally finger sticking and external monitors coupled with insulin injections have been used to manage blood glucose levels in patients with diabetes, but because of the need for frequent "finger sticks", many patients with diabetes do not adequately monitor their blood glucose levels. More recently, the development of implantable glucose sensors to continuously monitor blood glucose levels (CGM) and continuous insulin infusion (subcutaneous insulin infusion, SCII) have significantly enhanced the management of blood glucose levels in patients with diabetes. Current glucose sensors used in CGM limits the need for frequent blood analysis and provides significantly enhanced insights into the dynamic nature of blood glucose changes in patients with diabetes. Unfortunately, current commercial sensors have a limited functional lifespan in vivo (3-7 days).

When CGM and SCII are combined in a single patient, but under the supervision of the patient, it is referred to as an open loop system. When the implanted glucose sensor (i.e. CGM) controls insulin infusion (i.e. SCII) without the intervention of the patient this is referred to as a "closed loop" system or artificial pancreas. Development of an artificial pancreas (i.e. closed-loop technology) to clinically manage diabetes is a major goal of the diabetes community. Recently, there have been an increasing number of success stories of short-term closed-loop clinical trials.

Central to the goal of the development of long-term closed loop technology is the development of a long-term glucose sensor with high accuracy that can effectively control insulin infusion (SCII). Because of questions of in vivo reliability and limited lifespan of current commercial sensors effectiveness in both open and closed loop systems is limited. Much of the lack of sensor performance in vivo is thought to be the result of sensor induced inflammation, fibrosis and fibrosis-induced vessel regression at the site of sensor implantation. It has often been argued that the loss of blood vessels proximal to the sensor (i.e. fibrosis induced vessel regression) at the sensor implantation site is a major cause of the loss of effective CGM in open and closed loop systems.

Two of the major problems associated with the uses of prosthetic meshes are 1) their propensity to induce chronic inflammation and excessive fibrosis, with resulting loss of mesh pliability and mechanical integrity, increased stiffness at the site of the implantation, and 2) post mesh implantation infections. Frequently the result of poor mesh biocompatibility is excessive inflammation and subsequent fibrosis. This can result in limited tissue mobility of the groin and abdominal wall and chronic pain and loss of mobility for the patient. It is generally accepted that foreign body reactions (FBRs) characterized by chronic inflammation, giant cell formation, fibrosis (collagen plates) and vessel regression result in loss of mesh function via mesh contraction and mesh distortion (e.g. loss of functional pore size), as well as mesh calcification. Clearly, improving the biocompatibility of the mesh implants (i.e. decreasing inflammation and fibrosis) and mesh biostability, given the susceptibility of PET to enzymatic & hydrolytic degradation is anticipated to result in improved mesh function by decreasing mesh distortion, calcification and loss of mechanical integrity that are all too commonly associated with mesh-based reconstructive surgeries.

In addition to biocompatibility, infection associated with mesh implantation frequently compromise mesh function and dramatically impact a patient's daily life. The timeframe for mesh related infections range from 10 days post implantation (short term) up to several years post mesh implantation (long term infections). Mesh infections increase pain and discomfort, hospital stay, healing/recovery time, cost, morbidity, mortality, and may require additional surgery to remove device.

It would be useful to develop products, systems and methods that maintain acceptable performance over longer periods of time, and that reduce tissue reactions and sensitivities at or near the implantation site.

SUMMARY

One embodiment disclosed herein is a surgical mesh with a layer of dehydrated basement membrane formed thereon.

Another embodiment is a method comprising obtaining a surgical mesh, placing basement membrane in the form of a liquid or gel on the surgical mesh, and dehydrating the basement membrane. In embodiments, the basement membrane has cells, factors, or other additives incorporated therein.

Another embodiment is a method of extending the lifespan of an implantable device that is implanted in biological tissue, comprising bonding vascular endothelial growth factor to fibronectin, adding the fibronectin to a liquid or gel comprising extracellular matrix, and coating the implantable device with the extracellular matrix containing fibronectin and vascular endothelial growth factor.

A further embodiment is a method of promoting biocompatibility of a surgical mesh with surrounding tissue, comprising forming a coating comprising basement membrane comprising adenovirus vectors containing VEGF gene on the surface of the surgical mesh.

One embodiment disclosed herein is an analyte sensor having a sensing end with dehydrated basement membrane formed thereon.

Another embodiment is a method comprising obtaining a sensor, placing basement membrane in the form of a liquid or gel on the sensor, and dehydrating the basement membrane on the sensor.

A further embodiment is a method of increasing the sensing lifespan of a glucose sensor in a mammal by at least 10 days, comprising injecting adenovirus vectors containing VEGF gene in the tissue proximate the site of sensor tip implantation.

Another embodiment is a method of extending the lifespan of an implantable device that is implanted in biological tissue, comprising bonding vascular endothelial growth factor to fibronectin, adding the fibronectin to a liquid or gel comprising extracellular matrix, and coating the implantable device with the extracellular matrix containing fibronectin and vascular endothelial growth factor.

Yet another embodiment is an implantable device including at least one member selected from the group consisting of sensors, cannulas and surgical mesh, the device having an implantable portion with a coating of dehydrated extracellular matrix formed thereon.

One embodiment disclosed herein is an implantable device with a layer of dehydrated basement membrane formed thereon, the basement membrane layer comprising at least one member selected from the group consisting of sleeve-shaped coatings for cannulas, collars for cannulas, and collars for sensors.

Another embodiment disclosed herein is an implantable device having a collar configured to be disposed at an interface between tissue and the implantable device, the collar being formed from an extracellular matrix. In embodiments, the extracellular matrix is dehydrated prior to implantation and rehydrated after implantation.

Another embodiment is a method comprising obtaining an implantable device including at least one member selected from the group consisting of cannulas and sensors, placing basement membrane in the form of a liquid or gel on the cannula or sensor to form at least one of a sleeve and a collar, and dehydrating the basement membrane on the cannula or collar. In embodiments, the basement membrane has cells, factors, or other additives incorporated therein.

A further embodiment is a method of increasing by at least 10 days the lifespan of an implantable device comprising at least one member selected from the group consisting of cannulas and sensors inserted in a mammal, comprising forming an extracellular matrix coating around a portion of the implantable device in the form of a sleeve or a collar, the coating comprising dehydrated extracellular matrix which is rehydrated after implantation, the extracellular matrix having cells and/or factors attached thereto using fibronectin.

Another embodiment is a method of extending the lifespan of an implantable device that is implanted in biological tissue, comprising bonding vascular endothelial growth factor to fibronectin, adding the fibronectin to a liquid or gel comprising extracellular matrix, and coating the implantable device with the extracellular matrix containing fibronectin and vascular endothelial growth factor.

A further embodiment is a method of increasing the lifespan of an implantable device comprising at least one member selected from the group consisting of cannulas and sensors in a mammal, comprising forming a coating on the cannula or sensor in the shape of a sleeve and/or a collar, the coating comprising basement membrane comprising adenovirus vectors containing VEGF gene.

Yet another embodiment is analyte sensor having a sensing element and a support element, at least one of the sensing element and support element having a dehydrated modified basement membrane preparation formed thereon.

A further embodiment is a method comprising obtaining a basement membrane preparation containing basement membrane and at least one member selected from the group consisting of salts, glucose, individual amino acids, and vitamins and removing at least a portion of at least one of the salts, glucose, individual amino acids and vitamins from the basement membrane to form a modified basement membrane preparation.

The method further includes obtaining a sensor, placing the modified basement membrane preparation in the form of a liquid or gel on the sensor, and dehydrating the modified basement membrane preparation on the sensor.

Crosslinked Basement Membrane or Extracellular Matrix

An embodiment disclosed herein is an implantable device, the implantable device having a coating of crosslinked basement membrane formed thereon.

In embodiments, the implantable device is a sensor. In embodiments, the sensor has a sensing end, and the basement membrane is formed on the sensing end.

Another embodiment is a method comprising obtaining an implantable device, placing basement membrane in the form of a liquid or gel on the implantable device, and then dehydrating and crosslinking the basement membrane. In embodiments, the implantable device is a sensor.

Yet another embodiment is an implantable device including at least one member selected from the group consisting of sensors, cannulas and surgical mesh, the device having an implantable portion with a coating of crosslinked extracellular matrix formed thereon.

Another embodiment disclosed herein is an implantable device with a layer of crosslinked basement membrane formed thereon, the basement membrane layer comprising at least one member selected from the group consisting of sleeve-shaped coatings cannulas, collars for cannulas, and collars for sensors.

Another embodiment disclosed herein is an implantable device having a collar configured to be disposed at an interface between tissue and the implantable device, the collar being formed from an extracellular matrix. In embodiments, the extracellular matrix is crosslinked and dehydrated prior to implantation, and rehydrated and after implantation.

Another embodiment is a method comprising obtaining an implantable device including at least one member selected from the group consisting of cannulas and sensors, placing basement membrane in the form of a liquid or gel on the cannula or sensor to form at least one of a sleeve and a collar, and dehydrating and crosslinking the basement membrane on the cannula or collar. In embodiments, the basement membrane has cells, factors, or other additives incorporated therein.

A further embodiment is a method of increasing the lifespan of an implantable device comprising at least one member selected from the group consisting of cannulas and sensors inserted in a mammal, comprising forming crosslinked extracellular matrix coating around a portion of the implantable device in the form of a sleeve or a collar, the coating comprising dehydrated extracellular matrix which is rehydrated after implantation, the extracellular matrix having cells and/or factors attached thereto using fibronectin. In embodiments, the implantable device has a lifespan of at least 28 days. In embodiments, the device is a sensor, and the coated sensor is more accurate than the uncoated sensors, and more accurate than the sensors that are coated with non-crosslinked basement membrane, for the first day, and for the first seven days, of sensor use.

Yet another embodiment disclosed herein is a surgical mesh with a layer of crosslinked basement membrane formed thereon.

Another embodiment is a method comprising obtaining a surgical mesh, placing basement membrane in the form of a liquid or gel on the surgical mesh, and crosslinking the basement membrane. In embodiments, the basement membrane has cells, factors, or other additives incorporated therein.

A further embodiment is analyte sensor having a sensing element and a support element, at least one of the sensing element and support elements having a cross-linked basement membrane preparation formed thereon.

A further embodiment is a method comprising obtaining a basement membrane preparation containing basement membrane and at least one member selected from the group consisting of salts, glucose, individual amino acids, and vitamins and removing at least a portion of at least one of the salts, glucose, individual amino acids and vitamins from the basement membrane to form a modified basement membrane preparation. The method further includes obtaining a sensor, placing the modified basement membrane preparation in the form of a liquid or gel on the sensor, and dehydrating and crosslinking the modified basement membrane preparation on the sensor.

BRIEF DESCRIPTION OF THE DRAWINGS

FIGS. 6A-6D illustrates a method of injecting adenovirus vectors containing VEGF gene in accordance with a first embodiment. FIG. 6A shows the arrangement of the mouse, sensor, commutator, potentiostat, DAS and laptop. FIG. 6B shows injection of material post sensor implantation. FIG. 6C and FIG. 6D show the mouse post sensor implantation.

FIGS. 7A-7P are representative example graphs for the various treatment groups showing continuous glucose sensing (CGS) current for a period of 28 days in mice having adenovirus vectors containing mouse VEGF proximate the site of sensor implantation, as compared to three types of controls. FIGS. 7A-7D show the results for four non-injected control mice. FIGS. 7E-7H show the results for four saline injected mice. FIGS. 7I-7L show the results for four mice injected with Adv-LacZ adenovirus. FIGS. 7M-7P show the results for four mice injected with Adv-VEGFa adenovirus.

FIG. 10 is a Table of statistical analyses of the total MARD data for all treatment groups.

FIG. 13A is a table showing the relative contribution of blood vessel density to glucose sensor function.

FIG. 13B is a table showing a statistical comparison of lymphatic and blood vessel counts per square millimeter.

FIG. 13C is a table showing the contribution of lymph vessel density to glucose sensor function.

FIG. 13D is a table showing the contribution of both blood and lymph vessel density to glucose sensor function.

FIG. 14A shows a sensor with original Matrigel thereon. FIG. 14B shows dehydrated Matrigel and FIG. 14C shows rehydrated Matrigel.

FIG. 15A shows a test with no Matrigel and FIG. 15B shows the results when a Matrigel coating is used.

FIGS. 16A and 16B are graphs showing that basement membrane coated sensors perform better (less variation in sensor response in nA) and longer in vivo when compared to non-coated sensors. FIG. 16A shows a test with no Matrigel and FIG. 16B shows the results when a Matrigel coating is used.

FIGS. 17A, 17C and 17E are bright field photographs showing A375 cells. FIGS. 17B, 17D and 17E show the A375 cells when viewed under fluorescence microscopy.

FIGS. 18A and 18B are sets of photographs showing that when viral vectors are incorporated into ECM such as basement membrane that is coated on glucose sensors, dried, and then rehydrated, the ECM protects the viral vectors from loss of function. FIG. 18A shows a sensor coated with a GFP-adenovector-Matrigel coating. FIG. 18B shows a sensor coated with a GFP-adenovector-collagen coating.

FIGS. 19A-19D show that when using a transgenic mouse that expresses hCAR receptors (receptor for adenoviral vectors) on the surfaces of cells, these cells can be infected with efficiency when compared to wild type cells that lack the hCAR receptor, thus supporting the uses of hCAR transfections to enhance local gene transfer at sites of medical device implantation. FIGS. 19A and 19B show spleen cells from hCAR mice injected with GFP adenovirus. FIGS. 19C and 19D show that spleen cells from control (C57BL/J) mice could not be infected.

FIGS. 20A-20F are photographs showing that transfection of normal cells with hCAR adenovirus is not toxic to the recipient cells. Thus supporting the uses of hCAR or CAR gene therapy to enhance future infection by adenovirus viral vectors carrying various genes, which can control tissue reactions at sites of medical device implantation. FIG. 20B shows non-infected cells. FIG. 20D shows cells infected with GFP-Adv. FIG. 20F shows cells infected with GFP-Adv and then hCAR-Adv. FIGS. 20A, 20C and 20E are the brightfield controls to FIGS. 20B, 20D and 20F respectively.

FIGS. 23A-23C are graphs depicting an in vitro demonstration that using hCAR and PR-39 in combination induces a greater VEGF expression in mouse fat cells then if used individually. FIG. 23A shows mVEGF expression induced by mVEGF-ADV in fat cells. FIG. 23B shows mVEGF expression induced by PR-39-ADV in fat cells. FIG. 23C shows mVEGF expression induced by hCAR ADV plus PR-39 ADV in fat cells.

FIG. 24 shows a list of angiogenic factors and related proteins that could be used as recombinant proteins or be used as genes in local gene therapy or in combination to enhance vascular networks surrounding implanted medical devices.

FIG. 26A shows an uncoated sensor assembly. FIG. 26B shows the sensor in tissue. FIG. 26C shows a sensor assembly that includes an antimicrobial collar and/or a coating containing a tissue response modified disposed between the collar and the sensing element. FIG. 26D shows rehydration of the collar and coating.

FIG. 38 is a flow chart showing one embodiment for preparing a modified basement membrane preparation.

FIG. 39 shows formulations of two types of media used in making basement membrane products sold commercially.

FIG. 40 is a set of photos showing salt crystals in dehydrated basement membrane. FIG. 40A shows salt crystals after drying when no dialysis is used. FIG. 40B shows salt crystals after drying when a single dialysis step is used. FIG. 40C shows a lack of salt crystals after drying when two dialysis steps are used.

FIG. 41 includes photos showing the effect of pre-dialyzed and post-dialyzed basement membrane on tissue surrounding implanted sensors. FIGS. 41A and 41B show pre-dialysis basement membrane at 10× and 20× magnification, respectively. FIGS. 41C and 41D show post-dialysis basement membrane at 10× and 20× magnification, respectively.

FIG. 47 illustrates a process for dehydrating and crosslinking basement membrane on an implantable device. FIGS. 47A-47C show mounting of a glucose sensor and application of dialyzed basement membrane. FIG. 47D shows the dried basement membrane on the sensor. FIGS. 47E and 47F show application of dialyzed basement membrane to the other side of the sensor, followed by drying. FIG. 47G, FIG. 47H and FIG. 47I show removal of the sensor from the liner, dipping and drying. FIG. 47J, FIG. 47K and FIG. 47L showing dipping and drying of the coated sensor.

Figure 50:
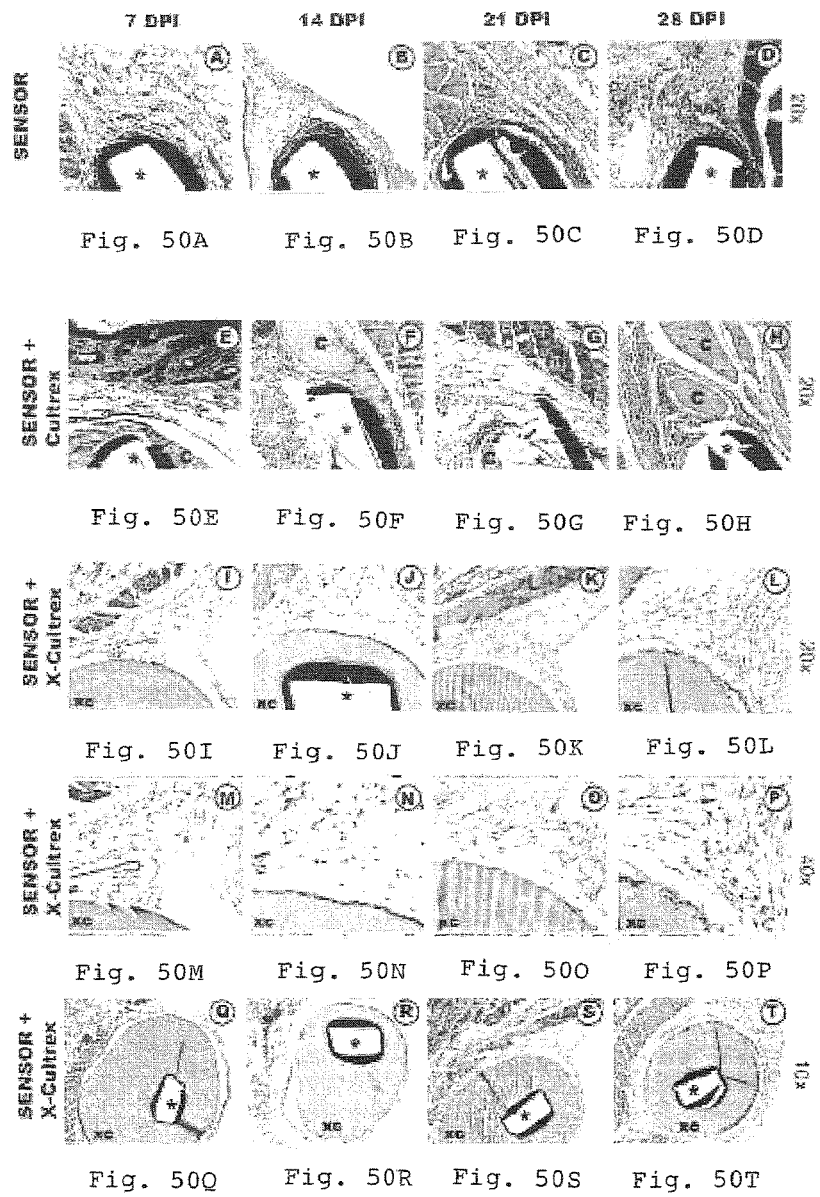

FIG. 50 is a set of histo-pathologic photomicrographs showing samples from Example 16 at 7 days post implant, 14 days post implant, 21 days post implant and 28 days post implant. FIG. 50A, FIG. 50B, FIG. 50C and FIG. 50D show uncoated sensors. FIG. 50E, FIG. 50F, FIG. 50G and FIG. 50H show sensors coated with non-crosslinked basement membrane. FIG. 50I, FIG. 50J, FIG. 50K and FIG. 50L show sensors coated with crosslinked basement membrane at 20× magnification. FIG. 50M, FIG. 50N, FIG. 50O and FIG. 50P show sensors coated with crosslinked basement membrane at 40× magnification. FIG. 50Q, FIG. 50R, FIG. 50S and FIG. 50T show sensors coated with crosslinked basement membrane at 10× magnification.

Figures 51, 51A, 51B, 51C, 51D, 51E, 51F, 51G, 51H:
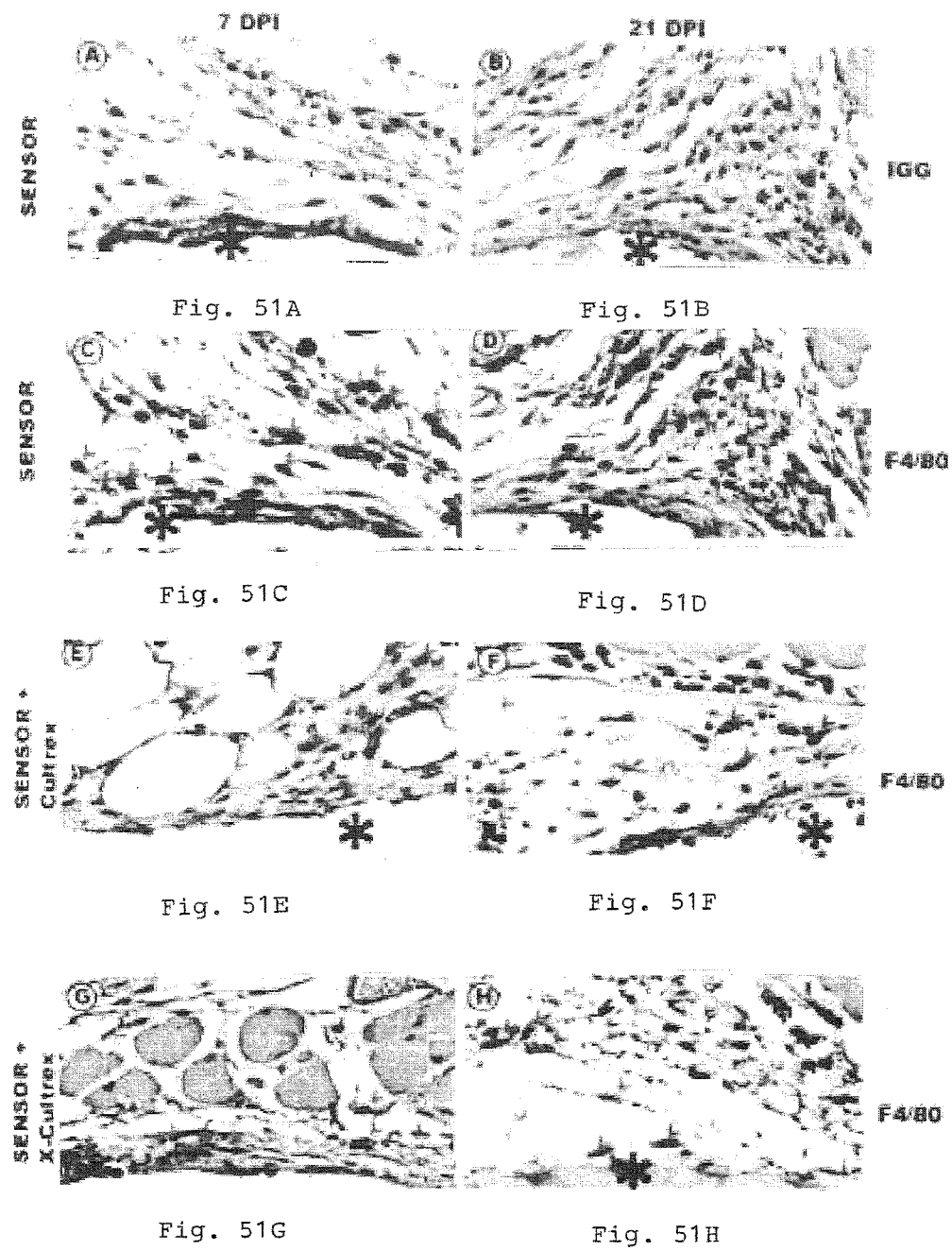

FIG. 51 is a set of immuno-histologic photomicrographs showing the presence and distribution of macrophages at the site of glucose sensor implantation. FIG. 51A, FIG. 51B, FIG. 51C and FIG. 51D show uncoated sensors. FIG. 51E and FIG. 51F show sensors coated with uncrosslinked basement membrane. FIG. 51G and FIG. 51H show sensors coated with crosslinked basement membrane.

FIG. 52 is a table showing mean MARD data for statistical analysis of Mean Mards sensor performance between different test groups. The values in the individual boxes are p values for statistical significance between each comparison at 7, 14, 21 and 28 days post sensor implantation.

FIG. 53 is a table showing total MARD data for comparison of statistical significance between the selected groups of mice implanted with glucose sensors.

Figure 54:
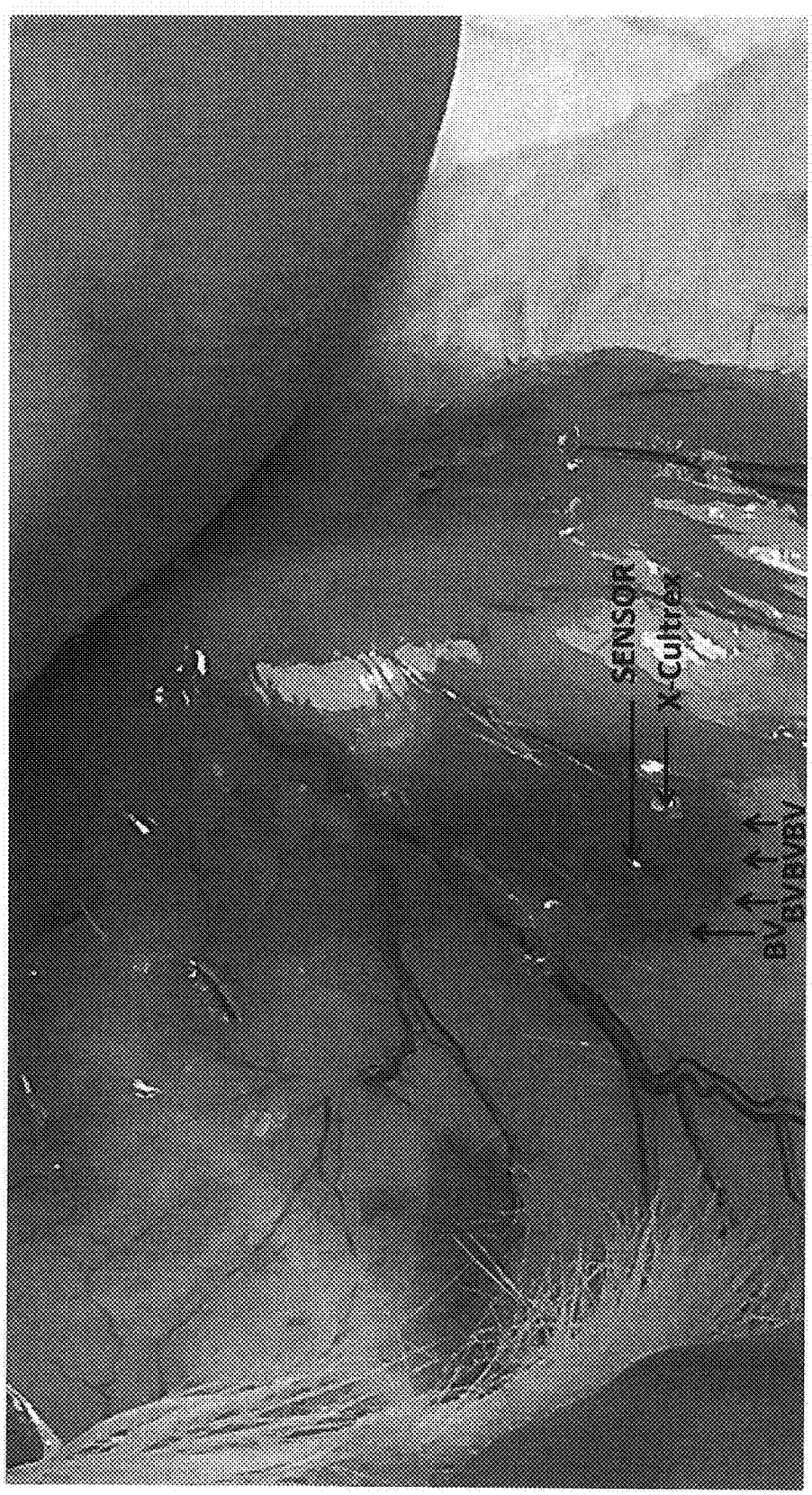

FIG. 54 is a photomicrograph showing vessel formation after a 2 month term of sensor implantation.

DETAILED DESCRIPTION

Based on work described herein, the applicant believes that both fibrosis itself and fibrosis-induced vessel regression work synergistically to limit effective CGM in vivo. Specifically, fibrosis not only induces blood vessel regression at sites of sensor implantation but fibrosis is also known to slow glucose diffusion between the blood vessel and the implanted glucose sensor. This fibrosis based inhibition of glucose diffusion results in the loss of "real time" blood glucose measurements because of the element of time delay.

In the past, efforts to overcome fibrosis and vessel regression in injured tissues such as ischemic hearts and limbs have focused on the uses of recombinant angiogenic factors (AF) and genes (e.g. VEGF) to induce tissue regeneration. Although local delivery of recombinant AF such as VEGF can cause neovascularization of the tissue, the ceasing of AF delivery generally results in vessel regression and loss of tissue viability. This limitation of recombinant AF has spurred efforts to utilize local AF gene therapy to create and sustain vascular networks at sites of tissue injury and ischemia. Although there has been significant discussion related to the importance of neovascularization in sensor function, in actuality there have only been limited sensor studies to demonstrate its effect. In all the cases known to the applicant, the issue of vessel regression with the ceasing of VEGF delivery remains a major problem with this approach.

Embodiments described herein utilize a murine model of CGM and adenovirus based local gene therapy over a 28 day time period, and show that local gene therapy using VEGFa adenoviruses can induce significant angiogenesis and neovascularization at sensor implantation sites and thereby significantly extend glucose sensor life spans in VIVO.

A new and effective way of applying coatings to sensors is also described herein. In the past, biological coatings were applied in liquid or gel form at the time they were to be used. In embodiments described herein, one or more coatings are applied to the sensors and then dehydrated. The sensors can then be packaged in sterile packaging for shipping. The sensors are implanted with dehydrated coatings present thereon. The coatings will become rehydrated due to the presence of liquid in the surrounding tissue after they have been implanted.

In embodiments, a final hydration step is added before implantation to remove salts that have accumulated as a result of the multiple layering/coating of the sensor. This high salt might be toxic if the coated implantable device was implanted directly into the tissue (salt comes, for example, from the Matrigel buffers, which are important to stabilize the Matrigel in its liquid form).

Additionally, this rehydration step can also be used to incorporate additional factors into the Matrigel such as angiogenic factors, drugs, antimicrobials. This can be important if the factors tend to be libel (be effected by temperature or repeated drying).

Definitions

The general meaning of the following terms as used in the present application, unless specifically modified, are: "Normal Cells": biological cells derived from living organisms, and/or tissues, which retain a normal genotype and phenotype, usually obtained directly from tissue or from primary culture. "Mutant Cells": biological cells with spontaneously altered genotype and phenotype, such as cancer cells, cell derived from naturally occurring genetically deficient organisms, usually obtained in secondary culture and or continuous cell lines. "Engineered Cells": genetically or chemically modified biological cells (usual original source is Normal or Mutant cells). "Transgenic Cells": biological cells derived from transgenic animals, in which the cells have genetically induced alterations of genotype and or phenotype. "Gene Transfer Cells": biological cells that have altered phenotype resulting in alteration of cell structure and or function. This includes knockouts, knockdowns, "over-expressors" etc. "Chemically Modified Cells": biological cells in which membrane, cytoplasm structural or enucleolar elements of the cell are altered permanently or for extended periods, thus altering cell structure and or function. "Artificial Cells": biological cells lacking the ability to replicate but capable of sensing and responding to their microenvironment. For example enucleated cells, or cells lacking a nucleus (e.g. red blood cells), in which genetic elements such as DNA, RNA, viral vectors, nanodevices or nanomaterials can be incorporated for in vivo uses. "Hybrid Cells": biological cells that are the result of cells fusion, and or combinations of engineered and or artificial cells. "Matrix material": complex heterogeneous networks of insoluble macromolecules such as glycoproteins, carbohydrates, structural proteins (e.g. collagen), as well as bound proteins and factors. These matrices contain specific binding sites for cells, factors (e.g. cytokines and growth factors) and proteins, which directly control cell adhesion and function in vivo and in vitro. "Biological Matrices": matrices obtained from organisms, tissues, or cell. Examples of biological matrices include interstitial matrices, basement membrane, fibrin clots. Interstitial matrices are generally composed of fibrillar and nonfibrillar collagen, elastin, fibronectin proteoglycans, hyuronate, as well as other components. Basement membranes are composed of nonfibrillar collagen (usually IV), laminin, heparin sulfate, proteoglycan, and other glycoproteins. Fibrin clots are complex networks of plasma proteins including fibrin(ogen), fibronectin, glycoproteins, heparin, thrombin collagen, as well as other plasma proteins crosslinked to the fibrin clots via Factor XIII. Additionally, fibrin clots have extensive binding sites for various factors and cells including leukocytes, fibroblasts and endothelial cells. "Engineered Matrices": genetically and or chemically modified biological matrices. "Hybrid matrices": combinations of biological, engineered and or artificial matrices. In addition, the meaning of various abbreviations as used within the present application, unless specifically modified, include ES, embryonic stem cell; MSC, mesenchymal stem cell; MAPC, multipotent adult progenitor cell; HSC, hematopoietic stem cell; NSC, neural stem cell; NPC, neural progenitor cell; MDSC, muscle-derived stem cell; ECM, extracellular matrix; EGF, epidermal growth factor; LIF, leukemia inhibitory factor; SCF, stem cell factor; HGF, hepatocyte growth factor; PDGF, platelet-derived growth factor; VEGF, vascular endothelial growth factor; BMP, bone morphogenetic protein; BDNF, brain-derived neurotrophic factor; NT, neurotrophin; CNTF, ciliary neurotrophic factor; bFGF, basic fibroblast growth factor; TGF-ß, transforming growth factor-beta; IL, interleukin; G-CSF, granulocyte-colony stimulating factor; GM-CSF, granulocyte-macrophage colony stimulating factor; IGF, insulin-like growth factor; RA, retinoic acid; and FBS, fetal bovine serum.

As used herein, "extracellular matrix" (ECM) means biological matrices produced by cells, which can create 3D complexes. Examples include, basement membranes, collagens, fibrin etc. As used herein, "artificial tissue system (ATS)" is a combination of extracellular matrices as well as other additives and cells that can be coated on the surface of an implantable device to enhance the biocompatibility of the device and its performance. "Sensor response" is the raw output in nano-amperes (nA) of a sensor in vivo or in vitro. "Loss of sensor response" is defined as not correlating with previously measured glucose values, e.g. when the same glucose level is present while at the same time the output in nA consistently falls over time, or when glucose levels increase but the sensor does not detect this increase. "Loss of sensor function" as used herein refers to a fall in sensor output (nA) over time with a non-changing glucose level.

In the context of glucose sensors, "sensor sensitivity" is measured as nano-Amps per milli-mole of glucose or nano-Amps per mg of analyte (such as glucose) per deciliter. The mM glucose or dL glucose level is derived from an external meter, using blood from a finger prick, to make the glucose determination. The sensor output and external monitor measurements are made at the same time. Loss of sensor sensitivity can be expressed as the ratio between the change in sensor response in nA divided by the change in blood analyte concentration in mM. See Klueh U, Kreutzer, D, "Murine model of implantable glucose sensors: a novel model for glucose sensor development," *Diabetes Technol. Ther.* 2005, 7:727-737, the contents of which are incorporated by reference herein in their entirety.

"Sensor lifespan" refers to the time, in days or hours, that sensor output and sensitivity are adequate to allow detection of whether or not the analyte levels in an organism are acceptable. In a glucose sensor, the lifespan is a time that sensor output is adequate to detect whether blood glucose levels are normal glycemic, hypoglycemic, or hyperglycemic.

As used herein, "dehydrated biological matrix" refers to dried, solid biological matrix. "Dehydrated basement membrane" refers to dried, solid basement membrane.

As used herein, "cell culture derived basement membrane" refers to basement membrane, which is extracted (solubilized) from in vitro cell cultures containing mammalian cells. As used herein, "tissue derived basement membrane" refers to basement membrane, which is isolated/extracted from animal tissues such as intestines. As used herein "solubilized basement membrane" means any soluble basement membrane obtained from cells in culture or mammalian tissue. As used herein, "liquid basement membrane" refers to basement membrane which is fluid basement membrane which exists in many cases at temperatures at 4° C. or below whereas gel basement membrane will start to form above 10 Deg. C. and will gel rapidly at 22-35 Deg. C.

As used herein, "lymphangiogenesis" refers to the formation of new lymphatic vessels. "Angiogenesis" refers to the formation of new blood vessels.

As used herein, "viral gene therapy" refers to the insertion of gene-containing viruses into a host. The virus produces a continuing supply of the gene product. "Recombinant protein" are proteins that are normally produced in vitro and then purified and then subsequently injected or delivered to a host tissue or vascular.

As used herein "cannula", refers to an elongated tube configured for delivery of a liquid, such as saline or a pharmaceutical product. A catheter is a type of a cannula. As used herein, "collar" refers to a three dimensional, annular device configured to surround an elongated cannula, sensor, or other device to the surface of tissue such as skin tissue. The collar usually is positioned between the device and the skin layer.

As used herein, "modified basement membrane preparation" means a basement membrane solution or gel from which the small molecular weight components have been removed, including but not necessarily limited to salts, glucose, individual amino acids and vitamins. "Modified extracellular matrix preparation" as used herein means an extracellular matrix solution or gel from which the small molecular weight components have been removed, including but not necessarily limited to salts, glucose, individual amino acids and vitamins.

As used herein, "crosslinked basement membrane" means a basement membrane in the form of a gel or solid in which the basement membrane is crosslinked with a crosslinking agent that induces covalent bonding within the basement membrane preparations. In embodiments, the crosslinking agent is biocompatible at the concentrations in which it is used.

List of a First Set of Product Embodiments Described Herein

1. In one embodiment, the coated sensor, which has not yet been inserted in a user, has an outer coating of dehydrated extracellular matrix (ECM) formed thereon, such as basement membrane.
2. In another embodiment, the coated sensor, which has not yet been inserted into a user, has a coating of dehydrated basement membrane formed therein, with additives incorporated therein (protein and non-protein substances such as factors (drug), cytokines, and antibodies).
3. In another embodiment, the coated sensor has multilayer coatings, including a first coating of an extracellular matrix followed by a second coating of the same or a different extracellular matrix.
4. In another embodiment, the ECM coated sensors, which is a transdermal or totally implantable sensor, has been implanted and the basement membrane has been rehydrated in the tissue following implantation. In embodiments, the body's own fluids rehydrate the membrane.

5. In yet another embodiment, a system (kit) that includes at least one extracellular matrix, a device to apply the ECM to the implant and a protocol for using the kit to coat the implant with at least one layer of ECM as well as a specific drying and hydrating method described.

A First Set of Disclosed Method Embodiments

In yet another embodiment, a method of making (coating) a sensor is described in which basement membrane in the form of a liquid or gel is applied to a sensor and dehydrated at ambient temperature. The basement membrane is later rehydrated before or after the sensor is inserted in a user.

In a further embodiment, the method of making a sensor is described in which basement membrane in the form of a liquid is applied to a sensor at 4° C. and dehydrated at a temperature in the range of 4 Deg. C. The basement membrane is later rehydrated after the sensor is inserted in a user.

Another embodiment is a method of making a sensor in which a coating is applied, before as a coating or "insertion pocket" and/or after insertion in a user, which promotes lymphangiogenesis. The coating comprises at least one extracellular matrix and at least lymphangiogenesis factor such as VEGF-C.

List of a Second Set of Product Embodiments Described Herein

1. In one embodiment, the coated cannula, which has not yet been inserted in a user, has an outer coating of dehydrated basement membrane.
2. In another embodiment, the coated cannula, which has not yet been inserted into a user, has a coating of dehydrated basement membrane formed therein, with additives incorporated therein (protein and non-protein substances such as factors (drug), cytokines, antibodies).
3. In another embodiment, the coated cannula has multilayer coatings, including a first coating of an extracellular matrix followed by a second coating of the same or a different extracellular matrix.
4. In another embodiment, the ECM coated cannulas, which may be affiliated with a transcutaneous or totally implantable sensor, has been implanted and the basement membrane has been rehydrated in the tissue following implantation.
5. In a further embodiment, a collar for a sensor or other implantable device is itself made out of extracellular matrix material such as basement membrane. The collar may be formed of one layer, or multiple layers. Multi-layer collars can have layers that are formed from different ECMs and/or contain different additives.
6. In yet another embodiment, a system (kit) that includes at least one extracellular matrix, a device to apply the ECM to the implant and a protocol for using the kit to coat the implant with at least one layer of ECM as well as a specific drying and hydrating method described.
7. Cannulas used herein can be employed in conjunction with an infusion device, such as an insulin pump. An infusion pump infuses fluids, medication or nutrients into a patient's circulatory system. It is generally used in subcutaneous, intravenously, arterial and epidural infusions A Second Set of Disclosed Method Embodiments In yet another embodiment, a method of making (coating) a cannula is described in which basement membrane in the form of a liquid or gel is applied to a cannula and dehydrated at ambient temperature. The basement membrane is later rehydrated before or after the cannula is inserted in a user.

In a further embodiment, the method of making a cannula or collar is described in which basement membrane in the form of a liquid is applied to a sensor at 4° C. and dehydrated at a temperature in the range of 4 Deg. C. The basement membrane is later rehydrated after the cannula or collar is inserted in a user.

Another embodiment is a method of making a cannula or collar in which a coating is applied, before as a coating or "insertion pocket" and/or after insertion of the cannula or collar in a user, which promotes lymphangiogenesis. The coating comprises at least one extracellular matrix and at least lymphangiogenesis factor such as VEGF-C.

List of a Third Set of Product Embodiments Described Herein

8. In one embodiment, the coated cannula, which has not yet been inserted in a user, has an outer coating of dehydrated basement membrane.
9. In another embodiment, the coated cannula, which has not yet been inserted into a user, has a coating of dehydrated basement membrane formed therein, with additives incorporated therein (protein and non-protein substances such as factors (drug), cytokines, antibodies).
10. In another embodiment, the coated cannula has multilayer coatings, including a first coating of an extracellular matrix followed by a second coating of the same or a different extracellular matrix.
11. In another embodiment, the ECM coated cannulas, which may be affiliated with a transcutaneous or totally implantable sensor, has been implanted and the basement membrane has been rehydrated in the tissue following implantation.
12. In a further embodiment, a collar for a sensor or other implantable device is itself made out of extracellular matrix material such as basement membrane. The collar may be formed of one layer, or multiple layers. Multi-layer collars can have layers that are formed from different ECMs and/or contain different additives.
13. In yet another embodiment, a system (kit) that includes at least one extracellular matrix, a device to apply the ECM to the implant and a protocol for using the kit to coat the implant with at least one layer of ECM as well as a specific drying and hydrating method described.
14. Cannulas used herein can be employed in conjunction with an infusion device, such as an insulin pump. An infusion pump infuses fluids, medication or nutrients into a patient's circulatory system. It is generally used in subcutaneous, intravenously, arterial and epidural infusions.
15. In a further embodiment, a surgical mesh is coated with one or more layers of ECM, with the mesh being dehydrated after each layer is applied. Additives can be incorporated into the ECM, including protein and non-protein substances such as factors (drug), cytokines, antibodies.

A Third Set of Disclosed Method Embodiments

In yet another embodiment, a method of making (coating) a cannula is described in which basement membrane in the form of a liquid or gel is applied to a cannula and dehydrated at ambient temperature. The basement membrane is later rehydrated before or after the cannula is inserted in a user.

In a further embodiment, the method of making a cannula or collar is described in which basement membrane in the form of a liquid is applied to a sensor at 4° C. and dehydrated at a temperature in the range of 4 Deg. C. The basement membrane is later rehydrated after the cannula or collar is inserted in a user.

Another embodiment is a method of making a cannula or collar in which a coating is applied before as a coating or "insertion pocket" and/or after insertion of the cannula or collar in a user, which promotes lymphangiogenesis. The coating comprises at least one extracellular matrix and at least lymphangiogenesis factor such as VEGF-C.

A further embodiment is a method of making a surgical mesh comprising coating the mesh with one or more layers of ECM, with or without the incorporation of additive in the ECM.

System Components

Figure 1:
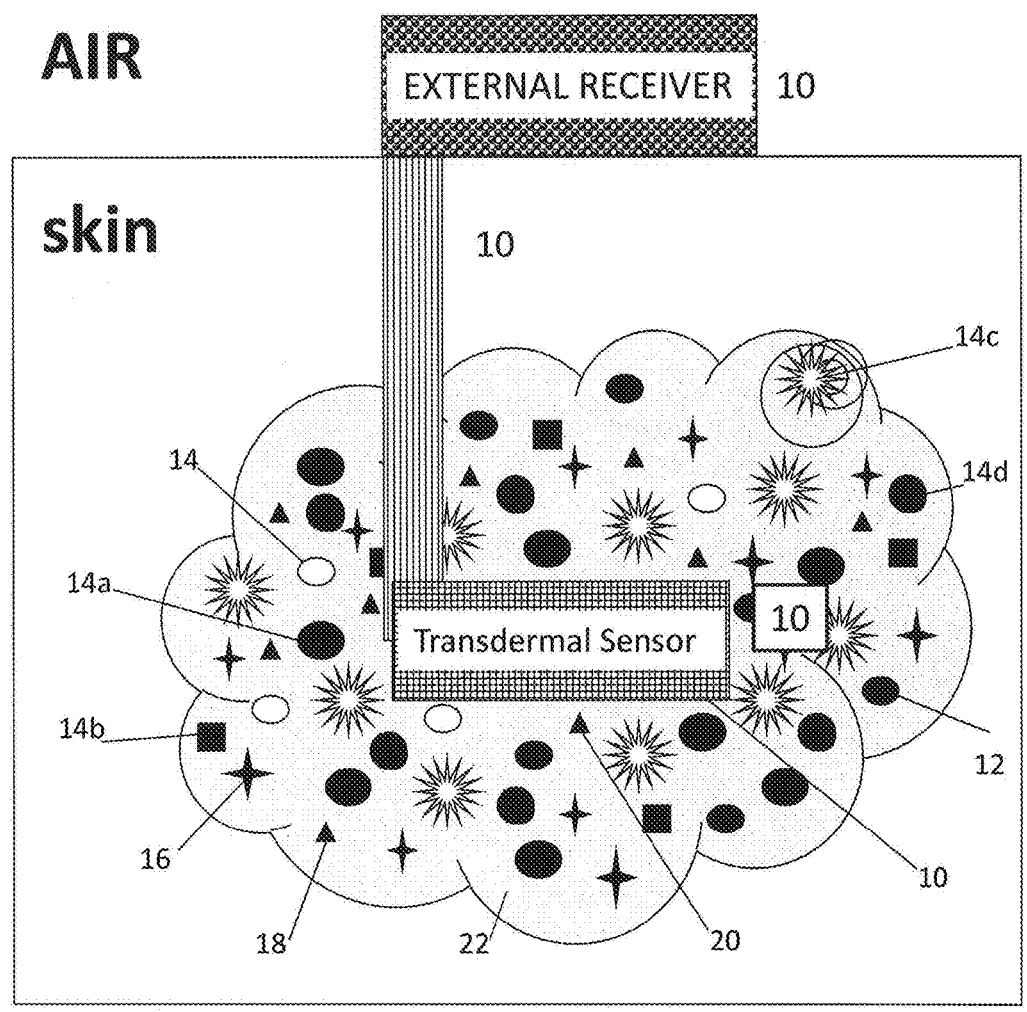
FIG. 1 shows a transdermal sensor according to a first embodiment.
Figure 2:
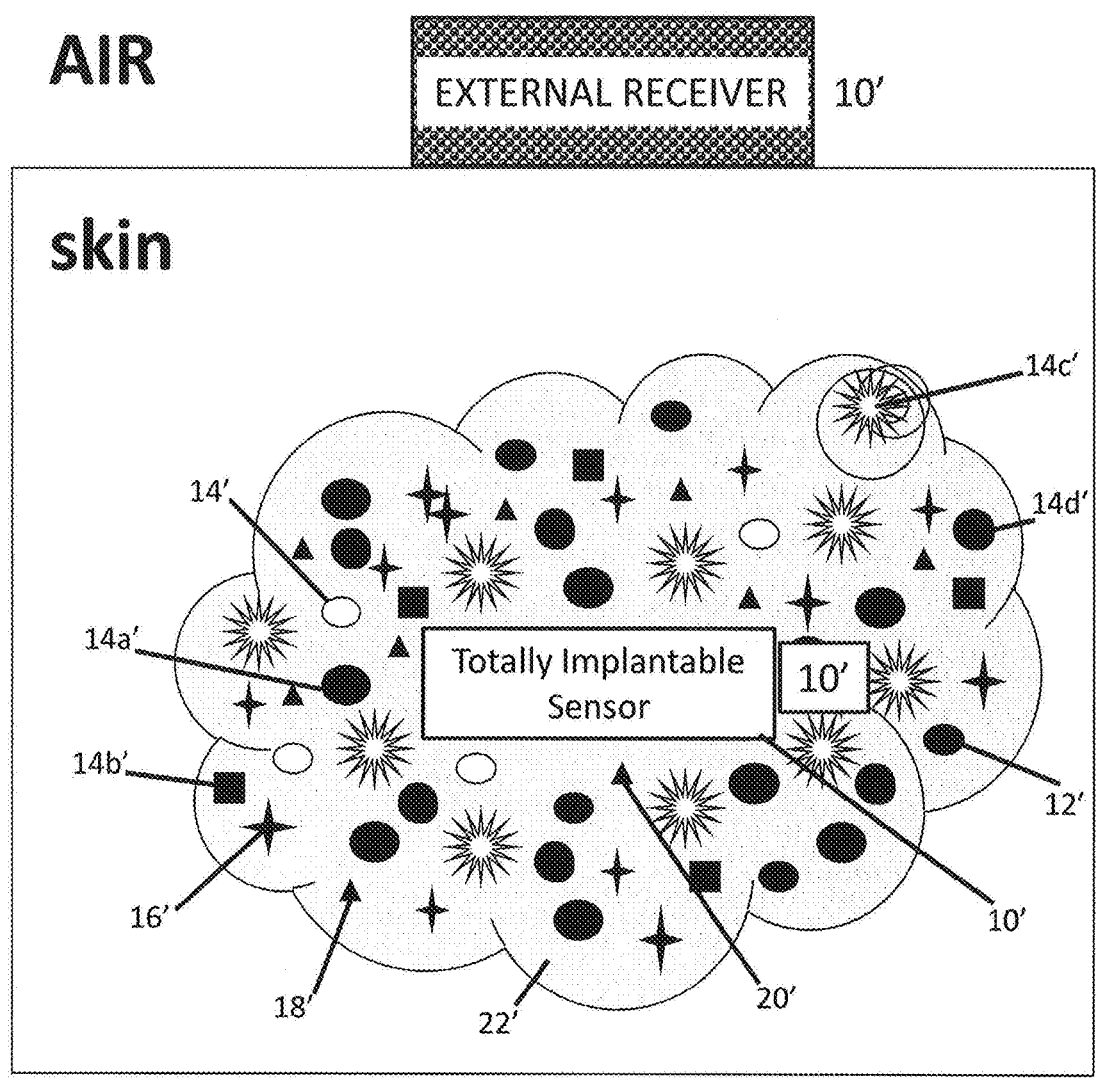
FIG. 2 shows a totally implantable sensor according to a second embodiment.

The components of the systems described herein include Implantable Devices, Matrix Material, and in some cases, Cells and Factors, etc. inserted into the matrix. Each of these components is described below. In FIG. 1, the sensor system 8 includes a sensor 10 and a tissue system 12 that includes a matrix material 22 and optionally includes cells and/or factors supported in the matrix material 22. In FIG. 2, the sensor system 8' includes a sensor 10' and a tissue system 12' that includes a matrix material 22' and optionally includes cells and/or factors supported in the matrix material 22'.

Types of Implantable Devices

The collars can be used in conjunction with implantable sensors, as well as other implants that have an elongated, thin configuration. Transcutaneous and fully implantable sensors can be used in the embodiments described herein. A transcutaneous sensor is shown in FIG. 1 and a fully implantable sensor is shown in FIG. 2. The sensors may be chemical sensor and/or biosensors. Glucose sensors, including amperometric glucose sensors, for example, glucose oxidase sensors, fluorescence based glucose sensor can be used. Other types of sensors included herein are implantable sensors for monitoring conditions such as blood pH, ion concentration, metabolite levels, clinical chemistry analyses, oxygen concentration, carbon dioxide concentration, and pressure. It should be understood that the implant devices may become embedded, or otherwise integrated, into the biological system.

Sensors typically are made from the following materials: metals, including silver and platinum, and coatings which typically are thermoplastics and thermosets, including polyurethane and polytetrafluoroethylene, and composites. A non-limiting example of a commercially used sensor coating is a high-molecular-weight poly (vinylpyridine)-poly(ethylene glycol) copolymer cross-linked using a trifunctional short chain epoxide. Particular materials used in implants of various types are nylon, for example Nafion®, which is a sulfonated tetrafluoroethylene based fluoropolymer-copolymer, and silicone, which has frequently been used in implants and generally has minimal reactivity in mammalian tissues. Reactivity of nylon and silicone materials was evaluated in the ex ova chicken model, as is described in U.S. application Ser. No. 10/578,171, the contents of which are incorporated herein by reference in their entirety. PTFE materials such as Teflon have been used in sensors, often as a coating for a metal wire (see U.S. application Ser. No. 10/578,171).

In embodiments, other devices may be used in addition to the sensor 10, or may replace the sensor 10. For example: bioreactors for liver, kidney or other organ support systems; catheters; artificial arteries; artificial organs; tissue fragment-containing devices; cell-containing devices; ligament replacements; bone replacements; coronary pacemakers; lap-bands, monitors; artificial larynxes; prostheses; brain stimulators; bladder pacemakers; shunts; stents; tubes; defibrillators; cardioverters; heart valves; joint replacements; fixation devices; ocular implants; cochlear implants; breast implants; neurostimulators; bone growth stimulators; vascular grafts; muscle stimulators; left ventricular assist devices; pressure sensors; vagus nerve stimulators; drug delivery systems; sutures and staples. In addition the devices may include implants. For example: prostheses, such as joint replacements; artificial tendons and ligaments; dental implants; blood vessel prostheses; heart valves; cochlear replacements; intraocular lens; mammary prostheses; penile and testicular prostheses; tracheal, laryngeal, and esophageal replacement devices; artificial organs such as heart, liver, pancreas, kidney, and parathyroid; repair materials and devices such as bone cements, bone defect repairs, bone plates for fracture fixation; heart valves; catheters; nerve regeneration channels; corneal bandages; skin repair templates; scaffolds for tissue repair and regeneration including surgical meshes; and devices such as pacemakers, implantable drug delivery systems (e.g., for drugs, human growth hormone, insulin, bone growth factors, and other hormones). Furthermore, the device may include implantable drug delivery systems such as those disclosed in U.S. Pat. Nos. 3,773,919, 4,155,992, 4,379,138, 4,130,639, 4,900,556, 4,186,189, 5,593,697, and 5,342,622 which are incorporated in their entirety by reference herein. Implantable sensors for monitoring conditions such as blood pH, ion concentration, metabolite levels, clinical chemistry analyses, oxygen concentration, carbon dioxide concentration, pressure, and glucose levels are known. Blood glucose levels, for example, may be monitored using optical sensors and electrochemical sensors. It should be understood that the implant devices may become embedded, or otherwise integrated, into the biological system.

Cannulas described herein can be employed in conjunction with an infusions device, such as an insulin pump. These cannulas and catheters are made of a variety of materials plastics and metals and are used to infuse drugs, liquids such as saline, nutrients, antibiotics.

Surgical meshes described herein can be made from a variety of biocompatible materials, including but not limited to cellulose, polypropylene, polyesters, and polyethylene terephthalate (PET). Surgical meshes can also be produced from acellularized human or animal tissues.

Figure 26:
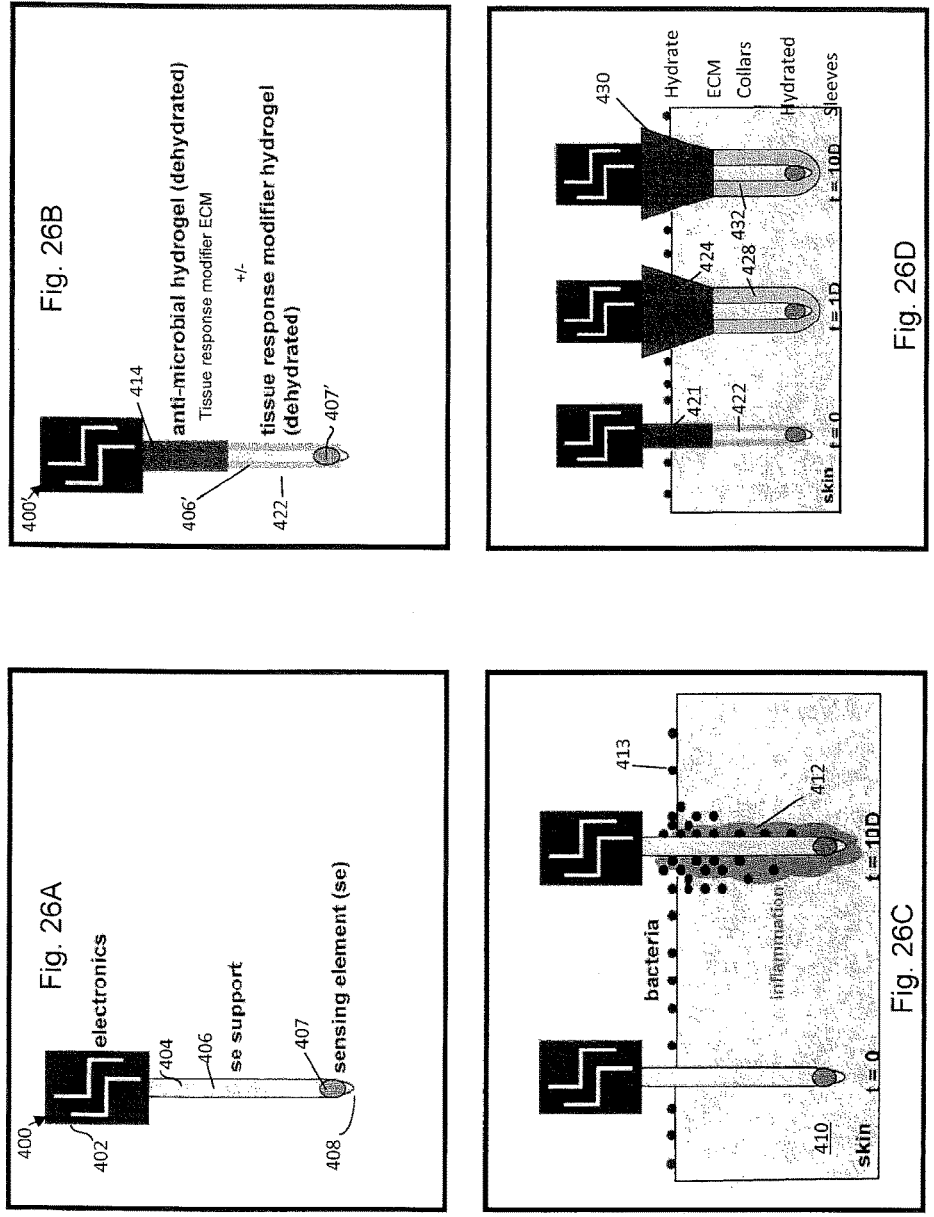
FIG. 26 shows an embodiment of dry and hydrated ECM based collars and sleeves (+/−anti-microbial and or TRMs) incorporated into the ECM on a glucose sensor.

FIG. 26C-26D show a sensor assembly with a collar. The sensor assembly 400 includes electronics 402, a sensing element support 404 with a sensing element 406 at the tip. The sensing element support 406 has an antimicrobial collar 408 configured to be positioned on both sides of the point at which the support enters the tissue 410. A coating 412 containing a tissue response modifier, such as those described above is disposed between the collar 408 and the sensing element 406. This configuration prevents inflammation that otherwise may occur, as shown in FIG. 26B, within the tissue around the sensor and support. While the coating 412 usually is rehydrated after implantation to minimize discomfort to the patient, the coating 412 also can be rehydrated before implantation. In embodiments, the coating can be applied immediately before assembly, in which case initial dehydration would not be required.

In embodiments, the implantable device is a surgical mesh of the type used for reconstructive surgery, such as hernia repair.

Matrix Material

Referring to FIGS. 1-2, the artificial tissue system (ATS) 12 further includes a matrix material 22. The matrix material 22 may be natural and/or synthetic materials. For example, the matrix material 22 may include biological matrices, such as naturally occurring matrices that occur in viable organisms (in vivo), and tissues including ex vivo tissues, as well as in association with cells maintained in vitro, or combinations thereof. One characteristic of the matrix material 22 is the ability to provide a three dimensional structure to the ATS 12. This three dimensional structure provides a volume of space that allows for biological contact wherein various components of the ATS 12, sensor 10, and surrounding tissues can biologically associate with one another. For example, the matrix material may provide the necessary framework in which various cells can be secured as well as providing for the movement of nutrients, chemicals, and other bioactive agents to, from, and/or between cells, tissues, and/or an implant device, such as, the sensor 10. In addition, the matrix material 22 is in biological contact with portions of the implant device and the surrounding biological system, if present. It should be understood that the biological contact includes, among other things, chemical, liquid, gas, and/or mechanical contact. For example, cellular tissue of the biological system may intrude, or otherwise extend physically into the volume of space occupied by the matrix material. This cellular tissue may also be in physical, chemical, and/or fluid contact with the cells, portions of the implant device, such as the sensor 10, genetic elements 16, cell response modifiers (CRM) 18, and/or tissue response modifiers (TRM) 20. The genetic elements 16 include, for example, agent(s) that directly cause the temporary or permanent change of the genetic composition or expression of a cell or tissue, or indirectly cause the temporary or permanent change of the genetic composition or expression of a cell or tissue. For example, single or double strand DNA, single or double strand RNA, plasmids, viral vectors, and/or DNA or RNA viral vectors. In addition, it should be understood that the ATS may be formed into, for example, any biologically relevant shape, for example, a tube, sponge, sphere, strand, coiled strand, capillary network, film, fiber, mesh, and/or sheet.

In one embodiment, the matrix material 22 may include: basement membranes, for example Matrigel™; fibrin clots, including plasma derived clots; collagens, for example, fibrillar collagens (types I, II, III, V and IX collagen); basement membrane collagen, such as type IV collagen; other collagens (types VI, VII, IX, XVII, XV and XVIII collagen); fibronectin; laminin; proteoglycans; glycoproteins; glycoaminoglycans; elastins; hyaluronan; adhesive glycoproteins; mucins; and polysaccharides. In some cases, certain factors can be included with the matrix material 22 to advantageously enhance the characteristics of the matrix material 22 and/or its production. For example, factors that can be included are: TGF-beta; FGF; angiotensin II; Insulin-like growth factor; and ascorbic acid.

In one embodiment, the matrix material 22 is composed of a solubilized basement membrane preparation such as Matrigel™ as supplied from BD Biosciences. The solubilized basement membrane, like fibrin, is a naturally occurring protein matrix/bio-hydrogel, that has a wide variety of binding sites for cells and factors. These factors may include growth factors and cytokines. For example, the solubilized basement membrane may include laminin, collagen, including collagen IV, heparin sulphate proteoglycans, and entactin. Solubilized basement membrane has been used extensively as a cell matrix/depot in a wide variety of in vitro and in vivo studies particularly in the area of tumor cell biology and angiogenesis.

In one embodiment the solubilized basement membrane is a liquid at 4° C. but becomes a solid bio-hydrogel when warmed to 37° C. (or less). This ability to convert solubilized basement membrane from a liquid to a solid by simply raising the temperature, allows for a wide variety of strategies for entrapping genetically engineered cells, factors, proteins and genes. It should be understood that the terms entrap, entraps, entrapped, entrapping, and the like are intended to include for the purpose of this application the concept that the matrix material 22 provides a mechanical association with the biological cells and/or that the matrix material 22 provides specific binding sites for the biological cells. For example, specific binding sites which include receptor and/or adhesion sites.

As previously discussed, Matrigel is an isolated basement membrane obtained for cells cultured in vitro, which has been used in a wide variety of in vivo and in vitro studies of cell attachment, cell growth and angiogenesis. Like fibrin, Matrigel™ is a naturally occurring matrix derived from basement membrane, that has a wide variety of binding sites for cells and factors (including growth factors and cytokines). Matrigel™ has been used extensively as a cell matrix/depot in a wide variety of in vitro and in vivo studies particularly in the area of tumor cell biology and angiogenesis. Matrigel™ is a liquid at 4° C. but becomes a solid biological matrix when warmed to 37° C. This ability to convert Matrigel™ from a liquid to a solid by simply raising the temperature, allows for a wide variety of strategies for entrapping genetically engineered cells, factors proteins and genes. Matrigel™ and other isolated basement membrane materials possess the characteristics to serve as a tissue interactive biological matrix for the ATS.

According to the literature, basement membrane contains laminin, type IV collagen, and a heparin sulfate proteoglycan (perlecan). BD Matrigel™ Matrix is a reconstituted basement membrane preparation that is extracted from the Engelbreth-Holm-Sawrm (EHS) mouse sarcoma, a tumor rich in extracellular matrix proteins (extracted from cell cultures in vitro). Once isolated, the material has approximately 56-61%, or 60%, laminin, 30-31% collagen IV and 7-8% entactin. Matrigel™ matrix also contains heparin sulfate proteoglycan, TGF-Beta, epidermal growth factor, insulin-like growth factor, fibroblast growth factor and tissue plasminogen activator. The growth factors occur naturally in the EHS tumor. When frozen, Matrigel™ matrix is a solid. When allowed to thaw in a refrigerator (4° C.) and when stored in a refrigerator, Matrigel™ matrix is a liquid. Matrigel™ matrix will start to form a gel above 10 Deg. C. and will gel rapidly at 22-35 Deg. C. Matrigel™ matrix will form a gel if it is diluted up to a concentration of 3 mg/ml.

In embodiments, the basement membrane is crosslinked with crosslinking agent that forms covalent bonds between components of the basement membrane and is biocompatible with the surrounding tissue in the amount in which it is used. In embodiments, the crosslinking agent comprises a di-aldehyde.

When the crosslinking agent is glutaraldehyde, it typically is used in quantities of 0.1-1% W/W, or 0.1-0.6% W/W, or 0.2-0.2% W/W. In embodiments, when the implantable device is placed in a liquid glutaraldehyde solution, the exposure time ranges from 3 to 10 minutes.

Cells, Genetic Elements, Cell Response Modifiers, Tissue Response Modifiers, Genetic Elements and Factors When cells are incorporated into the basement membrane, the cells can include biological cells 14, 14', genetically engineered cells 14a, 14a', artificial cells 14b, 14b', stem cells 14c, 14c', and/or support cells 14d, 14d'. The support cells 14d, 14d' generally are included with other cells and serve to provide nutrients, factors, physical surfaces, or other required or desirable products to the cells they support. The ATS may also include genetic elements 16, 16', cell response modifiers (CRM) 18, 18', and/or tissue response modifiers (TRM) 20, 20'.

In one embodiment, the cells include eukaryotic cells; prokaryotic cells; vertebrates cells; invertebrates cells; normal cells; cancer cells; mutant cells; engineered cells, such as genetically altered cells, chemically altered cells, transgenic cells, hybrid cells (hybridomas); artificial cells; and stem cells, such as embryonic stem cells, adult stem cells, stem cell lines, engineered stem cells. The cells may be classified as categories of functional cells, for example, inflammatory cells, immune cells, tissue cells, cells which control wound healing, cells which control fibrosis, cells which control tissue regeneration, regulatory cells, cytokine producing cells, growth factor producing cells, matrix producing cells, vascular cells, connective tissue cells, bone producing cells and bone, blood cells. The cells may also be classified as types of cells, for example, endothelial cells, fibroblasts, epithelial cells, muscle cells, fat cells, lymphocytes, macrophages, mast cells, polymorphonuclear leukocytes, red blood cells, neurologic cells, osteoblasts, osteoclasts, nerve cells, fat cells, brain cells. Other categories of cells may be used and include, but are not limited to, autologous cells, heterologous cells, allogenic cells, xenogenic cells, autologous cells, (relative to the host), heterologous cells (relative to the host), allogenic cells (relative to the host tissue), xenogenic cells (relative to the host tissue). It should be understood that the cells may be used in combination with one another such that a cellular component is formed. The cellular component may include one or more cellular communities wherein the communities interact on, for example, symbiotic, commensal, saprophytic, inhibitory and/or other biologically relevant association. For example, engineered and non-engineered cells may be used in combination to provide advantageous biologic contact with one another and with a biologic system with which they are associated, for example a living mammal biologic system.

In one embodiment, cell of different categories and/or types may be combined in the matrix material 22. For example, functional cells may be used which regulate the function of other cells within the matrix material 22. This may include cells that produce cytokines and growth factors; cells that regulate the function of the cells within the host tissue; cells that include matrix producing cells within the host tissue; cells that produce cytokines and growth factors which control cells in the host tissues; cells that controls inflammation within the ATS; cells that control wound healing within the ATS; cells that control fibrosis within the ATS; cells that control neovascularization within the ATS; cells that control cell proliferation within the ATS; cells that control immune responses within the ATS; cells that include cells that control cell death within the ATS; cells that includes cells that control inflammation within the tissues; cells that control wound healing within the tissues; cells that control fibrosis within the tissues; cells that control neovascularization within the tissues; cells that control cell proliferation within the tissues; cells that control immune responses within the tissues; cells that control cell death within the tissues; cells that produces cytokines; cells that produce growth factors; cells that control vessel formation and regression; cells that produce genetically altered proteins and peptides; and cells that overproduce proteins and/or peptides.

Sources of biological cells include cells directly isolated from in vivo sources; cells obtained from embryonic tissues, neonatal tissues, juvenile or adult tissues; cells obtained from in vitro sources; cells obtained from primary cell culture sources; cells obtained from secondary cell culture sources; and cells obtained from continuous cell lines.

In one embodiment, the CRM 18 and/or TRM 20 are differentiated based on their biologic effect. For example, "cell response modifiers" (CRM) 18, as used herein, include agents that control the structure and or function of cells in vitro and or in vivo, whereas, "tissue response modifiers" (TRM) 20 as used herein, include agents that control the structure and or function of tissues in vivo and or ex vivo. The CRM 18 may include cells genetically engineered and non-genetically engineered: biological cells, synthetic cells, regulatory cells, tissue support cells, mutant cells, artificial cells, genetically altered cells, chemically altered cells, and/or stem cells. The CRM 18 may control cellular proliferation; cell injury; cell death; cell metabolism; cell protein synthesis; cell gene expression; and/or agents that control the structure and/or function of cells derived from any in vitro or in vivo source.

In one embodiment, the categories or types of cells whose structure and or function is controlled by CRM 18, include cells derived from embryonic, neonatal, juvenile and or adult cells. In addition, cells that may be controlled by CRM 18 include biological cells, eukaryotic cells, prokaryotic cells, vertebrates cells, invertebrates cells, normal cells, cancer cells, mutant cells, engineered cells, artificial cells, stem cells, and/or hybrid cells. In addition, cells controlled by CRM 18, include, for example, endothelial cells, fibroblasts, epithelial cells, muscle cells, fat cells, lymphocytes, macrophages, mast cells, polymorphonuclear leukocytes, red blood cells, neurologic cells, osteoblasts, osteoclasts, nerve, fat cells, brain cells, bone cells, tissue derived stem cells, blood derived stem cells, bone derived stem cells.

In one embodiment, the CRM 18, include agents that, for example, control cell homeostasis by controlling cell functions such as cell activation, cell proliferation, cell metabolism, cell death (including apoptosis), cell differentiation and maturation, cell size, cell composition.

In one embodiment, the TRM includes, for example, agent(s) that control tissue growth; tissue differentiation; tissue injury; innate immune responses; acquired immune responses; humoral immune responses; cell mediated immune responses; inflammation; acute inflammation; chronic inflammation; wound healing; regeneration; tissue repair; neovascularization; bone destruction; bone injury, repair and or regeneration; connective tissue destructions; controls connective tissue injury, repair and regeneration; fat tissue injury, repair and or regeneration; neurologic tissue injury, repair and or regeneration; and/or responses using TRM 20. The TRM 20 may include: cell to cell protein transporter molecules; antibodies; proteins, modified proteins and/or recombinant protein; chemicals; drugs; genetic elements; recombinant DNA; RNAs, including siRNA; altered RNAs; genetically altered RNAs; chemically altered RNAs; DNA; altered DNAs; carbohydrates; lipids and fatty acids; radiation energy; magnetic energy; viruses; single or double strained DNA; and/or single or double strained RNA.

The TRM 20 may be used in combination, for example, the TRM 20 may include: TRM that controls tissue injury and a second TRM that controls inflammation; TRM that controls inflammation and a second TRM that controls fibrosis; TRM that controls inflammation and a second TRM that controls neovascularization; TRM that controls inflammation and a second TRM that controls tissue regeneration; TRM that controls cell injury and a second TRM that controls inflammation; TRM that controls cell death and a second TRM that controls inflammation; TRM that controls inflammation and a second TRM that controls fibrosis; TRM that controls inflammation and a second TRM that controls neovascularization; TRM that controls fibrosis and a second TRM that controls neovascularization; and/or TRM that controls inflammation and a second TRM that controls tissue regeneration.

The TRM 20 may, for example, in one embodiment include the agents 2-(3-benzophenyl)propionic acid, 9-alpha-fluoro-16-alpha-methylprednisolone, methyl prednisone, fluoroxyprednisolone, 17-hydroxycorticosterone, cyclosporin, (+)-6-methoxy-.alpha.-methyl-2-naphthalene acetic acid, 4-isobutyl-.alpha.-methylphenyl acetic acid, Mitomicyin C, Acetaminophen, Dexamethasone, Diphenyhdramine, Hydrochloride, Cromolyn, 3-(1H-Tetrazol-5-yl)-9H-thiol-xanthene-9-one 10,10-dioxide monohydrate, H1 and H2 histamine antagonists (H1 antagonists: mepytramine or triprolidine) transforming growth factor alpha, anti-transforming growth factor beta, epidermal growth factor, vascular endothelial growth factor, anti-transforming growth factor beta antibody, anti-fibroblast antibody, anti-transforming growth factor beta receptor antibody, arginine-glycine-aspartic acid, REDV, or a combination thereof.

Categories of tissues whose normal structure and or function is controlled by TRM, include, for example, biological tissues of vertebrates, invertebrates; normal tissue; injured tissue; regenerating tissue; repairing tissue; cancer tissue; mutant tissue; engineered tissue; artificial tissue; stem cell tissues; hybrid tissues; endothelial tissue; fibroblasts; epithelial tissue; muscle tissue; fat tissue; lymphocytes; macrophages; mast tissue; polymorphonuclear leukocytes; red blood cells, soft tissue; neurologic tissue; osteoblasts; osteoclasts; nerve; brain tissue; bone tissue; tissue derived stem tissue; blood derived stem tissue; and/or bone derived stem tissue.

Categories of tissues whose structure or function is controlled by TRM ex vivo include, for example, tissues originally derived from embryonic, neonatal, juvenile and/or adult tissues. Categories of tissues whose structure or function is controlled by TRM in vivo and or ex vivo include, for example, embryonic tissues, neonatal tissues, juvenile or adult skin. Injured tissues controlled in vivo and or ex vivo by TRM, include, for example, normal embryonic tissues, neonatal tissues, juvenile or adult skin. Tissues controlled in vivo and or ex vivo by TRM, include, for example, include embryonic tissues, neonatal tissues, juvenile or adult soft tissue, hard tissue, e.g. bone), skin, cardiac system, pulmonary, hepatic, gastrointestinal tract, biliary tract, urinary tract, genital tract, vision, neurologic or endocrine systems, blood vessels, bones, joints, tendons, nerves, muscles, the head, the neck, or any organ system or combinations thereof.

In one embodiment, factors that are used to control vascular endothelial cell function in vitro (i.e. cell response modifiers 18) also may induce or suppress new blood vessel formation in vivo thus under the right circumstances they are also tissue response modifiers 20. For example, these factors may include: Vascular Endothelial Growth Factor (VEGF); Fibroblast Growth Factor (FGF); Interleukin-8 (IL-8); Angiogenin; Angiotropin; Epidermal Growth Factor (EGF); Platelet Derived Endothelial Cell Growth Factor; Transforming Growth Factor α (TGF-α); Transforming Growth Factor β (TGF-β); Nitric Oxide; Thrombospondin; Angiostatin; and Endostatin.

In one embodiment, cell response modifiers 18 are used, but because they also operate to control inflammation and immune responses as well as development in vivo they are also examples of cell response modifiers that can act in vivo as tissue response modifiers 20. For example, cytokines and growth factors included in this operative definition include: TH1/TH2 Interleukins (IL-2, IL-4, IL-7, IL-9, IL-10, IL-12, IL-13, IL-15, IL-16, IL-17); the IL-1 family (IL-1-alpha, IL-1Ra, IL-18, IL-1-beta); the TNF family, for example TNF Ligand and TNF/NGF Receptor Families, TNFalpha, Lymphotoxin alpha and beta, Fas Ligand, CD40 Ligand, CD30 Ligand, CD27 Ligand, RANK Ligand Apo2L/TRAIL; the IL-6 family, for example, IL-6 Ligand and Receptor Family, IL-6, IL-11, Oncostatin M, CT-1; macrophage activation, such as, IFNalpha, IFN beta, and IFNomega Ligands, IFNgamma, Osteopontin, MIF; TGF beta, BMP Family, PDGF, VEGF, Poxvirus Vascular Endothelial Growth Factor (VEGF) Homologs of Orf Virus, Angiostatin, Activin, Endostatin, Methoxyestradiol, Poxvirus Growth Factors Related to EGF; IL-3, IL-5, Stem Cell Factor, GM-CSF CSF-1, G-CSF, Erythropoietin, Thrombopoietin; MGSA/GRO, ENA-78, IL-8, H. GCP-2, A. CTAP-III, betaTG, and NAP-2, Platelet Factor 4, IP-10 MIG, SDF-1, BLR1 Ligand/BCA-1/BLC, 9E3/cCAF; MCP-1, MCP-2, MCP-3, MCP-4, and MCP-5 RANTES, 1-309, MIP-alpha, MIP-beta, Eotaxin, PARC, Eotaxin 2, MIP-gamma/MRP-2, Mu C10, Leukotactin 1, CKbeta8-, B. HCC-1, SLC (6CKine), ELC, H TECK/CCL25, CC Chemokine of Molluscum Contagiosum Virus, Lymphotactin, Fractalkine, Poxvirus Secreted Complement Control Proteins; IL-2 Family Receptors, IL-2 Receptor, IL-4 Receptor, IL-7 Receptor, IL-9 Receptor, IL-10 Receptor, IL-12 Receptor, IL-13 Receptor, IL-15 Receptor, IL-16 Receptor (CD4), IL-17 Receptor, Prolactin Receptor; IL-1 Family Receptors, such as, IL-1 Receptor Family, IL-1 Receptor Type I, Poxvirus IL-1 beta Receptor Homologs, IL-18 Receptor, IL-1 Receptor Type II; TNF Receptors, Poxvirus TNF Receptor Homologs, Lymphotoxin beta Receptor, Fas, CD40, CD30, 4-1BB, RANK, Osteoprotegerin, CD27, HVEM, DR4, DR5, DcR1, DcR2, DcR3, Ox40, GIT Receptor; IL-6 Receptor; IL-11 Receptor, OSM Receptor, CT-1 Receptor; IFNgamma Receptor, Poxvirus IFNgamma Receptor Homologs, IFN c beta Receptor, Poxvirus IFN c beta Receptor Homologs, Osteopontin Receptor, TGF beta Receptors, BMP Receptor, Hematopoietic Receptors, for example the Hematopoietic Receptor Family of IL-3 Receptor, IL-5 Receptor, SCF Receptor, GM-CSF Receptor, G-CSF Receptor, TPO Receptor; CXC Chemokine Receptors, such as, CXCR1 and CXCR2, CXCR3, CXCR4, CXCR5, R. CC, C, and CX3C; CC Chemokine Receptors, such as, CCR1, CCR2, CCR3, CCR4, CCR5, CCR6, CCR7, CCR8, D6, ECRF3, Poxvirus Membrane-bound G Protein-coupled Receptor Homologs, US28, Kaposi's Sarcoma-associated Herpesvirus GPCR, DARC, CX3CR1, Poxvirus Secreted Chemokine-binding Proteins, CCR9, XCR1; and Miscellaneous non-Cytokine Proinflammatory Factor Receptor, such as C5a Receptor, C3a Receptor, PAF Receptors, fMLP Receptors, Opioid mu, delta, and kappaReceptors for Endorphins, Lipoxin A4 Receptor, ACTH Receptor, BLTR: the Leukotriene B4 Receptor, PACAP and VIP Receptors, Lysophospholipid Growth Factor Receptors.

In one embodiment stem or progenitor cells 14c are included in the ATS. These stem or progenitor cells may be included in a matrix material 22, which is selected based on the origin of the stem or progenitor cells. For example, expansion of undifferentiated stem cells, in vitro, may be accomplished with a gelatin matrix material; expansion of nestin+neural progenitor cells may be accomplished with laminin, RA, Survival of embryonic stem cell derived motor neurons with basement membrane, and endothelial cells with collagen IV. If, for example, the stem or progenitor cells are of a bone marrow origin of the MSC, MAPC, or HSC type, then fibronectin and or basement membranes may be used. For example, expansion in vitro of undifferentiated MAPCs with fibronectin; osteoblasts with fibronectin; endothelial cells with fibronectin; and hepatocyte-like cells: basement membranes. If, for example, the stem or progenitor cells are of an adult tissue origin of the hepatic oval cell, NSC/NPC, adipose stem cell, or MDSC type, then fibronectin, laminin and/or collagen may be used. For example, expansion of undifferentiated oval cells with fibronectin; hepatocyte with fibronectin; pancreatic islet with fibronectin; neuron, glial cells with fibronectin, laminin; expansion of MDSCs with collagen, and osteoblast with collagen.

In one embodiment, several growth factors or cytokines may be used as, for example, CRM 18 to promote stem or progenitor cell proliferation and differentiation in vitro. For example, if the stem or progenitor cells are embryonic stem cells, then expansion of undifferentiated ES cells can be accomplished with LIF; pancreatic endocrine progenitor with bFGF; pancreatic islet with bFGF; expansion of Nestin+neural progenitors with bFGF; RASurvival of ES-derived motor neurons with BDNF, NT-3, CNTF, GDNF; glial progenitor cells with bFGF, PDGF-AA; adipocyte13RAChondrocyte with BMP-2, BMP-4; dendritic cells: GM-CSF, IL-3; and endothelial cells with VEGF. If the stem or progenitor cells are derived from bone marrow and are of the MSC, MAPC, or HSC types, then, for example, osteoblast may be utilized with BMP-2, bFGF; chondrocyte with TGF-ß3; neuron, glial cells with EGF, BDNF; expansion of undifferentiated MAPCs with EGF, PDGF-BB; chondrocyte with TGF-ß1; endothelial cells with VEGF; hepatocyte-like cells with FGF-4, HGF; and platelets, red/white blood cells with IL-3, IL-6, G-CSF. If the stem or progenitor cells are derived from adult tissues and are of the Hepatic oval cell, NSC/NPC, Adipose stem cell or MDSC types, then, for example, expansion of undifferentiated oval cells can be accomplished with SCF, Flt-3 ligand, IL-3, LIF; hepatocyte with HGF, EGF; pancreatic islet with SCF, Flt-3 ligand, IL-3; expansion of NPCs with bFGF, EGF, LIF; neuron, glial cells with bFGF, EGF, PDGF-AA, PDGF-AB, PDGF-BB, NT-4, CNTF; osteoblast with TGF-ß1; expansion of MDSCs with IGF-1, EGF, SCF, FGF2; and osteoblast: BMP-2.

In one embodiment stem or progenitor cells 14c are promoted utilizing other factors as, for example, TRM 20. For example, if the stem or progenitor cells are embryonic stem cells, then pancreatic islet cells can be utilized with nicotinamide; expansion of Nestin+neural progenitors can be accomplished with poly-ornithine; neurons with poly-ornithine, RA; Adipocytes with RA; and osteoblasts with RA, dexamethasone, ascorbate, ß-glycerol phosphate. If the stem or progenitor cells are derived from bone marrow and are of the MSC, MAPC, or HSC types, then, for example, osteoblasts with dexamethasone, ascorbate, ß-glycerol phosphate; chondrocytes with dexamethasone; neuron, glial cells with RA; adipocytes with dexamethasone, insulin, indomethacin, 1-methyl-3-isobutylxanthine; expansion of undifferentiated MAPCs with 2% FBS; osteoblasts with dexamethasone, ascorbate, ß-glycerol phosphate; platelets, red/white blood cells with erythropoietin, thrombopoietin. If the stem or progenitor cells are derived from adult tissues and are of the Hepatic oval cell, NSC/NPC, Adipose stem cell or MDSC types, then, for example, pancreatic islet cells can be utilized with nicotinamide; osteoblasts with Dexamethasone, ascorbate, ß-glycerol phosphate; chondrocytes with insulin, ascorbate; and adipocytes with dexamethasone, insulin, indomethacin, 1-methyl-3-isobutylxanthine.

FIG. 24 provides a list of angiogenic factors. VEGF-A induces both blood vessels and lymphatic vessels. VEGF-C and VEGF-D induce a predominance of lymphatic vessel and some blood vessels.

Method of Applying Coatings

Figure 3:
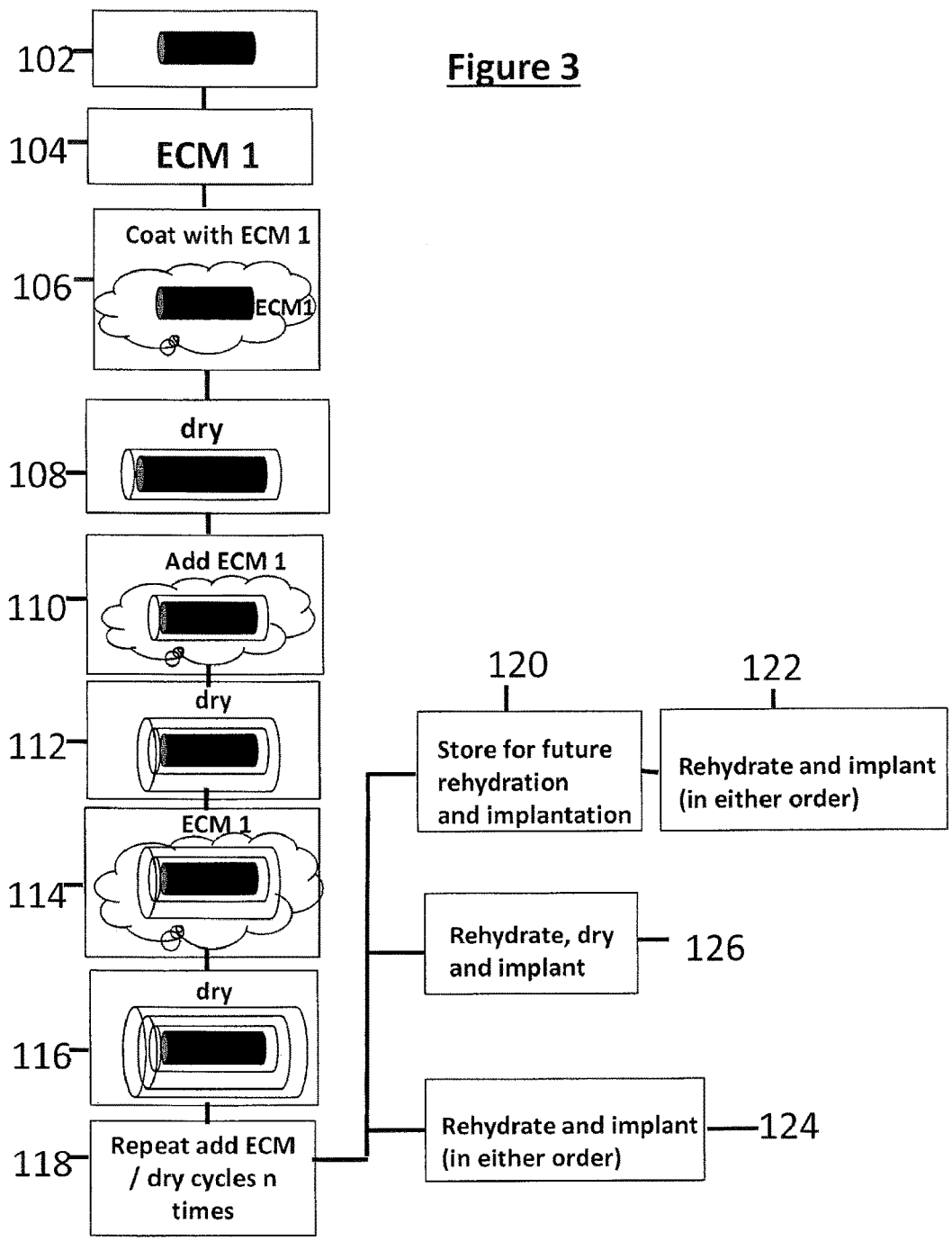
FIG. 3 is a flow chart showing a method according to one embodiment described herein.

In the embodiments shown in FIG. 3, as well as embodiments described below and shown in other figures, multiple layers of a single type of coating optionally can be applied, or a single coating can be used. The overall method of coating is designated as 100. While the method is described in connection with sensors, the same method applies to cannulas and collars (that are not themselves made of ECM), and also to surgical mesh.

In other embodiments, multiple layers of different ECMs can be applied to a device. The various layers can have different cells and/or factors incorporated therein. In the embodiment shown in FIG. 3, multiple layers of a single type of coating are applied. The overall method of coating is designated as 100. Referring to FIG. 3, a device is obtained at 102 and an extracellular matrix material to be used as a coating material is obtained at 104. The coating is configured in liquid or gel form based on the temperature of the coating material (Matrigel™ matrix will start to form a gel at or above 10 Deg. C. and will gel rapidly at 22-35 Deg. C.). The device is partially or fully coated with the coating material at 106 by dipping, spraying, brushing or another suitable technique. The coating is dried at 108. Drying can take place at room temperature, at elevated temperature, or at a temperature below room temperature including 4 deg. C. The coatings can be dried passively at room temperature or above through the uses of fans/blowers or heating devices at room temperature or above (gel) or 4 deg. C. (liquid).

Drying the liquid or gelatinous basement membrane at different temperatures likely would change the structures and orientation of the proteins and factors in the basement membrane (for example cross linking occurs as a result of drying). For a coating material such as solubilized basement membrane, which typically is a liquid at 4 degrees centigrade and a gel above 10 degrees centigrade.

Figure 4:
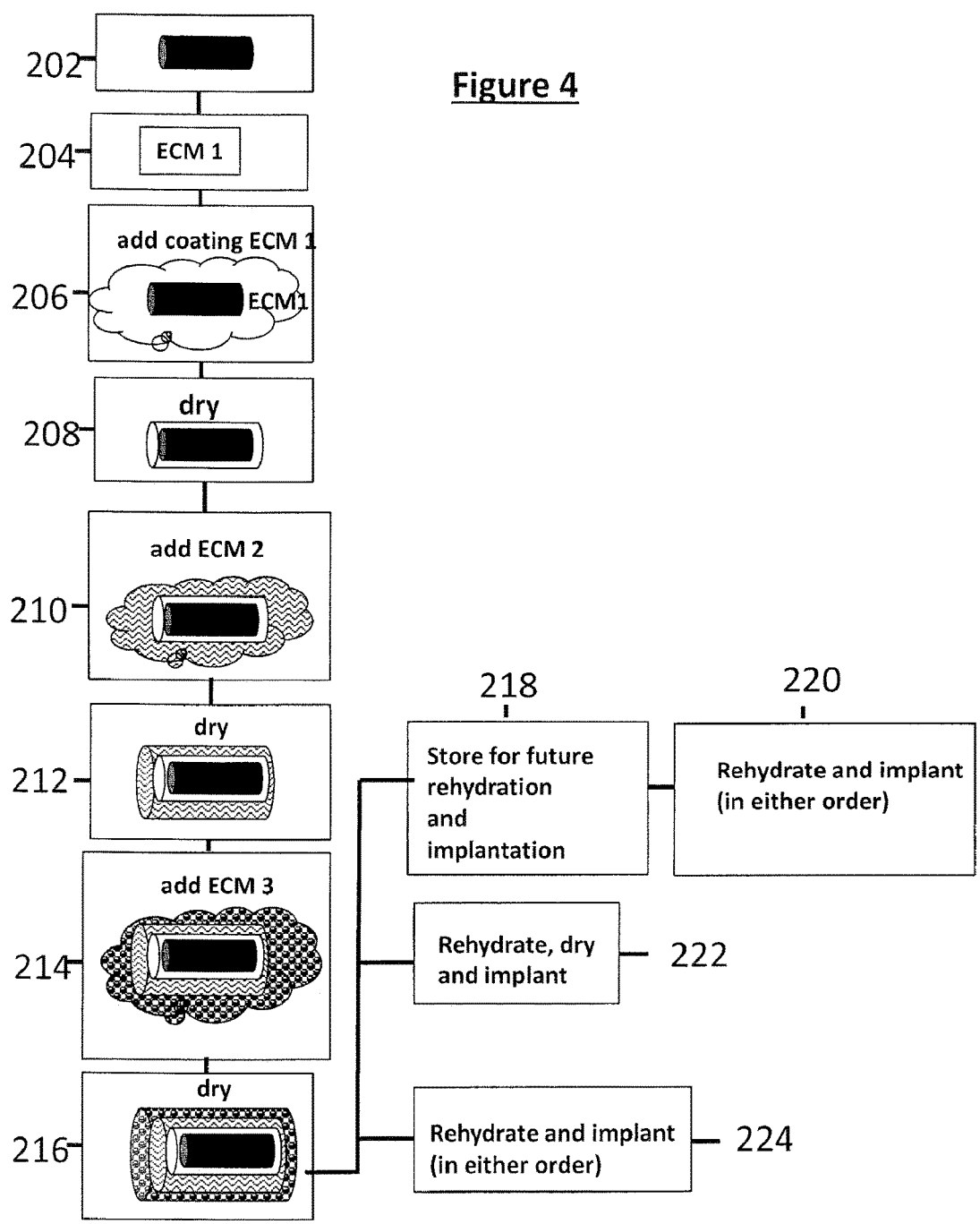
FIG. 4 is a flow chart showing a method according to another embodiment described herein.

Optionally, additional coatings can be added before the sensor is used or packaged. As shown in FIG. 3, after drying at 108, a second coating of the same material is applied at 110 and the coating is dried at 112. Optionally, a third layer of the extracellular matrix material is applied at 114 and then dried at 116. Additional coating and drying stages optionally can take place at 118. In some cases, the device is packaged at 120 for later use. When the packaged device is to be used, it is rehydrated before or after implantation, or both, at 122. In other cases, the device is used without being stored or packaged. When used, the device can be rehydrated before or after implantation, or both, at 124. This is done in order to eliminate salts, which have accumulated in the dry coating (toxic to tissue) and also since a sensor with a dry membrane is easier to implant. The wet Matrigel is easily sheared off the sensor surface during implantation. Having it dry is good for storage and shipping since refrigeration is not necessarily needed. Hydrating solution can be aqueous or non-aqueous solutions and can contain additives, such as proteins, drugs, antibodies. In embodiments, the device is rehydrated, dried and implanted at 126. In the embodiment shown in FIG. 4, multiple layers of various coatings are applied. The overall method of coating is designated as 200. Referring to FIG. 4, a device is obtained at 202 and a material (which may or may not be an extracellular matrix) to be used as a coating material is obtained at 204. The coating is configured in liquid or gel form. The device is partially or fully coated with the coating material at 206 by dipping, spraying, or another suitable technique. The coating is dried at 208. Drying can take place at room temperature, at elevated temperature, or at a temperature below room temperature. For a coating material such as solubilized basement membrane, it is generally known that the Matrigel is a liquid at 2-10 Deg. C. and a gel at 15-30 Deg. C. Optionally, additional coatings can be added before the sensor is used or packaged. As shown in FIG. 4, after drying at 208, a second coating of a different material is applied at 210 and the coating is dried at 212. Optionally, a third layer of extracellular matrix material is applied at 214 and then dried at 216. Additional coating and drying stages optionally can take place at 218. Optionally, the device is packaged at 218 for later use at 220. When the device is to be used, it is rehydrated before or after implantation, or both, at 222 or 224. At least two of the coatings are made of extracellular matrix. In embodiments, all of the layers are made of extracellular matrix.

Figure 5:
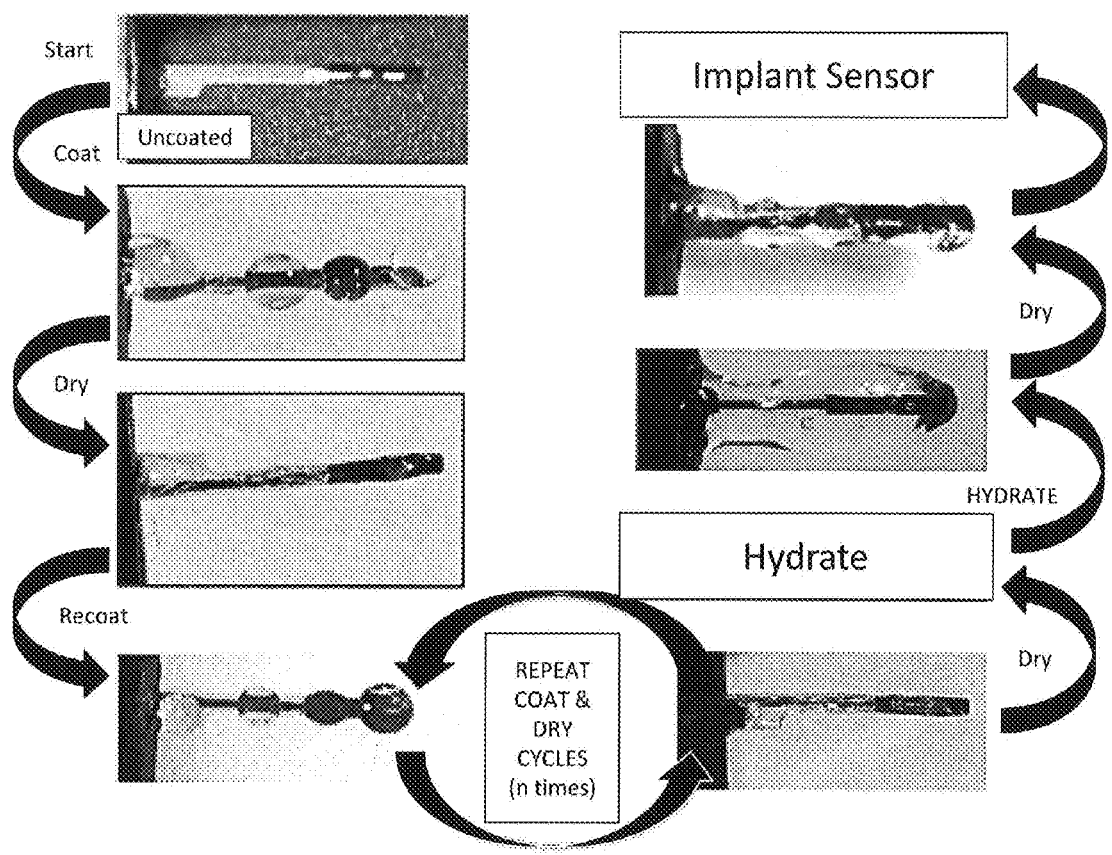
FIG. 5 shows photographs of a sensor at various stages of the coating process including coating, drying, re-hydrating and final drying.

FIG. 5 shows photographs of the coating process. A sensor is dipped in basement membrane, such as Matrigel, that is in the form of a liquid. The basement membrane is then dried. A second coat of the same or a different extracellular matrix is then applied and dried. Multiple coatings can be applied and dried. When the sensor is ready for use, the multilayer coating is hydrated to rinse away salts, retried, and implanted in biological tissue.

In embodiments, various VEGFs (VEGF-A, VEGF-B, VEGF-C, and/or VEGF-D) individually or in combination are bound to fibronectin (FN). The VEGF-fibronectin combination in turn can be added to ECM preparations such as basement membranes to make a complex that is coated on an implantable device and implanted in a dry or wet form in biological tissue. The ECM-fibronectin-VEGF combination will induce formation of addition vascular networks, thereby extending the useful lifespan of the device.

Methods Employed for Gene Transfer

In embodiments, there are a wide variety of methods employed for gene transfer in cells and tissue. Three of the major approaches used include: 1) plasmid based gene transfer, 2) retrovector based gene transfer and 3) adenovector based gene transfer. Plasmid based gene transfer utilizes "naked" DNA to directly transfer genetic information into cells in vitro and or in vivo. Plasmid based gene transfer has the advantage that it is simple, but it is extremely inefficient, particularly in vivo. Retrovector based gene transfer utilizes retroviral vectors to "carry" the selected genetic information into the cells via specific virus receptors on the surface of target cells. Retrovectors have the advantage in that they are extremely stable, but they require a selection procedure, which identifies cells in which the genes have successfully been transferred. Adenovectors, like retrovectors utilizes adenoviral vectors to "carry" the selected genetic information into the cells via specific virus receptors on the surface of target cells. Adenovectors have the advantage of being very efficient in gene transfer also the gene expression may be transient. Generally for gene therapy, adenovectors have been the system of choice. Adenovirus binds to a surface receptor known as CAR, and CARs have been identified on human (hCAR) and murine cells. Unfortunately not all cells have high enough levels of CAR to allow infection with adenovectors, thus limiting the spectrum of target cells in which gene transfer can be achieved. For example, generally fibroblasts have limited levels of CAR and thus are not used as target cells for adenovector based gene transfer. For the ATS, a protocol for genes transferred into target cells that are CAR deficient, thus allowing the use of adenovector in these cells.

Many of the materials listed above are described in U.S. patent application Ser. No. 10/578,171, Klueh et al., filed May 4, 2006 (published as US Patent Publication Number 2007/0077265 on Apr. 5, 2007), the contents of which are incorporated by reference herein in their entirety.

Neovascularization

CGM technology allows the patient to monitor their glucose level in real-time and as such, alerts the user when glucose levels are falling too low or rising too high. This knowledge can help the user to prevent potential harmful hyperglycemic or hypoglycemic events. Both of these events are damaging to the body's vasculature system and ultimately responsible for diabetes complications including death. Crucial to good CGM performance is an accurate glucose sensor.

Gene therapy studies described herein demonstrate that 1) VEGF-A based local gene therapy increases vascular networks (blood vessels and lymphatic vessels) at sites of glucose sensor implantation; and 2) this local increase of vascular networks enhances and extends glucose sensor function in vivo. This data shows that increasing vascular networks at sites of glucose sensor implantation enhances and extends continuous glucose monitoring (CGM) in vivo.

The formation of new BV is essential to embryonic development, wound healing and tumor growth in vivo. Central to all these various forms of new vessel formation is the local expression of angiogenic factors (AFs) such as VEGF, HGF, PDGF, IL-8, etc. (also see FIG. 24). These AFs play a key role in initiating new vessel formation in vivo, i.e. angiogenesis. During neovascularization, new BVs emerge and develop from preexisting vessels through various processes, which include vascular endothelial cell (VEC) proliferation and migration. This initial sequence of events results in tissue invasion by developing capillary sprouts. Upon formation of capillary sprouts, endothelial cells migrate toward the angiogenic stimulus into regeneration or developing tissue. Ultimately, tube to-tube connections are made by the capillary sprouts in order to obtain continuous blood flow.

Generally, BVs play a vital role in the delivery of nutrition (glucose) and oxygen to tissues, as well as the removal of $CO_2$ from the tissues. Additionally, these same networks of BVs are also critical to the delivery of inflammatory and immune cells to sites of injury, infection and wound healing. However, the various roles of LVs, as well as their structure and development, L-Angio, are generally not appreciated in the glucose sensor community. LVs are blind vessels, which arise within virtually all tissues. Outflow of the LVs as toward the lymph nodes is maintained by a series of leaflet valves, which allow uni-direction flow within the LVs. In normal tissues the lymphatics represent the major outflow of fluids and cells within the interstitial compartment, and as such have significant impact on interstitial flow and glucose levels. The fluids and cells that flow thru the LVs accumulate within the lymph node, and eventually drainage of the lymph node occurs back into the blood stream for eventual recirculation (e.g. lymphocytes and macrophages) or removal thru the kidneys and bowel. During tissue trauma, inflammation and wound healing, lymphatics play a critical role in draining excessive fluids (edema), tissue debris and inflammatory cells from the site of injury and thereby decreasing inflammation. This drainage is critical to minimizing additional tissue damage by removing all factors and cells from the trauma site and thereby promoting tissue repair and regeneration. In fact, a growing body of literature has demonstrated that 1) blocking lymphangiogensis enhances inflammation and tissue destruction and 2) enhancing LV number and function diminishes inflammation in a number of disease states.

The VEGF-A induced lymphatic vessels can be important in tissue drainage to reduce inflammation and tissue injury, including fluids (edema) and inflammatory cells associated with angiogenesis. The major control of both hemangiogenesis (H-Angio) and L-Angio appears to be through a related group of agonists and receptors known as the Vascular Endothelial Growth Factor (VEGF) family. The VEGF family is primarily composed of 4 agonists (VEGF-A, VEGF-B, VEGF-C, VEGF-D) with overlapping functions via their receptors. The agonists exert their angiogenic action on blood vessels (VEGF-A) and lymphatic endothelial cells (ECs) (VEGF-C and VEGF-D) thru 3 receptors present on the surfaces of these cells. Because of the central role of the VEGF family in human diseases such as cancer and inflammation, a number of antagonists of the various members of the VEGF family have been developed.

The VEGF family also plays a critical role in controlling wound healing, i.e. repair and regeneration. This central role of the VEGF family in wound healing is the result of the VEGF family's ability to control the formation of vascular networks at sites of tissue injury and inflammation. The ability of the VEGF family to control the formation of blood vessels and lymphatic vessels controls not only the influx of fluids, nutrients (glucose), oxygen and cells into the injured site to promote healing, but it also allows the removal of fluids (edema/swelling), tissue debris, and toxic factors as well as the removal of inflammatory cells all of which reduce inflammation and tissue injury and enhance and extend glucose sensor function and continuous glucose monitoring (CGM).

Frequently, unreliable glucose sensor function in vivo is the result of acute and chronic tissue reactions at the sensor implantation site (i.e. inflammation, fibrosis and vessel regression). These tissue reactions limit sensor function by 1) damaging (inflammation) and regressing (fibrosis) vascular networks (blood and lymphatic) that control real-time movement of fluids (Glucose) and cells (leukocytes) within tissue and 2) by inducing sensor "biofouling", including creation of leukocyte based "metabolic barriers" surrounding the sensors. Specifically, the loss of blood vessels results in loss of real-time blood glucose levels in the interstitial spaces. The loss of lymphatic networks at implantation sites prevents efficient drainage of tissue debris and inflammatory cells from the implantation site. The failure to properly drain inflammatory cells from implantation sites increases the "inflammatory load" at the implantation sites, thus increasing biofouling and loss of sensor accuracy. The data provided below shows that enhancing both blood vessel (BVs) and lymphatic vessel (LVs) networks at sensor implantation improves the accuracy and extends the functional lifespan of a sensor in continuous glucose monitoring.

In addition to the VEGF families of agonists and receptors, additional lymphangiogenic agonists/receptors have also been identified (FIG. 24). As is the case with the VEGF family the agonists can be expressed by a variety of cells if the corresponding receptor is present on lymphatic endothelial cells. The major LymphAngiogenic factors/receptors include Insulin-like Growth Factor (IGF)/IGF-1R; Platelet Derived Growth Factor-BB (PDGF-BB)/PDGFa/B; Angiopoietin-1 (Ang-1)/Tie-2 and HGF/HG-R 4 (FIG. 24).

System Comprising Kit

In embodiments, a system is provided comprising a kit that includes at least one extracellular matrix, a device to apply the ECM to an implantable device such as a cannula, or catheter, a protocol for using the kit to coat the implant with at least one layer of ECM as well as a specific drying and hydrating method described.

In another embodiment, a system is provided comprising a kit that includes at least one extracellular matrix, a device to apply the ECM to an implantable medical device, with the ECM being applied as a collar or sleeve, and a protocol for using the kit to coat the implant with at least one layer of ECM as well as a specific drying and hydrating method described.

Embodiments Using Crosslinked Basement Membrane

Figure 42:
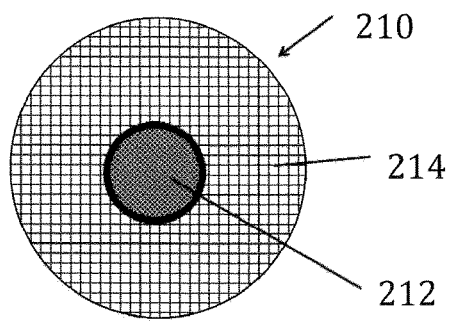
FIG. 42 schematically shows an implant with a coating formed from crosslinked basement membrane.
Figure 43:
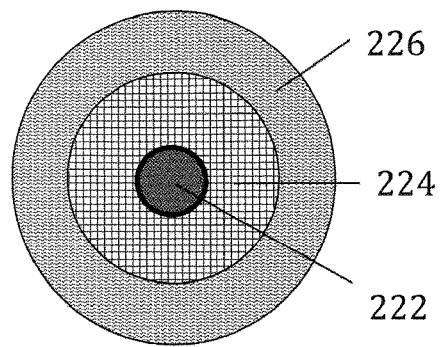
FIG. 43 schematically shows an implant with a multi-layer coating in which the inner layer is formed from crosslinked basement membrane and the outer layer is formed from basement membrane that is not crosslinked.

FIG. 42 shows a coated implant 210, which includes an implantable device 212 which is surrounded by a coating layer 214 of crosslinked basement membrane. FIG. 43 shows a coated implant 220, which includes an implantable device 222, which is surrounded by an inner coating layer 224 of crosslinked basement membrane and an outer coating 226 of basement membrane that is not crosslinked. Alternatively, both the inner and outer coating layers may be crosslinked, either in a single crosslinking step or in separate crosslinking steps. In another embodiment, the inner layer is not crosslinked and the outer layer is crosslinked. Furthermore, additional crosslinked or non-crosslinked layers can be added over layer 226. In embodiments, the basement membrane layers can be added in liquid or gel form. In embodiments, pre-dried, crosslinked or non-crosslinked basement membrane layers can be applied on or beneath liquid and/or gel layers, or directly on the implantable device as the inner layer. In embodiments, the pre-dried layers are in the form of sheets.

Figure 44:
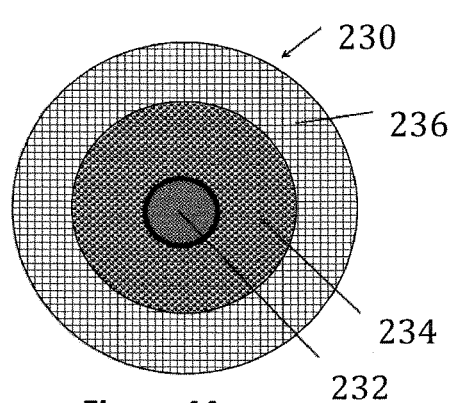
FIG. 44 schematically shows an implant with a multi-layer coating in which the inner layer is formed from a drug release system and the outer layer is formed from crosslinked basement membrane.
Figure 45:
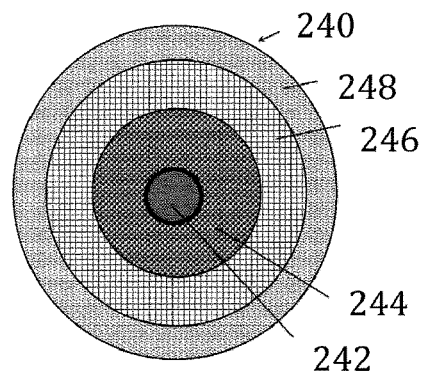
FIG. 45 schematically shows an implant with a multi-layer coating in which the inner layer is formed form a drug release system, the intermediate layer is formed from crosslinked basement membrane, and the outer layer is formed from basement membrane that is not crosslinked.
Figure 46:
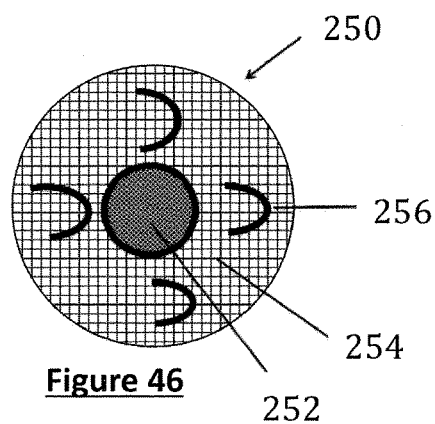
FIG. 46 schematically shows an implant with a coating formed from crosslinked basement membrane, in which the crosslinked basement membrane supports one or more factors, natural fibers, and/or synthetic fibers.

FIG. 44 shows a coated implant 230, which include an implantable device 232, which is surrounded by an inner coating layer 234 of a drug release system, and an outer coating layer 236 of crosslinked basement membrane. In alternative embodiments, the intermediate layer is crosslinked and the outer layer with their crosslinked or not crosslinked. FIG. 45 shows a coated implant 240 which includes an implantable device, 242, an inner coating layer 244 of a drug release system, an intermediate coating layer 246 of cross-linked basement membrane, and an outer coating layer 238 of basement membrane that is not crosslinked. The order of the layers can be varied. FIG. 46 shows a coated implant 250 with an implantable device 252 having a coating comprising a crosslinked basement membrane that contains natural or synthetic fiber and or matrices. Such materials can be added, for example, to impart additional strength to the layer. Non-limiting examples of natural fibrous additives include fibrin; collagens (Fibrillar (Type I, II, III, V, XI); Facit (Type IX, XII, XIV); Short chain (Type VIII, X); Basement membrane (Type IV); Other (Type VI, VII, XIII); fibronectins; laminins; elastins; and Proteoglycans: (Chondroitin sulfate, Heparan sulfate, Keratan sulfate, Hyaluronic acid). Non-limiting examples of synthetic fibrous include Polyurethane; Polysulfone; Calcium phosphate; Hyaluronic acid; Polypropylene; Bioactive glass; Extracellular matrix; Polyvinyl alcohol; Polyglycolide; Polylactide; Poly(propylene fumarate); Polycyanoacrylate; Poly($\varepsilon$-caprolactone); Polydioxanone; Polyhydroxyalkanoates; Poly(ortho ester); Poly(ether ester); Poly(ethylene oxide); Polybutylene terephthalate; Hydroxyapatite; Tricalcium phosphate; Poly(ethylene glycol); Poly(ester urethane); Poly(acrylic acid); Lysine diisocyanate; Biphasic calcium phosphate; Polyacrylamide; Polymethylmethacrylate; Poly(L-lactic acid); Poly(l-lactide-co-glycolide); Poly (trimethylene carbonate); Polydimethylsiloxane; Polytetrafluoroethylene; Poly(ethylene-co-vinylacetate); Poly (glycolide-co-ε-caprolactone); Poly(l-lactide-co-caprolactone); Poly(DL-lactide); Poly-L/D-lactide; Poly (lactic acid-glycolic acid); Poly(3-hydroxybutyrate) 3-hydroxyvalerate; Poly(caprolactone-co-trimethylene carbonate); Poly(N-isopropylacrylamide); Poly(dimethylaminoethylmethacrylate) hydrochloride; Poly(D,L-lactide-co-caprolactone); Poly(l-lactide-co-ε-caprolactone); Tricalcium phosphate.

In further embodiments, one or more layers contain factors, drugs, agents, proteases and protease inhibitor, tissue and cell response modifiers virus, genetic material, and cells as described above.

In general, the material of the embodiments described herein may be alternately formulated to comprise, consist of, or consist essentially of, any appropriate components herein disclosed. The material of the disclosed embodiments may additionally, or alternatively, be formulated so as to be devoid, or substantially free, of any components, materials, ingredients, factors, cellular constituents, cytokines, growth factors, tissue types, genetic elements, adjuvants or species used in the prior art compositions or that are otherwise not necessary to the achievement of the function and/or objectives of the described embodiments.

EXAMPLES

Gene therapy studies described below demonstrate that 1) VEGF-A based local gene therapy increases vascular networks (blood vessels and lymphatic vessels) at sites of glucose sensor implantation; and 2) this local increase of vascular networks enhances and extends glucose sensor function in vivo (FIG. 7, 8, 9, 10, 11, 12). This data shows that increasing vascular networks at sites of glucose sensor implantation enhances continuous glucose monitoring (CGM) performance in vivo.

Example 1A—Impact of Local Vascular Endothelial Cell Growth Factor Gene Therapy on Continuous Glucose Monitoring To induce sustained vascular networks at sites of sensor implantation, the potential of local VEGF gene therapy to extend sensor function and CGM in a murine model was investigated. Specifically, the impact was determined of direct injection of adenovirus vectors containing mouse VEGF gene (AdvVEGF) or AdvLacZ (control virus) at the sites of glucose sensor implantation in vivo (FIG. 6). Injections of viruses or solutions were done at the sensor tip post sensor implantation (see FIG. 6B, arrow). The injection procedure was as follows:

Detailed Description of Mouse Surgery:

The mice were anesthetized while being monitored for withdrawal reflex, heart rate, respiratory rate, color, and vital signs to ensure appropriate anesthesia before surgical procedures were performed. Prior to the sensor implantation, the back of the mouse was clipped, shaved, and prepared with Betadine solutions. Prior to sensor implantation, 100 to 200 ml of injectable sterile, pyrogen free, 0.9% NaCl was injected subcutaneously (s. c.) in the back area of the anesthetized mouse to provide an "implantation pocket". The implantation pocket is used to minimize tissue and sensor damage during sensor implantation. A small opening was made in the "implantation pocket" using a 23 to 25-gauge needle and the sensor was then implanted in the subcutaneous pocket with the sensor leads exposed. The size of the sensor implanted was about 0.5 mm in diameter×1 cm long. A small polyester mesh was placed on top of the exposed sensor leads. Sensor leads and nylon mesh were secured to the shaved mouse skin by applying a coating of NewSkin (Liquid Bandage). Mice were kept under anesthesia until New Skin Liquid Bandage was dried. Once sensors are implanted, mice were housed individually as a precaution to prevent dislodging of the sensor. Periodic blood glucose levels were obtained in the sensor implanted mice. The adenovirus vectors containing VEGF gene (or a control) were injected (30 ul of saline containing virus or saline alone) at site of sensor implantation at various times post sensor implantation (FIG. 6). 1 dosage of virus is injected for up to 3 different time intervals (e.g. days 5, 6 and 7 post sensor placement).

Additional controls of 1) saline injections and 2) no injections were also done. For each treatment (injection) sensors were implanted in the mice, and on 3 consecutive days (days 6, 7 & 8) 30 uls of saline, AdvLacZ or AdvVEGF were injected at the implanted sensor tip, i.e. the sensing element of the sensor (see FIG. 6B). After the initial 3 injections were completed there were no further treatments. Both pre and post injection, the mice were allowed to roam freely. It should be noted that CGM was done for 28 days with 21 days post-adenovirus treatment/injection i.e. (days 7-28) to minimize any impact of acquired immunity against adenovirus infected tissue cells 33, 34. CGM output in nAs (FIG. 7A-P) was recorded and actual blood glucose levels were determined using the Abbott Freestyle external monitor (diamonds in FIG. 7A-P). As can be seen in FIG. 7A-D sensors implanted in mice with treatments of no-injection, saline injection (FIG. 7E-H), and Adv-LacZ (viral vector control) (FIG. 7I-L) injection showed periods where the mouse blood glucose (diamonds) did not correspond to sensor output (continuous line). On the other hand, sensors implanted in mice with Adv-VEGF treatment did not experience these sensor functionality losses (Figure M-P).

Impact of VEGF Gene Therapy on Sensor Function

Figures 7A, 7B, 7C, 7D:
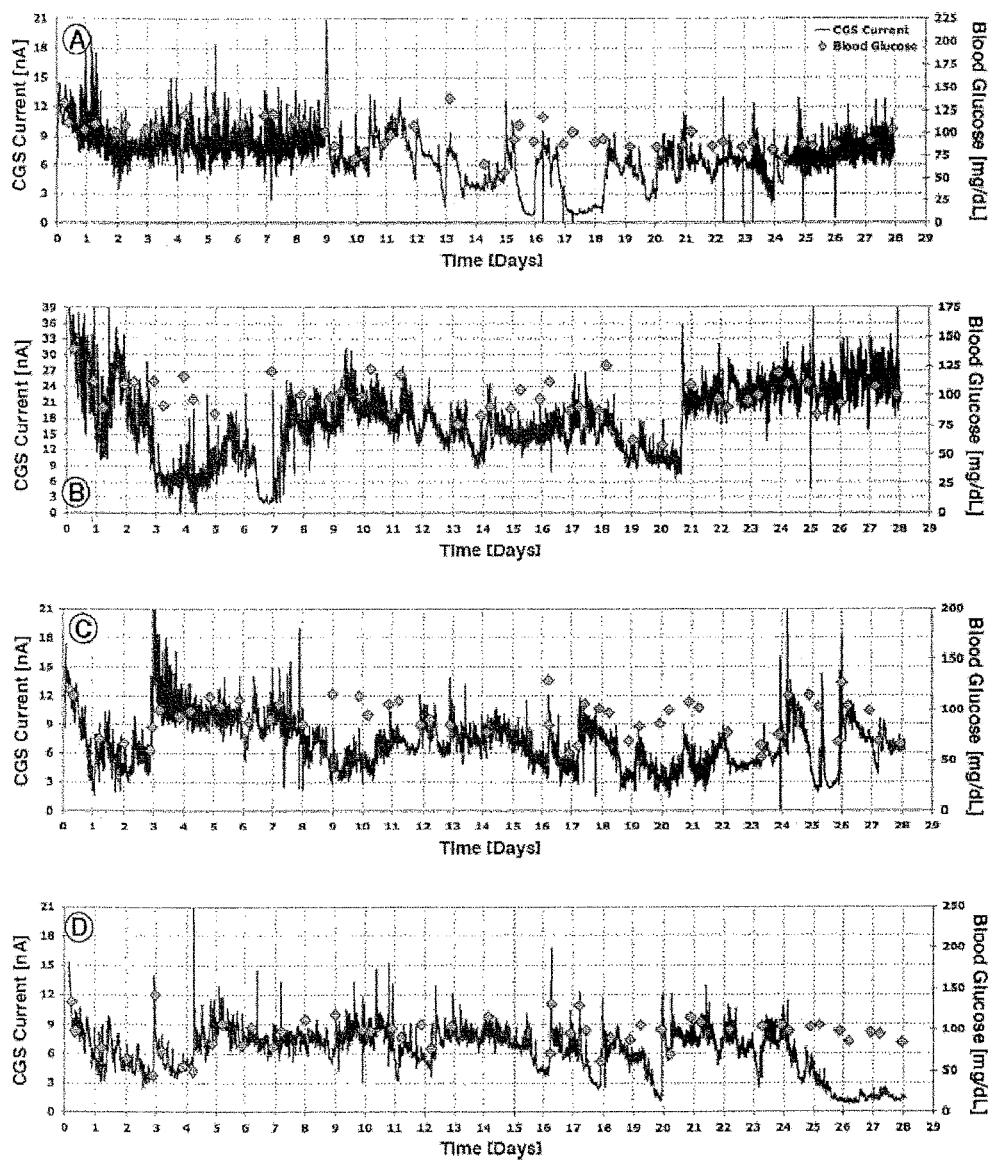

FIG. 7 shows the results of continuous glucose monitoring (CGM) in saline, Adv-LacZ, and Adv-VEGFa injected C57BL/6 mice for up to 28 days post sensor implantation (DPI). FIG. 7A-7D shows a control with no injection. FIG. 7E-7H are representative of CGM in saline (control), FIGS. 7I-7L are representative of Adv-LacZ, and FIGS. 7M-7P are representative of Adv-VEGFa injected C57BL/6 mice for up to 28 days post sensor implantation. Sensor output is expressed as CGS output (nA) and is represented by the lines. Diamonds represent blood glucose levels, and triangles represent injections. For this study a total of 80 mice were evaluated.

Example 1B—Mean Absolute Relative Difference (MARD) Analysis

Figure 8:
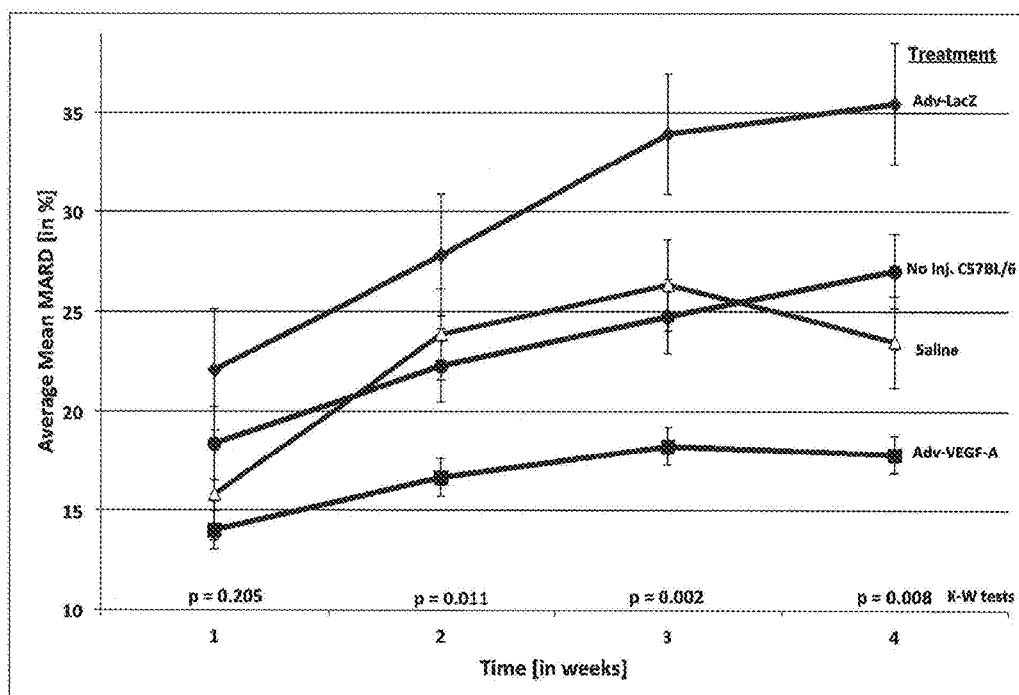
FIG. 8 is a line graph showing Mean Absolute Relative Difference calculations for the data shown in FIG. 7.

To assess the impact of local VEGF gene therapy, the resulting CGM data were analyzed using standard Mean MARD analysis. A difference was observed between the four treatment groups, which was statistically significant, as per the Kruskal-Wallis test (p=0.003). The data is shown in FIG. 8. Cumulative average mean MARD from weeks 1 to 4 by treatment group: p-values represent the significance of the difference among the four treatment groups in average mean MARD value for each of individual weeks, by the non-parametric Kruskal-Wallis test.

FIG. 8 demonstrates the difference and trends in the MARD values between the treatment groups over the course of the 28-day experiment. Adv-VEGF-A treated mice had lower MARD values than all the other control groups, demonstrating its effectiveness in improving glucose sensor function. In addition, the difference between the Adv-VEGF-A MARD values and the other treatment groups grew over the four weeks. In concert with the timing of the injections around the end of the first week, it was observed that the statistical difference between the groups, as evaluated by Kruskal-Wallis tests, was not significant during the first week (p=0.205), but becomes statistically significant in weeks 2, 3, and 4 (p=0.011, 0.002, and 0.008, respectively).

FIG. 10 shows Average Mean Absolute Relative Difference (MARD) values for all four weeks of mice treated with adenoviral vectors bearing VEGF-A or LacZ (Adv-VEGF-A or Adv-LacZ), and their saline or no injection controls. FIG. 10 demonstrates the statistical comparisons between the total mean MARDs for mice within each treatment group. As shown in FIG. 10, it was observed that the Adv-VEGF-A treated mice had a total (for the entire 4 week testing period) mean MARD of 17.44+/−5.72%, whereas the Saline and No Injection C57BL/6 control mice had intermediate MARDs of 24.91+/−15.74% and 23.50+/−9.83% respectively, and Adv-LacZ had the worst mean MARD of 31.49+/−14.50%. The Adv-VEGF-A treated mice had significantly (p<0.05) lower total mean MARD than every other treatment group, as measured by student t-tests. In addition, the Adv-VEGF-A mean MARD data was normally distributed, and had a smaller standard deviation than every other group. The sample sizes are relatively large for such investigations with approximately 15 or more mice in each group.

Example 1C—Blood Vessel Density and Regression Analysis

Figure 9:
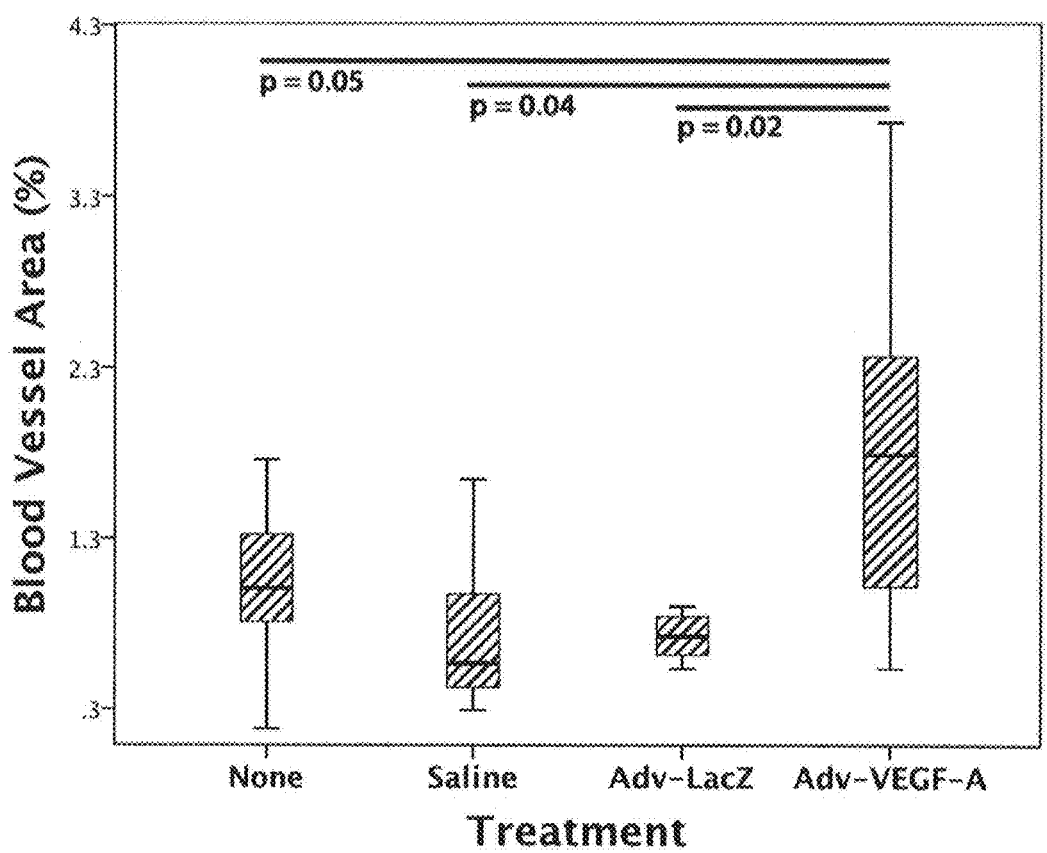
FIG. 9 is a boxplot of blood vessel density as measured by percent area and treatment group for no injection, saline injection, Adv-LacZ and Adv-VEGFa injection.

The measured and calculated density of blood vessels among four treatment groups showed a statistically significant increase in the percent area of tissue surrounding the implanted sensor which were identifiable blood vessels, as per immunohistology. The mean percent area, which was blood vessel, for the Adv-VEGFa treated group of mice was 2.15+/−1.55%, whereas the Adv-LacZ, saline, and no treatment groups had mean percent blood vessel areas of 0.77+/−0.23%, 0.76+/−0.48%, and 1.03+/−0.41%, respectively. The statistical significance of the difference among the four treatment groups, measured by the ANOVA statistical test, was a p-value of 0.003. In two tailed student t-tests directly comparing the Adv-VEGFa group to the other three treatment groups specifically, also showed that the Adv-VEGFa mean percent area was statistically greater than the Adv-LacZ, saline, and no treatment groups, with p-values of 0.02, 0.02, and 0.05 respectively. FIG. 9 demonstrates the relative distributions of blood vessel density, through a boxplot of the percent blood vessel area of the respective treatment groups. To determine if there was a significant statistical relationship between the observed increase in blood vessel density and improved sensor function, we conducted a linear regression analysis between blood vessel density and MARD values. As seen in FIGS. 9, 10, 11 and 12, for those mice among all treatment groups that survived the entire four week time course of the experiment and whose blood vessel density around the sensor was measured, a functional improvement of 9.12+/−2.77% decrease in MARD for every 1% increase in blood vessel area was observed. This ratio was statistically significant with a p-value of 0.005 and had a correlation $R^2$ value of 0.40. In addition, a trend in the significance of the positive relationship between increased percent area as blood vessel and improved sensor function can be seen in FIG. 12.

Figure 12:
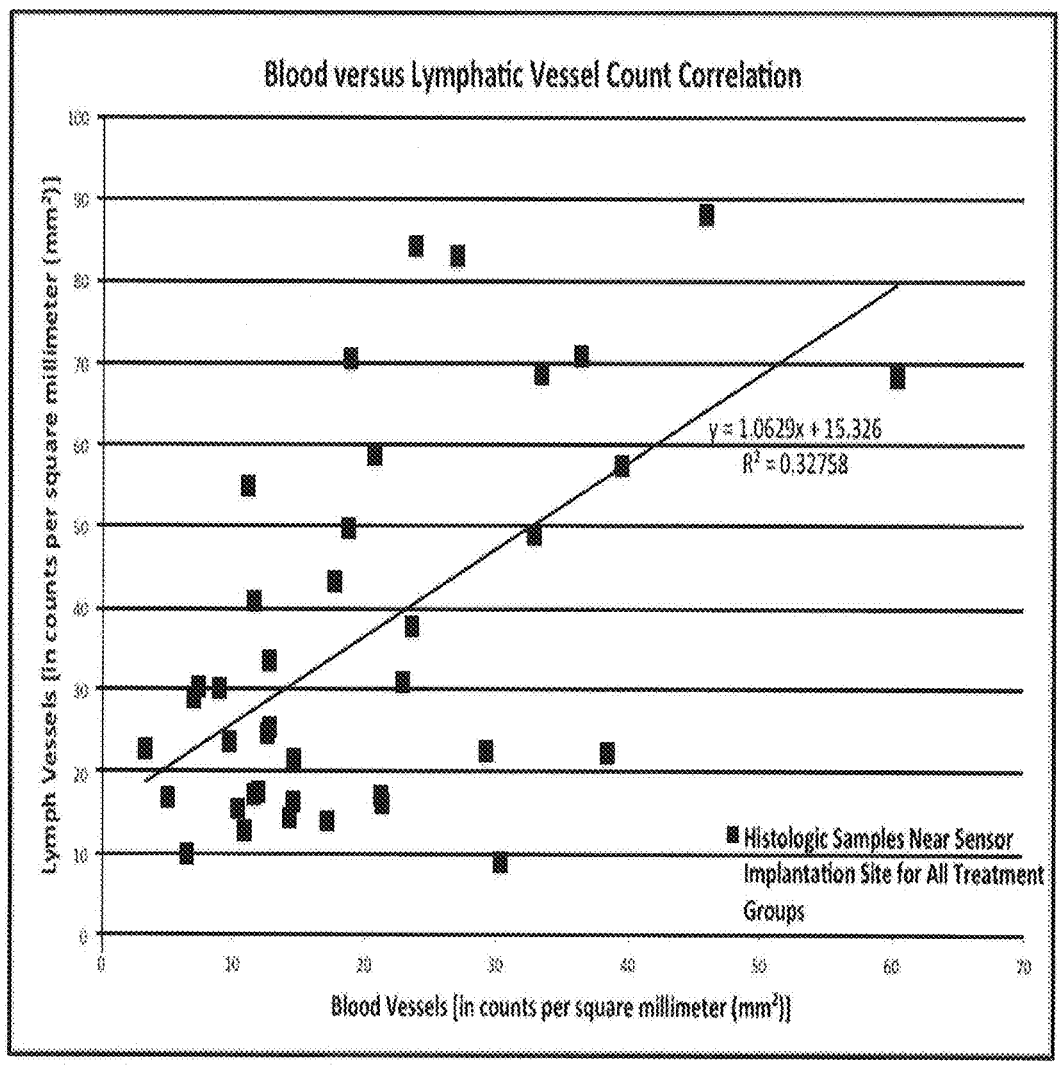
FIG. 12 is a graph correlating blood vessel density and lymph vessel density for all treatment groups.

FIG. 12 provides a simple linear regression analysis that was conducted on matching histological samples from all treatment groups, whose lymphatic and blood vessels were quantified in counts per square millimeter of mouse back tissue, proximal to the glucose sensor implantation site. The ratio of lymphatic to blood vessels suggests that lymphatic and blood vessels growth, formation, and maintenance track in a 1 to 1 ratio. The significance is expressed as p-values with statistical significance achieved at p<0.05. $R^2$ represents the correlation between the blood and lymphatic vessel variables, as counts per square millimeter.

The significance of the linear regression models and their coefficients grows over the four-week time course of the experiment, with those experiments in the fourth week having the greatest significance. This trend parallels the very similar increasing significance of the better and improving MARD values of the Adv-VEGFa injected mice as compared to the other treatment groups, over the same four week time course, as seen in FIG. 8. Assuming that Adv-VEGFa injections are efficacious, these two trends match the results one would expect from the timing of the injections, which occurred around the end of the first week, i.e. days 6, 7, and 8. As seen in FIG. 12, we observe that the statistical significance of the linear regression models and their coefficients, is not significant during the first and second weeks (p=0.442 and 0.111, respectively), but become statistically significant in weeks 3 and 4 (p=0.018 and 0.005, respectively), and consistently grows throughout the four-week experimental time course.

Example 1D—Analysis of the Impact of Adv-VEGF on Hemangiogenesis at Sensor Implantation Sites To evaluate the impact of Adv-VEGFa and control treatments at sensor implantation sites, tissue samples were obtained from the implantation sites of the various treatment/injection groups and fixed in Zn buffer. The resulting samples were processed for immunohistochemistry (IHC) for vessel detection and quantitation. Mouse blood vessels were detected using anti-mouse CD31[27]. Non-immune IgG was used as a specificity control for both antibodies. The resulting IHC slides were digitized using an Aperio Digital Microscope. The resulting digital images were analyzed for hemangiogenesis (H-Angio) using ImageJ (NIH). FIG. 9, Blood Vessel Analysis, is a boxplot of blood vessel density as measured by percent area and treatment group. P-values at the top represent student t-test p-values for the significance of the difference between the paired comparisons with Adv-VEGF blood vessel density indicated by the lines.

The resulting data was statistically evaluated using student t-test. Adv-VEGFa induced a 1.9, 2.5, and 2.4 fold increase in mean blood vessel percent area H-Angio at sensor implantation sites when compared to non-injected (p=0.025), saline injected (p=0.019) or Adv-LacZ (p=0.004), respectively. These studies clearly demonstrate that Adv-VEGFa increases H-Angio at sensor implantation sites when compared to non-injected and various control treated sensor implantation sites. Equally important is the fact that sensor performance was also enhanced by Adv-VEGFa when compared to all controls (see total mean MARD, FIG. 10). These studies establish "proof of principle" that increasing H-Angio with Adv-VEGFa significantly increases sensor function and CGM.

Figure 11:
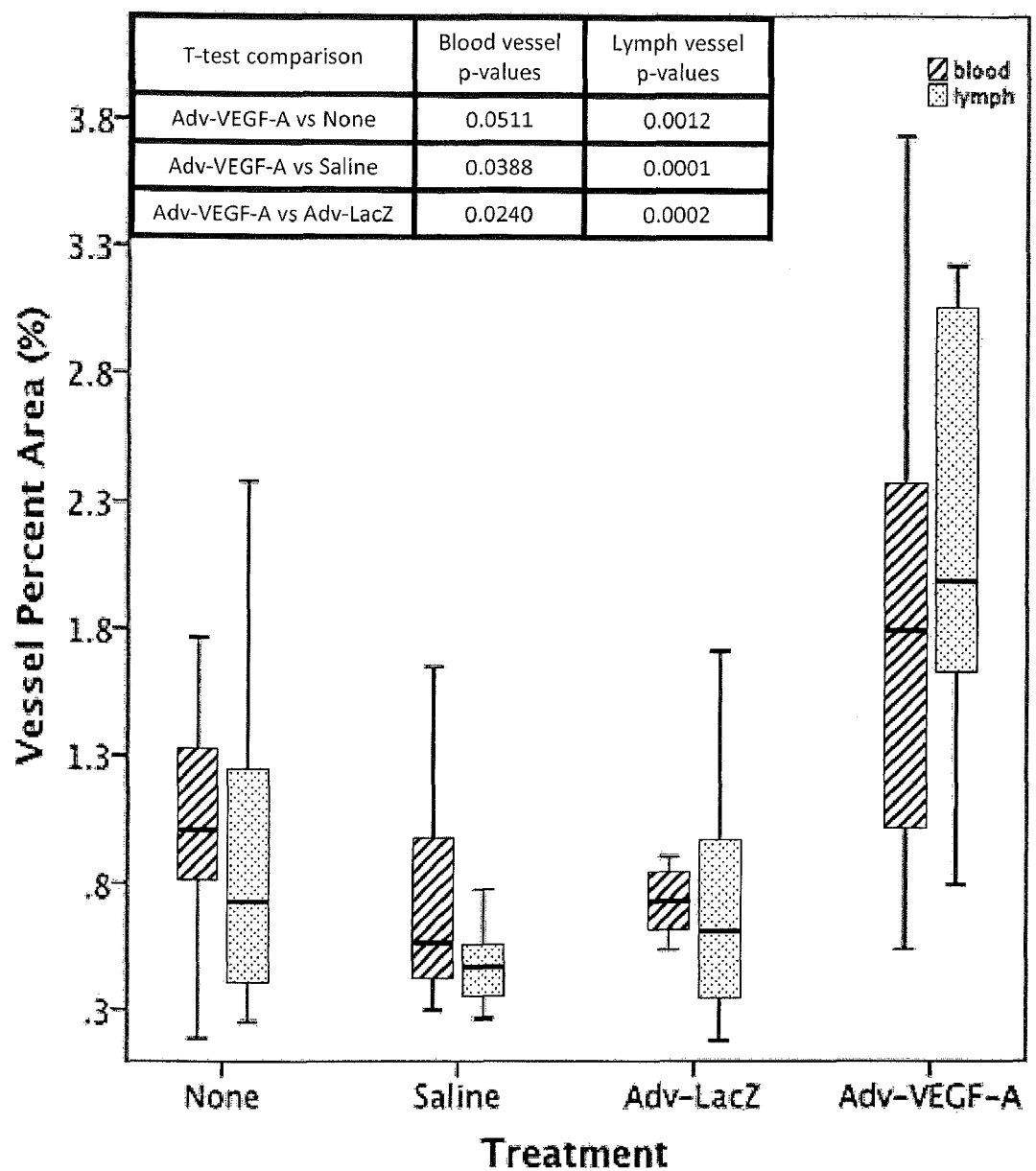
FIG. 11 is a boxplot of lymphatic vessel density and blood vessel density as measured by percent area and treatment groups for all the treatment groups.

Example 1E—Analysis of the Impact of Adv-VEGF-A on Lymphangiogenesis at Sensor Implantation Sites To evaluate the impact of Adv-VEGF-A and control treatments at sensor implantation sites, tissue samples were obtained from the implantation sites of the various treatment/injection groups and fixed in Zn buffer. The resulting samples were processed for immunohistochemistry (IHC) for vessel detection and quantitation. Mouse lymph vessels were detected using anti-mouse podoplanin(8), while mouse blood vessels were identified using anti-CD31 immunohistochemistry. Non-immune IgG was used as a specificity control for both antibodies. The resulting IHC slides were digitized using an Aperio Digital Microscope. The resulting digital images were analyzed for lymphangiogenesis (L-Angio) using ImageJ (NIH). The mean percent area as lymph vessel, for the Adv-VEGF-A treated group of mice was 2.12+/−0.81%, whereas the Adv-LacZ, saline, and no treatment groups had mean percent lymph vessel areas of 0.67+/−0.46%, 0.48+/−0.18%, and 0.91+/−0.66%, respectively. The statistical significance of the difference among the four treatment groups, measured by the ANOVA statistical test, was a p-value of $2.03 \times 10^{-6}$. FIG. 11 demonstrates the relative distributions of lymph vessel density, through a boxplot of the percent lymph vessel area of the respective treatment groups. The resulting data was statistically evaluated using student t-test. Adv-VEGF-A induced a 2.3, 4.5, and 3.2 fold increase in mean lymph vessel percent area L-Angio at sensor implantation sites when compared to non-injected ($p=0.001$), saline injected ($p=0.0001$) or Adv-LacZ ($p=0.0002$), respectively. These studies clearly demonstrate that Adv-VEGF-A increases L-Angio at sensor implantation sites when compared to non-injected and various control treated sensor implantation sites. Equally important is the fact that sensor performance was also enhanced by Adv-VEGF-A when compared to all controls (see total mean MARD, FIG. 10). These studies establish "proof of principle" that increasing L-Angio with Adv-VEGF-A significantly increases sensor function and CGM.

Example 1F—Blood Vs Lymph Graph

Lymphatic and blood vessels from histological samples of all treatment groups were quantified in counts per square millimeter of mouse back tissue, proximal to the glucose sensor implantation site, as per immunohistology following staining of selected samples against CD31 and podoplanin antigens, to identify blood and lymph vessels respectively. In FIG. 12, a graph of the relationship between blood and lymphatic vessel counts for each individual sample is illustrated, with a linear trend line. In addition, simple linear regression analysis was conducted on these counts per square millimeter of blood and lymphatic vessels in mouse back tissue. The ratio of lymphatic to blood vessels (1.06+/−0.25) suggests that lymphatic and blood vessel growth, formation, and maintenance track in a 1 to 1 correspondence, which is consistent with other observations, particular in cornea experimental models (ref). Particularly in response to VEGF-A, the vessel growth of both blood and lymph vessels are biologically coordinated. As shown in FIG. 13B, the linear regression model of this blood and lymph coordination from our histological observations was very significant ($p=0.0001$), particularly since the sample size for this model was relatively large ($n=39$). $R^2$ represents the statistical correlation between the blood and lymphatic vessel variables, as counts per square millimeter, and was 0.33.

Example 1G—Lymph Vessel Density and Regression Analysis

To determine if there was a significant statistical relationship between the observed increase in lymph vessel density and improved sensor function, we conducted a linear regression analysis between lymph vessel density and MARD values.

FIG. 13C provides a simple linear regression analysis to determine the contribution of lymph vessel density to glucose sensor function. Reduction in average Mean Absolute Relative Difference (MARD) values represents an improvement in glucose sensor function. Quantified increases in lymphatic vessels, as measured in percent area as lymphatic vessel, are determined to decrease MARD values by the ratios in the table above, and therefore improve glucose sensor function. The results are tabulated for all data combined (total) and cumulative one, two, three, and four weeks only, i.e. all those mice that survive into the first, second, third, and fourth weeks respectively. The significance is expressed as p-values with statistical significance achieved at $p<0.05$. $R^2$ represents the correlation between MARD and percent area as lymphatic vessel variables.

As seen in FIG. 13C, for those mice among all treatment groups that survived the entire four week time course of the experiment and whose lymph vessel density around the sensor was measured, a functional improvement of −4.29+/−1.70% decrease in MARD for every 1% increase in lymph vessel area was observed. This ratio was statistically significant with a p-value of 0.024 and had a correlation $R^2$ value of 0.30. In addition, a trend in the significance of the positive relationship between increased percent area as lymph vessel and improved sensor function can be seen in FIG. 13C. The significance of the linear regression models and their coefficients grows over the four-week time course of the experiment, with those experiments in the fourth week having the greatest significance. This trend parallels the very similar increasing significance of the better and improving MARD values of the Adv-VEGF-A injected mice as compared to the other treatment groups, over the same four week time course, as seen in FIG. 8. Assuming that Adv-VEGF-A injections are efficacious, these two trends match the results one would expect from the timing of the injections, which occurred around the end of the first week, i.e. days 6, 7, and 8. As seen in FIG. 13C, we observe that the statistical significance of the linear regression models and their coefficients, are not significant during the first, second, or third weeks ($p=0.69$, 0.226, and 0.080 respectively), but become statistically significant only in week 4 ($p=0.024$), but consistently grows throughout the four week experimental time course. The linear regression model was also statistically over the entire 4 week time course, ($p=0.046$).

By comparison, the mean percent area as blood vessel, for the Adv-VEGF treated group of mice was 2.15+/−1.55%, whereas the Adv-LacZ, saline, and no treatment groups had mean percent blood vessel areas of 0.77+/−0.23%, 0.76+/−0.48%, and 1.03+/−0.41%, respectively. The statistical significance of the difference among the four treatment groups, measured by the ANOVA statistical test, was a p-value of 0.003. In two tailed student t-tests directly comparing the Adv-VEGF group to the other three treatment groups specifically, also showed that the Adv-VEGF mean percent area was statistically greater than the Adv-LacZ, saline, and no treatment groups, with p-values of 0.02, 0.04, and 0.05 respectively (FIG. 9). FIG. 11 demonstrates the relative distributions of blood vessel density, through a boxplot of the percent blood vessel area of the respective treatment groups. To determine if there was a significant statistical relationship between the observed increase in blood vessel density and improved sensor function, we conducted a linear regression analysis between blood vessel density and MARD values.

FIG. 13A provides a simple linear regression analysis was conducted to determine the contribution of blood vessel density to glucose sensor function. Reduction in average Mean Absolute Relative Difference (MARD) values represents an improvement in glucose sensor function. Quantified increases in blood vessels, as measured in percent area as blood vessel, are determined to decrease MARD values by the ratios in the table above, and therefore improve glucose sensor function. The results are tabulated for all data combined (total) and cumulative one, two, three, and four weeks only, i.e. all those mice that survive into the first, second, third, and fourth weeks respectively. The significance is expressed as p-values with statistical significance achieved at $p<0.05$. $R^2$ represents the correlation between MARD and percent area as blood vessel variables.

As seen in FIG. 13A, for those mice among all treatment groups that survived the entire four week time course of the experiment and whose blood vessel density around the sensor was measured, a functional improvement of 9.12+/−2.77% decrease in MARD for every 1% increase in blood vessel area was observed. This ratio was statistically significant with a p-value of 0.005 and had a correlation $R^2$ value of 0.40. In addition, a trend in the significance of the positive relationship between increased percent area as blood vessel and improved sensor function can be seen in FIG. 13A. The significance of the linear regression models and their coefficients grows over the four-week time course of the experiment, with those experiments in the fourth week having the greatest significance. This trend parallels the very similar increasing significance of the better and improving MARD values of the Adv-VEGF-A injected mice as compared to the other treatment groups, over the same four week time course, as seen in FIG. 8. Assuming that Adv-VEGF injections are efficacious, these two trends match the results one would expect from the timing of the injections, which occurred around the end of the first week, i.e. days 6, 7, and 8. As seen in FIG. 13A, we observe that the statistical significance of the linear regression models and their coefficients, is not significant during the first and second weeks ($p=0.442$ and 0.111, respectively), but become statistically significant in weeks 3 and 4 ($p=0.018$ and 0.005, respectively), and consistently grows throughout the four-week experimental time course.

Example 1H—Combined Linear Regression Model with Both Blood and Lymph Variables

Simple linear regression analysis was then conducted to determine the contribution of both blood and lymph vessel density to glucose sensor function. Reduction in average Mean Absolute Relative Difference (MARD) values represents an improvement in glucose sensor function. Quantified increases in both blood and lymph vessels, as measured in percent area as blood or lymph vessel, were determined to decrease MARD values by the ratios described above, and therefore improve glucose sensor function. The results are tabulated for all data combined (total) and cumulative one, two, three, and four weeks only, i.e. all those mice that survive into the first, second, third, and fourth weeks respectively.

FIG. 13D provides a simple linear regression analysis to determine the contribution of both blood and lymph vessel density to glucose sensor function. Reduction in average Mean Absolute Relative Difference (MARD) values represents an improvement in glucose sensor function. Quantified increases in blood vessels, as measured in percent area as blood vessel, are determined to decrease MARD values by the ratios in the table above, and therefore improve glucose sensor function. The results are tabulated for all data combined (total) and cumulative one, two, three, and four weeks only, i.e. all those mice that survive into the first, second, third, and fourth weeks respectively. The significance is expressed as p-values with statistical significance achieved at $p<0.05$. $R^2$ represents the correlation between MARD and both the percent area as blood vessel and percent area as lymphatic vessel variables, as per this linear regression model.

As seen in FIG. 13D, for those mice among all treatment groups that survived the entire four week time course of the experiment and whose blood and lymph vessel density around the sensor was measured, a functional improvement of 7.13+/−4.74% decrease in MARD for every 1% increase in blood vessel area, and a 1.28+/−2.59% decrease in MARD for every 1% increase in lymph vessel area was observed. This ratio was statistically significant with a p-value of 0.03 and had a correlation $R^2$ value of 0.40. In addition, a trend in the significance of the positive relationship between increased percent area as blood and lymph vessel and improved sensor function can be seen in FIG. 13A. As seen in FIG. 13D, it was observed that the statistical significance of the linear regression models and their coefficients, is not significant during the first, second, and third weeks ($p=0.321$, 0.293, and 0.068 respectively), but becomes statistically significant in week 4 ($p=0.030$), and consistently grows throughout the four-week experimental time course. $R^2$ represents the correlation between MARD and both the percent area as blood vessel and percent area as lymphatic vessel variables, as per this linear regression model was 0.40, approximately the same as for the linear regression model for MARDs with the blood vessel variable alone.

Example 2—Basement Membrane Coating for Glucose Sensors

Figure 14:
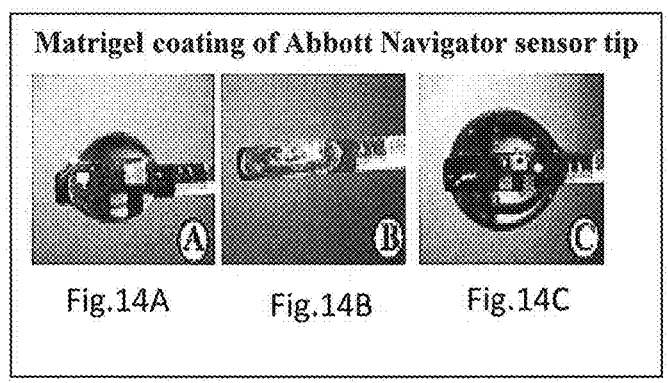
FIGS. 14A-14C are a set of photographs showing the 1) coating, 2) dehydration and 3) rehydration steps for coating a sensor with basement membrane.

In order to develop a protocol for matrix coating of glucose sensors that would allow a simple in vivo sensor implantation a coating and drying protocol was developed for coating the glucose sensors. In this Example, modified Abbott Navigator sensors were used. FIG. 14 contains photographs depicting cell culture derived basement membrane (Matrigel) coating of Abbott Navigator sensor tip combined contribution(s) of H-Angio and L-Angio to this enhanced CGM seen in Adv-VEGF treatment of the implantation sites.

The addition of Matrigel basement membrane to the Navigator sensors resulted in a simple "jelly-like" coating around the sensor (FIG. 14A). To assure that the Matrigel basement membrane coating would stay associated with the sensor during sensor insertion, the Matrigel coated sensor was air-dried overnight (FIG. 14B). The basement membrane coating on the sensors was then re-hydrated with $H_2O$ (FIG. 14C). The Matrigel basement membrane dried as an even coating, and was also able to rapidly re-hydrate. The rapid re-hydrating of the dry Matrigel on the sensor provided significant biocompatibility and a protective barrier around the implanted sensor, and also provided a flexible tissue response modifier delivery system. It should also be noted that with multi ECM layers involving coating and dehydrating there can be a significant accumulation of salt in the dried basement membrane. The final rehydration and drying cycle allows for removal of the excess salts from the multi-coated Matrigel, which may otherwise be toxic to the tissue.

Example 3—Impact of Basement Membrane on Glucose Sensor Function In Vivo

Once it was determined that Matrigel does not adversely affect functionality and sensitivity of the sensor in vitro (FIG. 15), the effect of Matrigel on sensor function in vivo was then determined (FIG. 16). For that, 15 ul of Matrigel (growth factor enriched) were added to the tip of the sensor and allowed to dry and then implanted as previously described. Sensors were implanted in the presence (Matrigel+sensor) or absence (buffer+sensor) of Matrigel. Immediately after sensor implantation, continuous glucose monitoring (CGM) was initiated using the mouse system. Sensor accuracy was further evaluated by calculation of the MARD. Non-Matrigel treated sensor had MARD values of 11.3% for the period up to 4 DPI and 38.0% for the CGM period of 4 to 14 DPI (FIG. 16A). The significant increase in the MARD value for non-Matrigel treated sensors was also reflected by the fluctuating sensor response not correlating with blood glucose levels (FIG. 16-A). MARD value for Matrigel treated sensor ranged from 7.6% to 6.6% for the testing period up to 4 DPI and 4 DPI to 14 DPI, respectively (FIG. 16-B). It is believed that Matrigel likely enhances sensor performance by protecting the sensor from biofouling.

In summary, these studies demonstrate that a bio-active membrane such as Matrigel can dramatically enhance sensor function in vivo. These studies also support the hypothesis that the uses of bio-matrices such as basement membrane increase the in vivo lifetime of an implantable glucose sensor. It should be noted that the data in FIG. 16 is compressed and as such the sensor response might appear as noisy signals. This is only an artifact of the presentation of the data over the 14-day time frame and due to the many data points obtained over this time frame (e.g. 1 data point/minute). Although the animals are not diabetic in these studies the mouse glucose level is still not stagnant (range for normal glucose level is 80-120 mg/dL) and the waves of glucose excursion can appear as noisy.

Example 4—Coating Glucose Sensors with Basement Membrane

In order to determine capability of layers of matrices on our sensors, 5 ul of 10 mg/ml Matrigel was added to the tip of a biosensor (Abbott Freestyle Navigator). Prior to Matrigel addition and immediately following Matrigel addition, sensors were tested in a 113 mg/dL buffered glucose solution. Additionally, the sensors were tested 12 hours post-Matrigel addition. For that, Matrigel was added to sensor tips and allowed to dry overnight. Sensors containing matrix Matrigel was allowed to re-hydrate for 30 minutes prior to testing in buffered glucose solution. It was found that sensor sensitivity remained unchanged in any of the tested conditions for both Nafion coated and Abbott Navigator sensor. To verify that Matrigel remains on the sensor tip rather than being stripped off once submerged in buffer or when adding additional Matrigel layers, pictures were taken at various Matrigel coating stages utilizing a dissecting microscope connected to a camera. FIG. 14A shows the sensor tip with the addition of 5 ul of Matrigel. FIGS. 14B and 14C shows the sensor tip after overnight drying of Matrigel on sensor tip and with re-hydration of Matrigel in $H_2O$, respectively.

Figure 15:
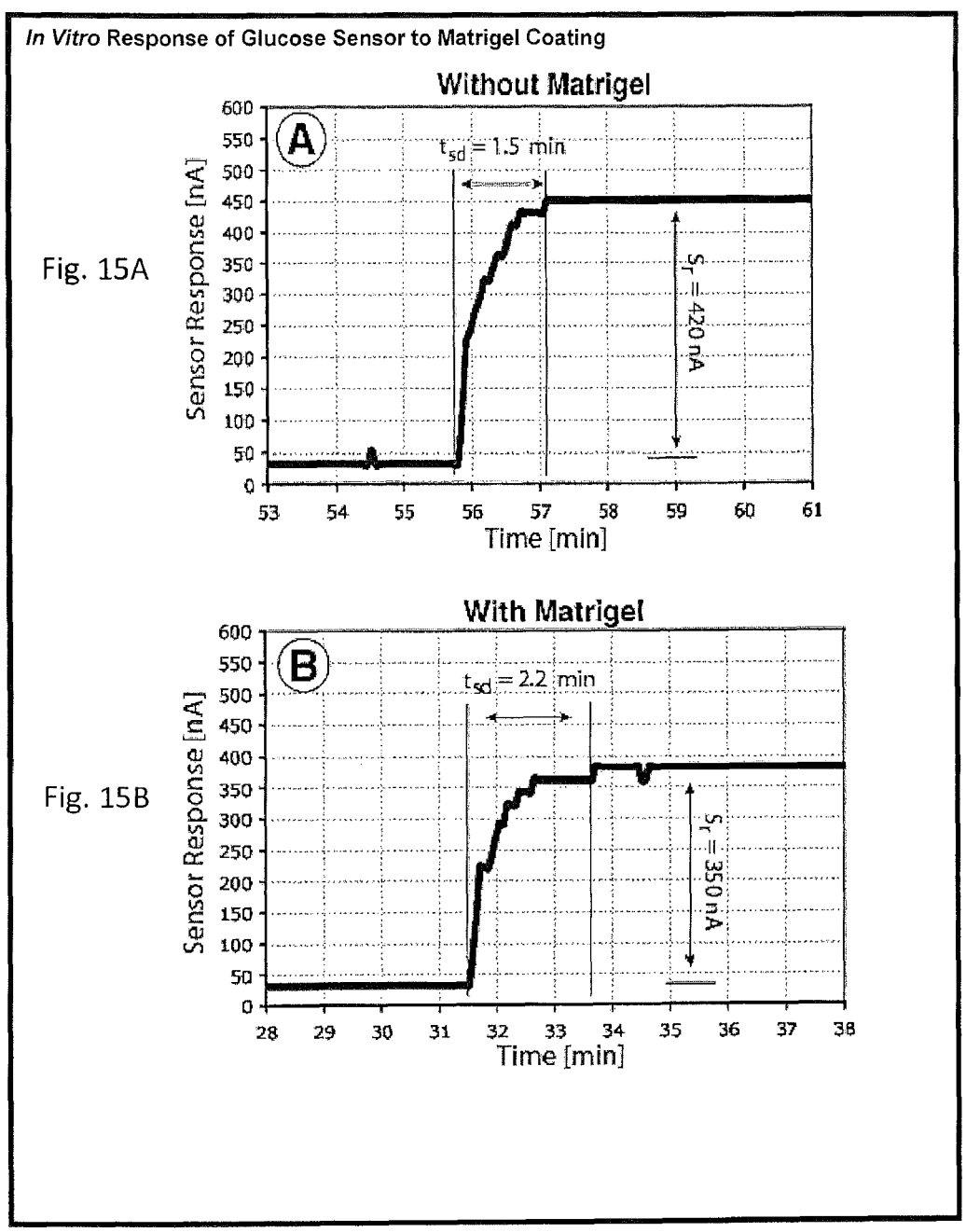
FIGS. 15A and 15B are graphs depicting an in vitro demonstration that coating glucose sensors with basement membrane does not reduce glucose sensor function when compared to non-coated sensors.

Example 5—Effect of the Basement Membrane on Glucose Sensor Function in Vitro To determine if matrix Matrigel is a physical barrier to glucose diffusion, the in vitro response of glucose sensors was determined with and without Matrigel coating. For these studies, glucose was added to the sensor (with or without Matrigel) after stabilization of the sensors in phosphate buffered saline (PBS), and sensor response was followed (FIG. 15). Next, the sensor was removed from the PBS/glucose solution, washed in PBS and then a Matrigel coating (10 mg/ml) was added to the working electrode of the glucose sensors. After polymerization of the Matrigel, the glucose sensors were retested at 37° C. as described above. Representative results are presented in FIG. 15, in which $S_r$ indicates the sensor response (e.g. sensor drift) and $t_{sd}$ indicates sensor delay. For these studies it was assumed that glucose addition to PBS resulted in a homogenous solution instantaneously (time delay=0). As can be seen in FIG. 15A there was no significant difference in the $S_r$ or $t_{sd}$ when we compared the Matrigel coated (FIG. 15B) versus sensors without Matrigel (FIG. 15A) coatings. This preliminary data supports the previous in vitro and in vivo data that supports the use of matrices such as Matrigel in enhancing sensor function.

Example 6—Impact of Basement Membrane on Glucose Sensor Function In Vivo

The effect of Matrigel on sensor function in vivo was determined. Prior to implantation sensors were treated with Matrigel. For that, 5 ul of Matrigel (growth factor enriched) were added to the tip of the sensor and allowed to dry. Two additional Matrigel coatings were added to the sensor with drying steps between each step. Sensors were implanted the day following Matrigel treatment. Sensors were implanted in the presence (Matrigel+sensor) or absence (buffer+sensor) of Matrigel. Immediately after sensor implantation, continuous glucose monitoring (CGM) was initiated using the mouse system. Glucose-derived current data were obtained at 60-sec intervals. Blood glucose reference measurements were obtained periodically over the 14-day implantation period, using blood obtained from the tail vein (~0.3 uL) and a FreeStyle Blood Glucose Monitor. First CGM of non-Matrigel treated sensors implanted in normal mice (CD-1) was evaluated. As can be seen in FIG. 16A, sensor output only shows one sensor drift at around day 3 in the first 6 DPI. However, at approximately 1-week post implantation the sensor experienced a sharp decline in sensor performance. Although a sensor signal is still being measured, it appears to be more random and it does not reflect the glucose level of the mouse (FIG. 16A). Alternatively, sensors treated with Matrigel prior to implantation performed exceptional during the entire 14-day testing period (FIG. 16B). Specifically, blood glucose levels for both sensors implanted in the mice generally ranged from 80 to 150 mg of glucose/dL of blood, with CGS current ranging from 1 to 9 nA for non-treated Matrigel sensors and 4 to 8 nA for Matrigel treated sensors. It appears that Matrigel enhances sensor performance by both protecting the sensor from biofouling as well as protecting the tissue surrounding the sensor from tissue toxic factor released from the sensor ($H_2O_2$ and gluconic acid). In summary, these studies clearly demonstrate that Matrigel can dramatically enhance sensor function in vivo. These studies also show that the uses of bio-matrices such as Matrigel with glucose sensors, dramatically increases the in vivo lifetime of an implantable glucose sensor.

Example 7—Usage of "Dry" Bio-Matrices to Deliver Adenovector Genes In Vitro

Figure 17:
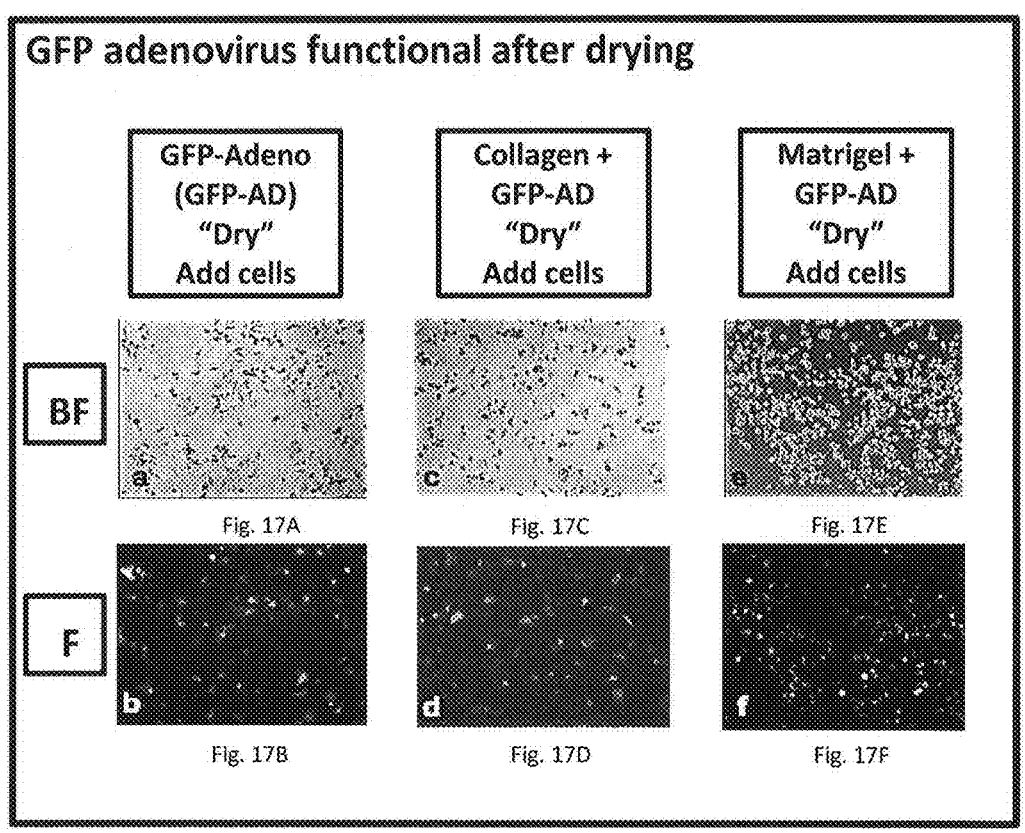
FIGS. 17A-17F are photographs showing that viral vectors used in gene transfer are protected from drying induced loss of function when encapsulated in ECM such as collagen or basement membrane when compared to viral vectors dried without matrices.

GFP-adenovirus was used as a gene transfer marker and indicator cells A375 to determine the ability of air dried/4° C. bio-matrices to release functional adenovirus. For these studies GFP-adenoviruses were added to buffer, Matrigel (10 mg/ml) or collagen (0.1%) at varying final concentrations (i.e. serial dilutions). 200 ul of each of the resulting solutions were added to individual wells of a 24-well plate and allowed to dry overnight at 4° C. The next day A375 indicator cells were added to each of the wells and allowed to adhere and were cultured overnight at 37° C. and 5% $CO_2$. As can be seen in FIG. 17A, C, E bright field photographs A375 cells were viable 24 hr post seeding to the wells. Additionally, under all conditions A375 cells were bright green when viewed under fluorescence microscopy (FIG. 17B, D, F), indicating that under all conditions adenovirus were viable and successfully transferred the GFP gene to the A375 cells. If the GFP adenoviruses were not viable after drying, the A375 cells would not have turned green under fluorescence microscopy. Analysis of the serial dilution results of these studies also indicated that the GFP-Adenovirus were 10-100× times more viable when GFP-adenovirus were dried in the presence of Matrigel or collagen when compared to drying in buffer only. These studies clearly support the concept that drying adenovectors in the presence of bio-matrices preserves virus infectivity. Thus, this supports the idea that "dry" adenovector-bio-matrices can be used to locally deliver genes that are important in controlling TRT at sites of sensor implantation. We anticipate that if we utilize lyophilization to dry matrices we will likely get even greater adenovector gene transfer, when compared to air-drying.

Example 8—Uses of "Dry" GFP-Adenovector/Bio-Matrix Coated Glucose Sensors to Deliver Genes to Cells In Vitro Since glucose sensors have different coatings than cell culture dishes and also contain glucose oxidase, which releases both $H_2O_2$ and gluconic acid as breakdown products of glucose, the cell culture studies described above were extended by coating Abbott Navigator sensors with GFP-Adenovirus/Bio-matrix coatings (Matrigel) and air drying them overnight at 4° C. The resulting Adenovirus/Bio-matrix coated sensors (Matrigel or collagen) were then placed in a cell culture dish, and media containing A375 indicator cells were added to the well. As can be seen in FIG. 18A (GFP-adenovector-Matrigel coating) and FIG. 18B (GFP-adenovector-collagen coating), air-drying of the GFP-adenovector in Matrigel or collagen remained functional. This is indicated by the ability of the GFP-adenoviruses to transfer the GFP to the indicator A375 cells in vitro. It should be noted that rehydration of the Matrigel by the media causes significant swelling of the dry Matrigel into a small "mound" around the sensor (see FIG. 14 above). Since Matrigel auto-fluoresces, the rehydrated Matrigel can easily be seen surrounding the sensor in the 10× photomicrographs in FIG. 18A. These sensor studies clearly demonstrate that adenoviruses can be dried in the presence of bio-matrices and remain functional. These studies support the feasibility of using dry bio-matrix coatings for local/targeted gene transfer studies at sites of glucose sensor implantation in vivo Example 9—Genetic Engineering and Gene Therapy Example 9A—Establishing hCAR Transgenic Mice Colony To expedite the adenovector studies, hCAR mice were obtained. Lymphocytes are known to have low levels of CAR and as such are not infectable with adenovectors. In order to confirm that lymphocytes derived from hCAR mice are infectable with adenoviruses, spleen cells were isolated and infected using an adenovirus carrying the gene for GFP. As expected, spleen cells from hCAR mice were infectable with GFP adenoviruses (FIGS. 19A and 19B), but control spleen cells from C57BL/J were not (see FIGS. 19C and 19D).

Example 9B—In Vitro Expression of mVEGF, hVEGF and hHGF by Mouse hCAR BM-ECP after Exposure to Adenovectors Containing Genes for Angiogenic Factors (AF)

Once it was established that hCAR derived lymphocytes were transfectable with GFP adenoviruses, AF expression was determined in bone marrow derived endothelial cell progenitors (BM-ECP) transfected with AF adenoviruses. The AF adenoviruses used for this study were mVEGF, hVEGF and hHGF. The controls for the AF studies were: 1) GFP adenovectors and 2) BM-ECP treated with control media (buffer). After transfection with the viruses or exposure to the control buffer, individual cell culture supernatants were obtained at various times post exposure. AF Expression (mVEGF, hVEGF and hHGF expression) in these supernatants was quantified by ELISA. Control BM-ECP cells were isolated from bone marrow from normal (non-hCAR) mice and treated in an identical fashion. BM-ECP isolated form normal mice (i.e. non-hCAR mice) did not produce any significant AF under any treatment condition (data not shown). Additionally, buffer and GFP-adenovirus treated hCAR BM-ECP also did not produce any significant AF in vitro (FIG. 20). Alternatively, hCAR BM-ECP exposed to the AF adenovectors produced rapid expression of the AF factors for all the adenovectors (i.e. mVEGF, hVEGF and hHGF transfected hCAR BM-ECP cells) see FIG. 20. Thus, the GFP and ELISA data clearly indicate that one can 1) infect ECP cells with adenovirus, and 2) that these infected cells clearly produce the specific AF's when exposed to AF adenovirus vectors in vitro.

Example 9C—hCAR Adenovirus Enhances Infectivity by Adenoviruses and Angiogenic Factor Expression Previous studies have demonstrated that increased expression of CAR on cell surfaces enhances adenovirus infectivity and resulting gene expression in cell. To test this possibility hCAR derived ECP were infected with adeno-GFP vectors with or without prior exposure to hCAR adenovirus.

Figure 21:
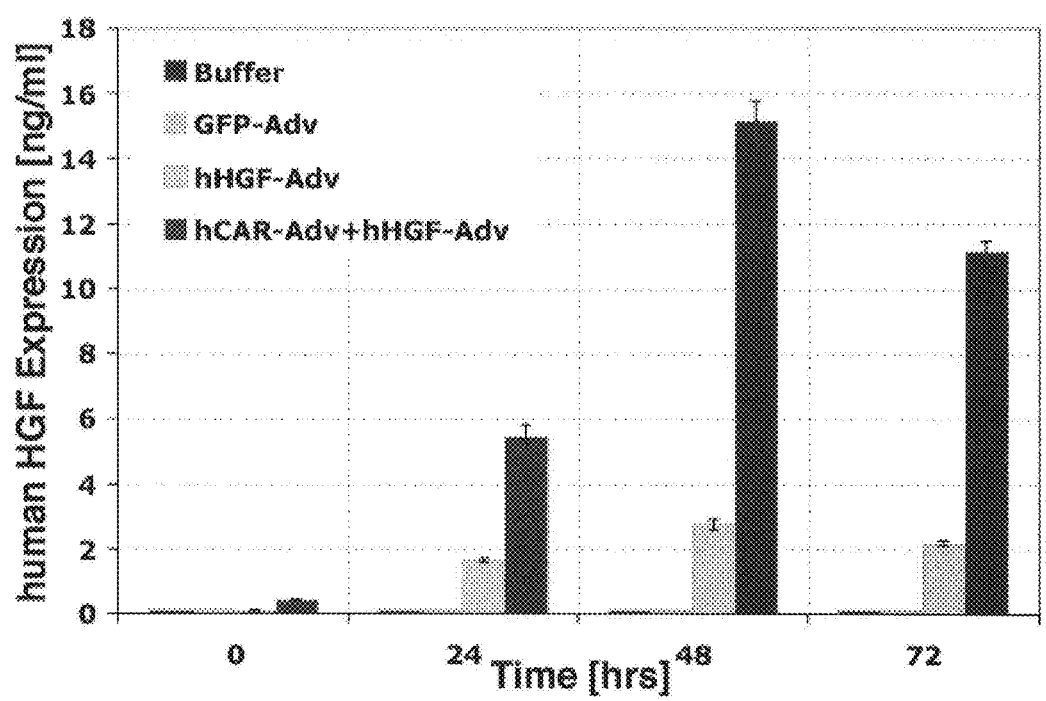
FIG. 21 is a graph showing that in vitro pretreatment of cells with hCAR followed by subsequent infections of these cells by other viral vectors (green fluorescent protein (GFP) or hepatocyte growth factor (HGF) dramatically increases expression of GFP and HGF when compared to cells not pre-treated with hCAR.

As expected non-adeno-GFP infected cells showed no fluorescence (FIG. 20B), cells infected with GFP-Adv (FIG. 9D) became fluorescent but cells infected with viruses GFP-Adv then hCAR-Adv display a dramatic increase in fluorescence (FIG. 20F). FIG. 20A is the brightfield control to FIG. 20B. FIG. 20C is the brightfield control to FIG. 20D. FIG. 20E is the brightfield control to FIG. 20F. This data clearly demonstrated that the hCAR adenovirus is a potent enhancer of Adenovirus infectivity and gene expression likely as a result of allowing super infection of the target cells. To extend these studies the ability of pre-infection of target cells with hCAR adenovirus was determined in order to determine enhanced angiogenic factor expression for these cells. hCAR derived BM-ECP were treated with 1) buffer, 2) GFP-adenovirus, 3) HGF-Adenovirus or 4) hCAR-adenovirus followed by exposure to hHGF-adenovirus. hHGF expression was only detected in the hHGF infected BM-ECP cells (FIG. 21). Cells infected with hCAR-adenovirus plus hHGF-adenovirus displayed a 3 to 5-fold higher hHGF expression when compared to the hHGF-adenovirus infected cells. The peak hHGF production by hCAR-hHGF cells in vitro was 48 hrspost infections with 15.2 ng/hHGF/ml versus 2.8 ng/hHGF/ml for hHGF cells not previously treated with hCAR (FIG. 21). No hHGF protein production was seen in cells treated with buffer or GFP (FIG. 21). The ELISA data clearly indicates that BM-ECP cells treated with hCAR in addition to hHGF significantly enhances angiogenic factor expression.

Example 10—P39 Adenovirus Enhances Angiogenic Factor Expression

Figure 22:
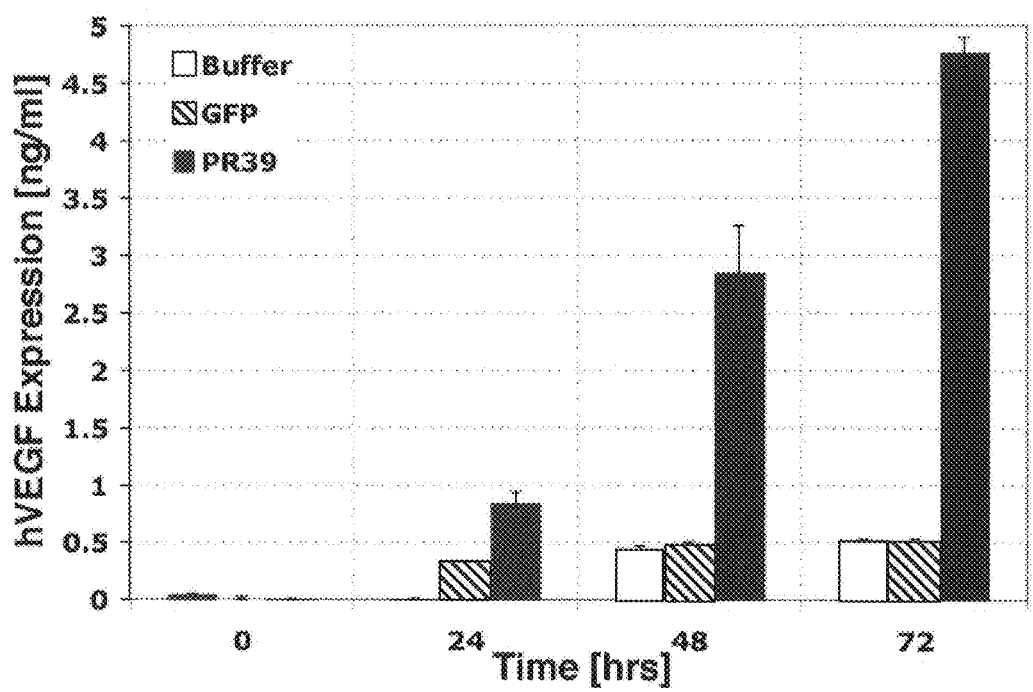
FIG. 22 is a graph showing that in vitro cells pretreated with the adenoviral vector for PR-39, which selectively induce enhanced expression of endothelial cell vascular growth factor (VEGF) expression in human A375 cells. This PR-39 induction of VEGF would induce increased vascular networks at sites of medical device implantation.

To determine whether PR39 adenovirus is able to enhance angiogenic factor expression, i.e. VEGF, human A375 cells were treated with buffer, GFP-adenovirus or PR39-Adenovirus, and VEGF expression determined by ELISA analysis of the resulting cell culture supernatants. Since A375 cells are human cells, they naturally express low levels of VEGF at baseline (buffer) and control (GFP-adenovirus) (FIG. 22). However, A375 cells infected with adenovirus carrying gene for PR39 significantly enhanced hVEGF expression by 2.7 fold 24 hours post infection, 6.1-fold 48 hours, and 9.1-fold 72 hours post infection with PR-39. The peak hVEGF production in vitro was 72-hours post infection and 4.8 ng/hVEGF/ml versus 0.5 ng hVEGF/ml in A375 cells treated with either buffer or GFP (FIG. 22). The data clearly indicate that PR39 can induce VEGF expression in cells likely by inducing the HIF-1a pathway resulting in expression of the potent angiogenic factor VEGF.

Example 11—HCAR Adenovirus Plus P39 Adenovirus Enhances Angiogenic Factor Expression in Mouse Fat Cells For these studies, mouse fat cells were plated at identical numbers ($10^6$ cells/well) and incubated with the various Adv of buffer for 24 hr., then the cells were washed and fresh media was added. At 24, 48 and 72 hr. post incubation the culture media was removed and assayed for mouse VEGF by ELISA. As can be seen in FIG. 23A the mVEGF-AdV induced significantly higher mVEGF expression (Approximately 200 pg/ml by 72 hrs.), where the levels in both GFP-AdV and buffer treated cells was virtually undetectable (FIG. 23C). The results of these studies clearly demonstrate PR-39-peptide AdV to induce mVEGF expression (Approximately 200 pg of mVEGF/ml by 72 hrs.), in the mouse fat cells (FIG. 23B). Finally, since cells that carry the AdV receptor CAR (see background) can not only be infected by Advs but with increased expression of CAR can be super-infected by multiple Advs. Therefore, we determined that if fat cells are pre-infected with Adv that expresses hCAR that we would get higher expression of hCAR on the surface of the cells which would allow even greater infection by another AdV, i.e. PR-39. As can be seen in FIG. 23C, pre-incubating the mouse fat cells with the hCAR Adv resulted in a super induction of mVEGF in the same mouse fat cells (i.e. nearly 800 pg of mVEGF/ml of media), nearly 4 times the levels of mVEGF induced by mVEGF-Adv or PR-39-AdV alone (FIG. 23C). Combined mVEGF-AdV plus PR-39 AdV mVEGF expression levels seen in FIG. 23C, were over twice the additive levels of mVEGF-AdV plus PR-39-AdV thus supporting the possible synergy in gene expression when hCAR expression is induced on cell surfaces. Thus, hCAR-AdV can be used in combination with other AdV to enhance gene expression directly in vivo or as part of genetically engineering cells in vitro for in vivo use.

Prophetic Example 12

Fibronectin (FN) can be used as a crosslinking agent for extracellular matrix (ECM) such as basement membranes and collagen to hold the basement or collagen together (make ECM stronger). FN can be first coated on the device (acting as an adhesive), and then ECM can be added to stick the ECM to the devices more tightly/stronger. FN can be added as a coating at any stage of the coating process and even can be used during one of the hydration steps in the form of a solution. FN can be used as an adhesive between layers with or without hydration steps.

Drying steps with FN and other ECM are believed to increase the crosslinking of FN to ECM. Also the drying step can increase the tightness by which additional factors such as cytokines, chemokines, growth factors and inhibitors of inflammation and fibrosis (CGFI) bind to the FN and the other ECM present in the coating layers Because of the ability of FN to bind various peptides and proteins, it can be utilized as a drug delivery system when it is added into the extracellular matrix. For example, FN can be added to basement membranes containing factors, and then the factors are released from the ECM in order to benefit the surrounding tissue, such as by inducing vessel formation, suppressing inflammation and suppressing fibrosis.

It is believed that the "dry" matrices may actually be more efficient in retaining proteins and peptides (i.e. slower release kinetics) when compared to the "wet" matrices. Factors such as cytokines chemokines, growth factors antibodies recombinant proteins as well as inhibitors of inflammation and fibrosis can be cross-linked directly to the matrix using a cross-linking agent. Factors also can be indirectly crosslinked to the extracellular matrix using fibronectin or fibronectin related peptides that bind to fibronectin (i.e. fibronectin binding domains or peptides fragments of fibrin, collagen or RGD peptides). The fibronectin molecule or fragments act as a bridge to link the various CGFI to the various bioactive matrices (see FIG. 25).

Additionally, CGFI often bind to matrices as a mechanism for long-term localization of these factors in tissue sites (e.g. wounds and ulcers). Generally, these bound factors interact directly with cells that are in contact with the matrix itself. This solid phase activation of cells is frequently referred to, as "you are what you sit on." It is believed that having rapidly releasing factors (e.g. anti-inflammatory) working together with slow releasing or bound factors is beneficial to control delayed tissue reactions such as fibrosis and neovascularization.

It is believed that rapidly releasing anti-inflammatory factors such as IL-10, IL-1ra, and sTNFR are useful in stopping inflammation, where as anti-fibrotic agents such as P144, sTGFR or anti-CD40 are most useful in a delayed release or even remain bound to the matrix, thereby inactivating in-fluxing fibroblasts and suppressing fibrosis. Additionally, late releasing angiogenic factors are expected to be useful in promoting angiogenesis at a later time frame, i.e. after the inflammatory reactions. Factors such as hepatocyte growth factor (HGF) have an impact on the tissue reaction triad (TRT) of inflammation fibrosis and vessel regression at sites of sensor implantation shown by suppressing both inflammation and fibrosis, as well as promoting angiogenesis. It is believed that the 2-peptide systems (PR39 and P144) have a significant impact on TRT related cell activation. The release profiles for the various factors under both wet and dry preparation is different. It is expected that the dry protocols will result in matrices that bind larger amounts of factors and retain them for longer periods once they are dehydrated.

It is known that a number of factors can exert their biological action when incorporated into Matrigel, collagen or fibrin e.g. VEGF, FGF, PR39. It is expected that as the concentration of the individual matrix is increased, its total binding capacity also increases, and its rate of factor release decreases. Matrigel (BD Biosciences) is expected to be a particularly effective wet or dry matrix for these embodiments. Each of the component matrices of Matrigel has specific binding sites for numerous factors and receptors (either on cells or free as soluble receptors). It is expected that fibrin matrix is particularly effective in delivering factors that control inflammation (IL-10, IL-1ra and sTNFR) and fibrosis (e.g. P144, sTGFR, anti-CD40 and HGF). It is expected that a mix of Matrigel plus fibrin with the various factors provides a good combination of matrix strength with a wide range of binding capacities for the various candidate factors (see FIG. 25). The addition of fibronectin to the Matrigel-Fibrin combination matrix would add even more tensile strength as well as additional diversity of factor binding capacity.

Figure 25:
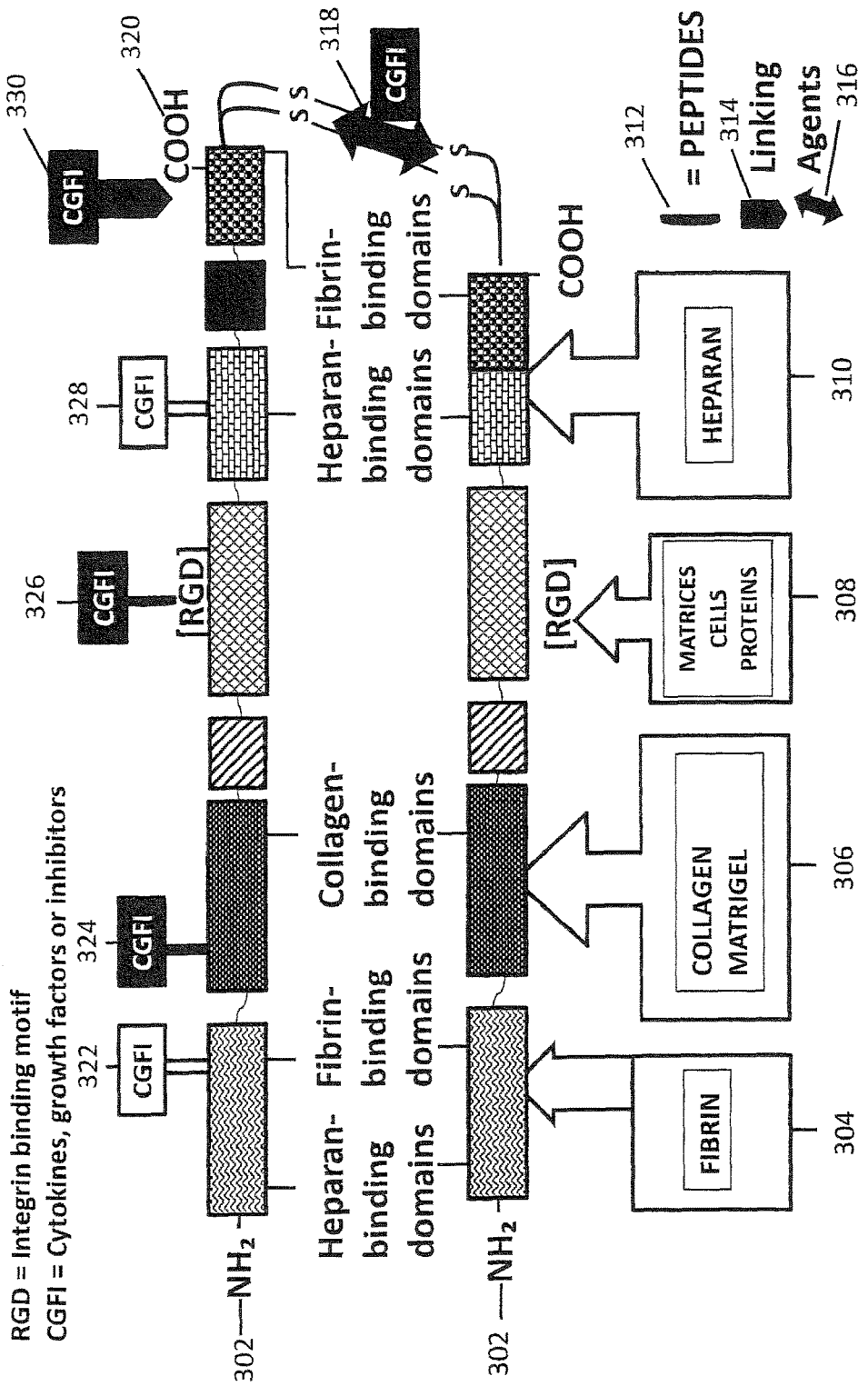
FIG. 25 depicts embodiments using fibronectin as a crosslinking agent for ECM in vitro and in vivo as well as demonstrating possible sites on the fibronectin molecule for binding of tissue response modifiers including cytokines/chemokines, growth factors and inhibitors of inflammation and fibrosis, as well as associated methods to link these agents to the fibronectin.
Figure 36:
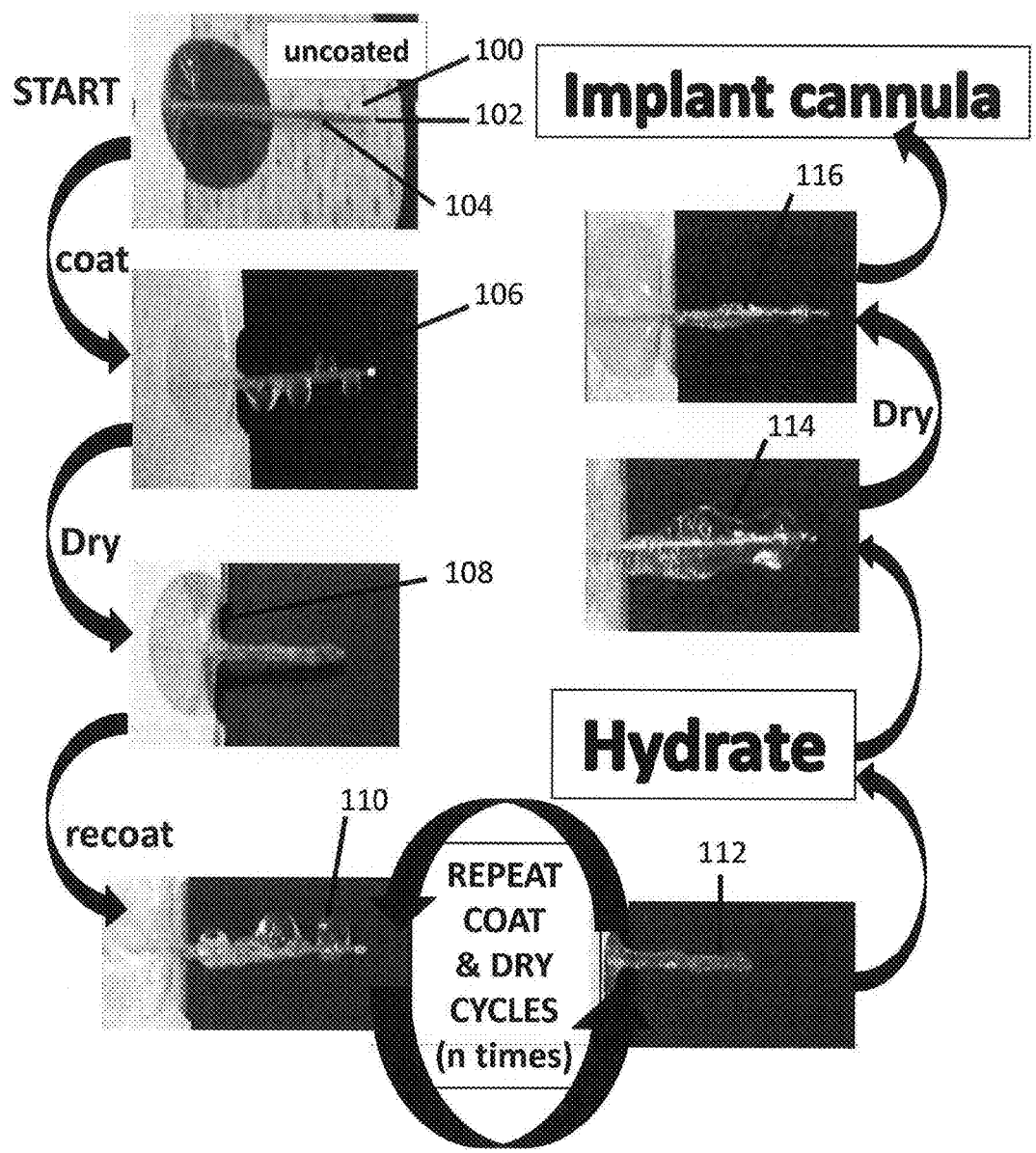
FIG. 36 depicts a demonstration of methods to create a multi-ECM layered cannula sleeve for an insulin infusion cannula using multiple coating, dehydration and rehydration steps/methods.

In one embodiment, the various CGFI are either coupled to collagen/fibrin heparin or integrin binding peptide sequence (RGD) peptides using commercial cross-linkers (Pierce Chemical) and then added to fibronectin, which in turn will bind the CGFI-peptide complex (FIG. 25). The CGFI-peptide fibronectin complex is then added to Matrigel, fibrin and or collagen, to which it binds (FIG. 25). The resulting CGFI-peptide-fibronectin-matrix complexes are used in vivo to establish a very controlled distribution of the CGFI with the matrix. Since fibronectin has both COOH and disulfide cross-linking the CGFI it can be chemically cross-linked thru these residues (FIG. 36). Because CGFI normally interact in vivo with the various bio-matrices used it is extremely likely that all the factors will be functionally active. The kinetic of release of the various factors must also be considered in choosing the appropriate combinations. Generally, one would expect that rapidly releasing anti-inflammatory factors such as IL-10, IL-1ra, and sTNFR would be useful in stopping inflammation, while anti-fibrotic agents such as P144, sTGFR or anti-CD40 would be most useful if they showed delayed release or even remain bound to the matrix, thereby inactivating in-fluxing fibroblasts and suppressing fibrosis. Additionally, late releasing angiogenic factors would likely be useful in promoting angiogenesis at a later time frame, i.e. after the inflammatory reactions.

It is expected that the dry protocols will result in matrices that bind larger amounts of factors and retain them for longer periods once they are dehydrated.

FIG. 25 is a diagram of the FN molecule with its distinct "backbone" (102), showing ways in which FN can bind with a variety of matrices (104-110) and factors (122-130) at specific binding sites within the FN structure. The ability of FN to bind matrices such as basement membrane, fibrin, collagen etc. (104-110) allows FN to be an effective biologic crosslinking agent. Since FN has a specific binding site for heparin, it can also bind a number of factors that are tissue response modifiers, such as VEGFs that induce new vessel formation in injured (TRMs). This binding can be the result of the structure of the molecule such as heparin (110) or through common peptide sequences such as integrin binding peptide (RDG) sequences (108). Additionally, various peptides known to bind to FN can act as a bridge or crosslinking agent (126).

Additionally, other peptides and various chemical cross-linking agents (114 and 116) can bind factors such as cytokines, growth factors and inhibitors to the FN backbone. Alternatively, because FN has reactive elements such as sulfhydryl's (118) and COOH groups these can be derivatives to allow covalent linking of various TRMs to the FN molecule. Ultimately, with the degradation of FN in vivo a wide variety of TRMs will be released from the FN derivatives.

It should be noted that the modified FNs described above will have at least one modification per FN molecule, and can be used individually or in any combination or ratio of modified and/or unmodified FNs.

Embodiments of FIGS. 26-37

FIG. 26A shows a sensor assembly with a collar. The sensor assembly 400 includes electronics 402, a sensing element support 406 with a sensing element at the tip 408. The sensor is covered by a polymer to prevent influx of interfering substances into the sensor sensing element 404. When a sensor is implanted into the skin as shown in FIG. 26C, it creates an open wound 410 with a risk of infections 412 as well as dampness to the upper skin cell layers (e.g. epithelial cells). For the sensor in FIGS. 26B and 26D, the sensing element support 406' has an antimicrobial collar 414 configured to be positioned on both sides of the point at which the support enters the tissue 410. A coating 412 containing no additives, or tissue response modifier, such as those listed above, can be included within the collar or disposed between the collar 414 and the sensing element 406'. This configuration prevents infection and inflammation that otherwise may occur, as shown in FIG. 26C, within the tissue around the sensor and support due to, e.g., bacteria 413. While the coating 414 usually is rehydrated (see 430) after implantation to minimize discomfort to the patient, the coating 422, 428, 432 on the coated sensor (416, 418 and 420 in FIG. 26B) also can be rehydrated before implantation. In embodiments, the coating can be applied immediately before assembly, in which case initial dehydration would not be required.

Figure 27:
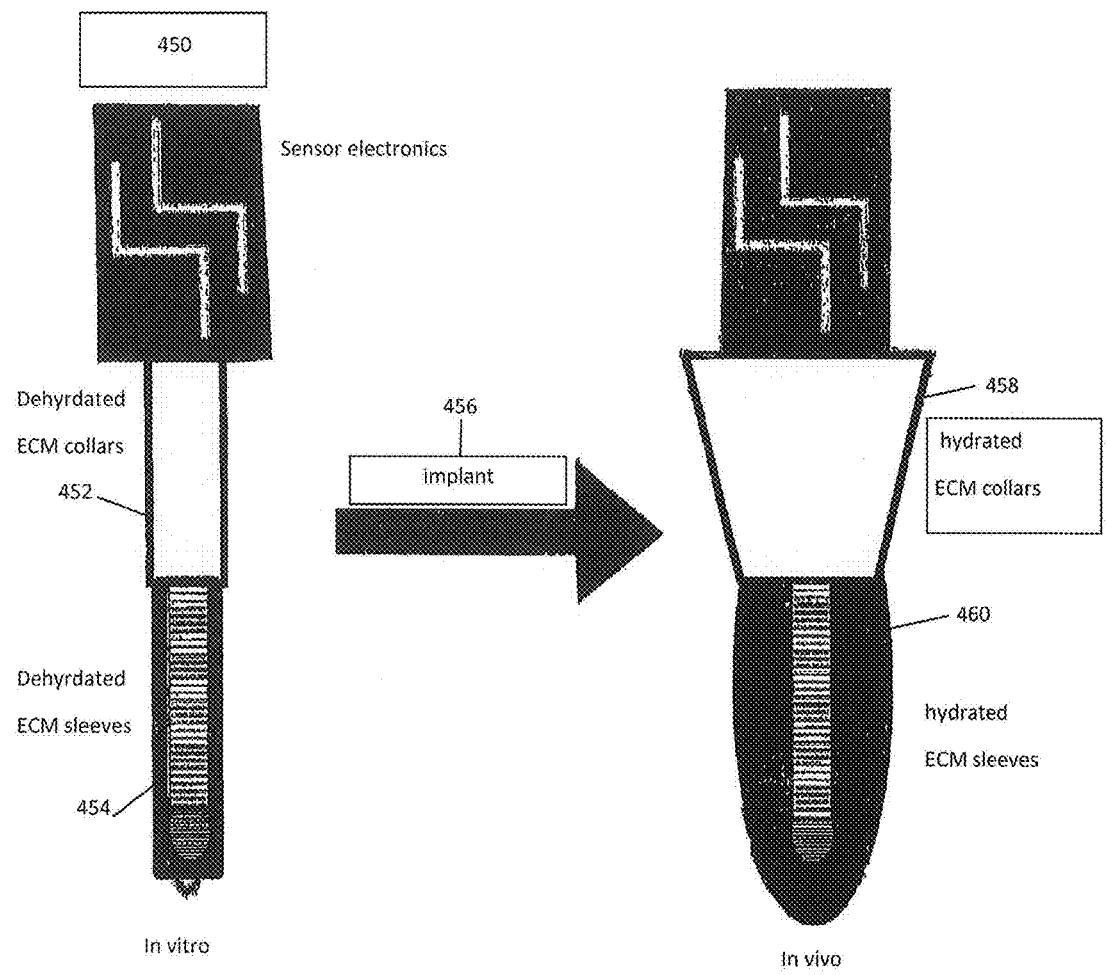
FIG. 27 shows an embodiment of a method for creating ECM collars and sleeves on a glucose sensor for use in implantation into a mammal.

FIG. 27 shows the rehydrated version of the sensor assembly 450 with the coating 452,454 completely surrounding the implanted portion of the sensor assembly 450. In this embodiment, there are no additives added to the collars or sleeves, but the collars 452 and sleeves 454 act here as mechanical plugs to prevent infection and "shock absorbers" to prevent tissue damage as a result of mechanical movement of the implanted sensor in the skin. Generally, the collars and sleeves are dehydrated prior to implantation for ease of implantation for the patient and the clinician. The collars and sleeves can be hydrated pre sensor implantation if advantageous. In this embodiment, both a collar and sleeve coating are included in this compound device and are shown in hydrated form as 458 and 460, respectively.

Figure 28:
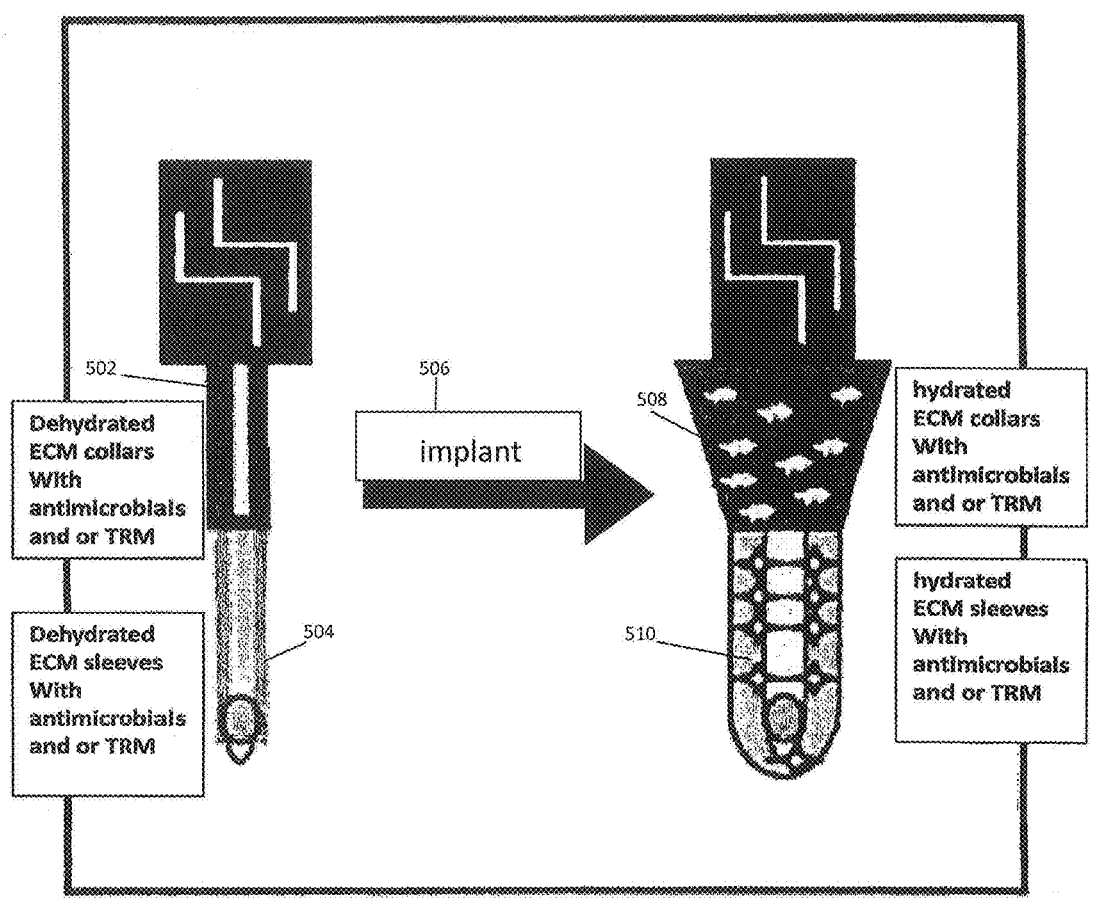
FIG. 28 shows an embodiment incorporating anti-microbial agents and tissue response modifiers into ECM based collars and sleeves for use on a glucose sensor.

FIG. 28 shows that ECMs with and without anti-microbial agents and TRMs can be incorporated into the ECM collars 502 and sleeves 504 as part of the cycles of coating, dehydration, rehydration and dehydration. When hydrated pre or post sensor implantation the anti-microbial agents and/or TRMs are released for the hydrated collars 508 and sleeves 510 and control infection inflammation, wound healing and fibrosis at the implantation site.

Figure 29:
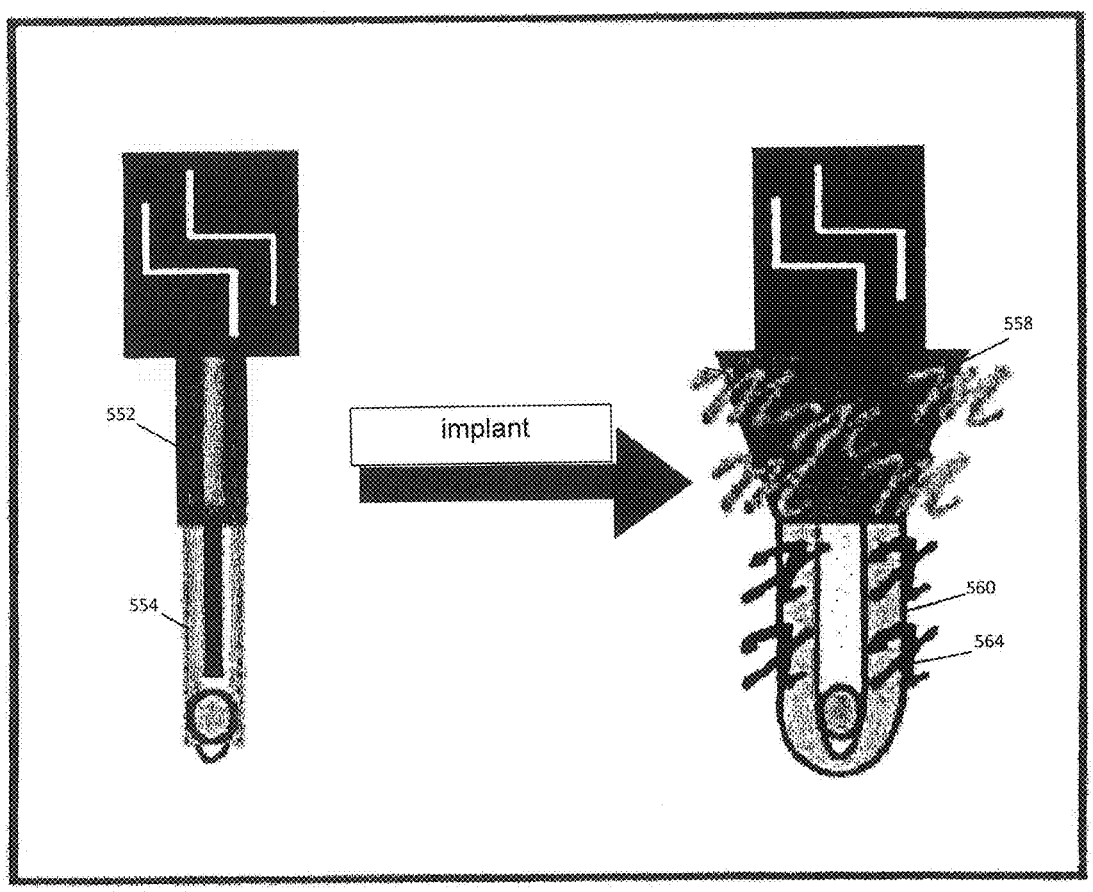
FIG. 29 shows an embodiment of tissue reactions induced by tissue response modifiers incorporated into ECM collars and sleeves when implanted into a mammal.

FIG. 29 shows that TRMs can be incorporated into the collars 552 and sleeves 554 pre-implantation. This incorporation can induce proliferation of skin surface cells 562 or blood vessels 564 to overcome tissue damage at the implantation sites. As such, sensor function is maintained or even enhanced due to maintaining tissue integrity and in growth of blood vessels, which assures real-time blood glucose determination by the glucose sensor.

Figure 30:
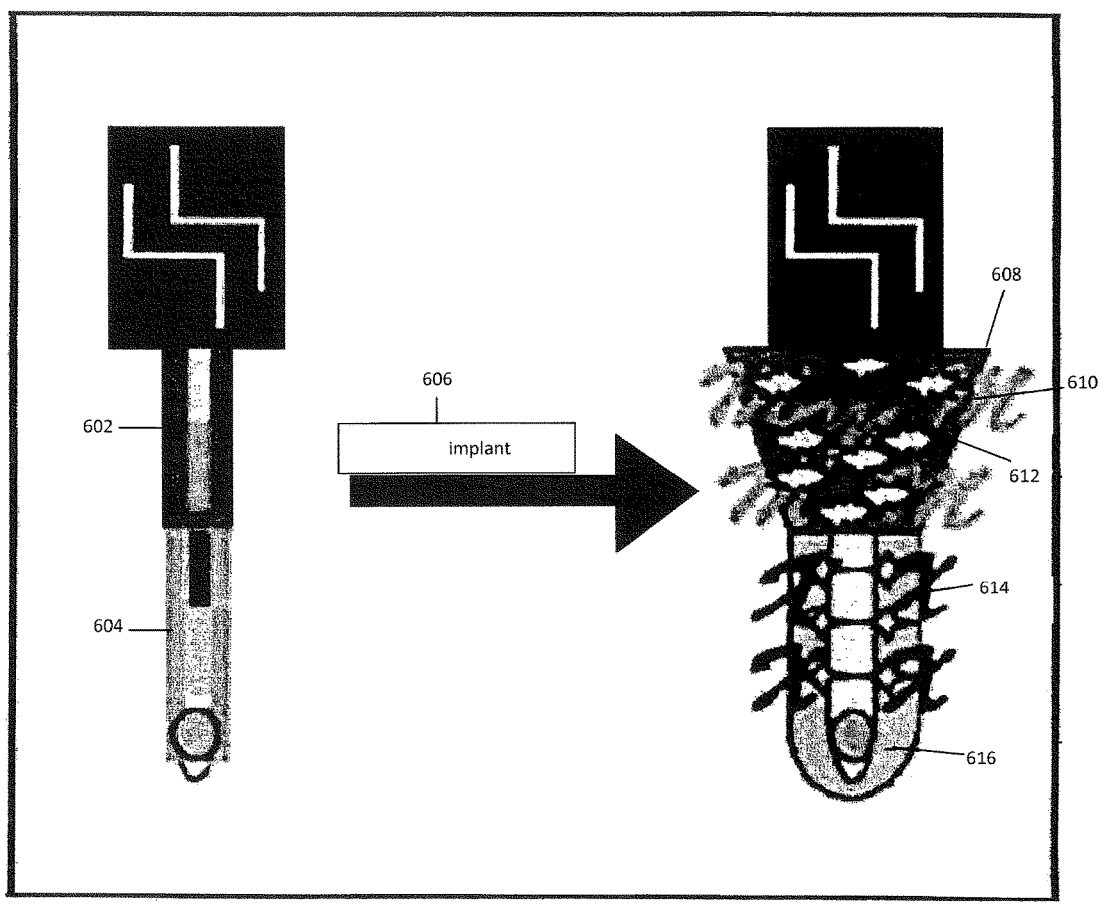
FIG. 30 shows an embodiment with tissue reactions induced by multiple tissue response modifiers incorporated into ECM collars and sleeves when implanted into a mammal.

FIG. 30 demonstrates that multiple anti-microbial agents and TRMs can be incorporated in the collars and sleeves to achieve maximal positive impact on preventing infection, tissue trauma, inflammation, and in promoting wound healing and neovascularization. Dehydrated collar 602 is hydrated to form hydrated collar 608. Dehydrated sleeve 604 is hydrated to form sleeve 616. As with the embodiment of FIG. 29, this can induce proliferation of skin surface cells 610 or blood vessels 614 to overcome tissue damage at the implantation site.

Figure 31:
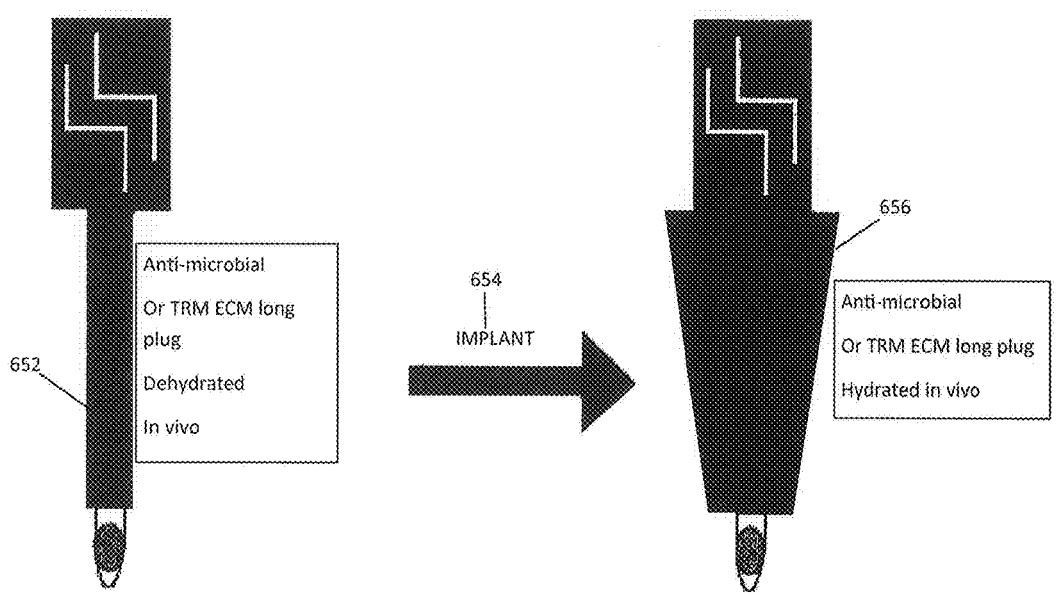
FIG. 31 shows an embodiment of a design of an extended collar for use in the dermis and subcutaneous tissue of a transcutaneous device i.e. glucose sensor.

FIG. 31 demonstrates that collar length can be extended to maximize anti-microbial and TRMs delivery at the implantation sites to various depths in the tissue. This also demonstrates that the collars 652 (hydrated at 656) can be extended into the tissue, not just on the surface to maximize the mechanical "plug" effect and thereby decrease infections as well as mechanical damage to the upper layers of the skin. This extended collar assures continuity from the surface of the implant site into the depth of the implanted tissue.

In embodiments, an extended collar has a length of 2 to 50 mm, or 5-20 mm, or 2-10 mm. The diameter at the larger end of the plug typically is in the range of 3-20 mm, or 5-15 mm, or 5-10 mm. In embodiments, a collar that is not "extended" has a length of 2-10 mm, or 2-7 mm, or 3-5 mm. The diameter at the larger end of the plug typically is in the range of 3-20 mm, or 2-7 mm, or 3-5 mm.

Figure 32:
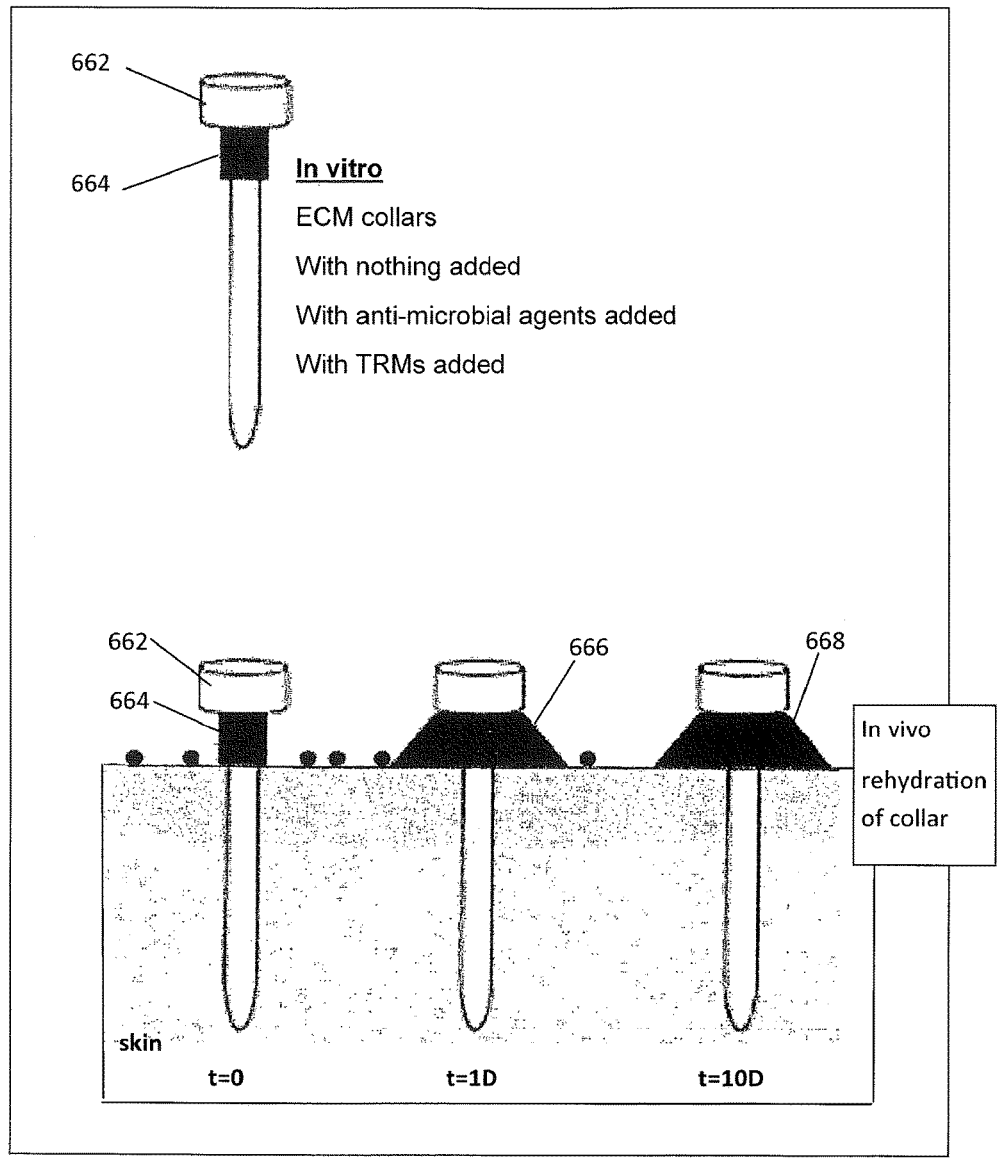
FIG. 32 shows an embodiment of ECM based collar for uses on a cannula or catheter with and without incorporation of anti-microbial agents and tissue response modifiers and its use in mammalian skin.

FIG. 32 demonstrates the impact of placement of a collar 704 around an infusion cannula 702 with and without additives. This cannula with a collar can be hydrated pre or post implantation, and provide a wound "plug" 710, 712 to prevent infection and tissue trauma. The addition of various antimicrobial agents and TRMs further prevent infection, inflammation and fibrosis and promote healing of the implantation sites both at upper layers (epithelial lay) as well as the dermis and subcutaneous tissue.

Figure 33:
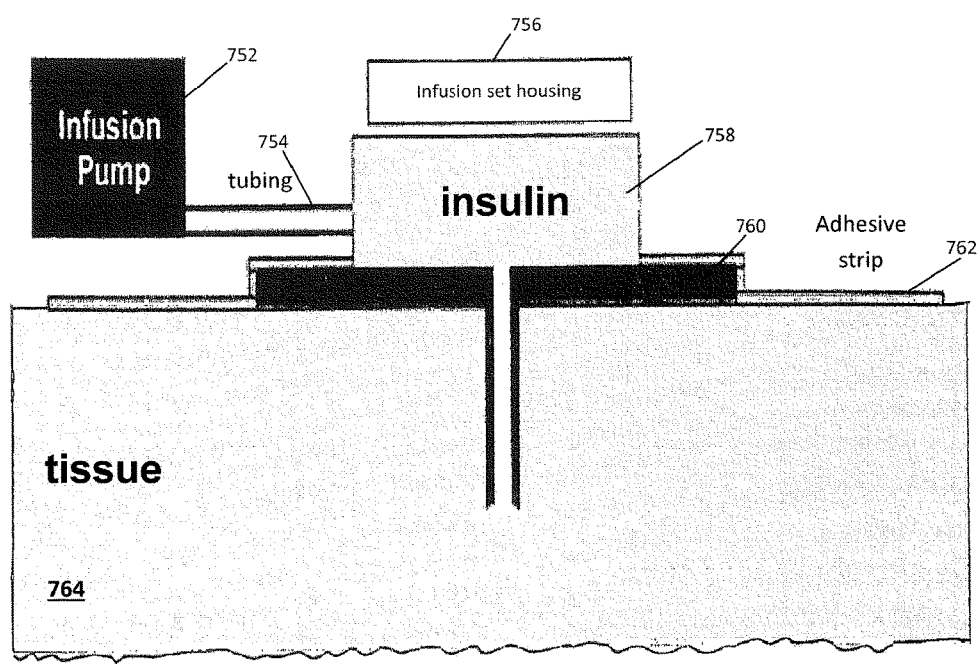
FIG. 33 shows an embodiment of an infusion set with transcutaneously inserted cannula but without ECM based collars or sleeves.
Figure 34:
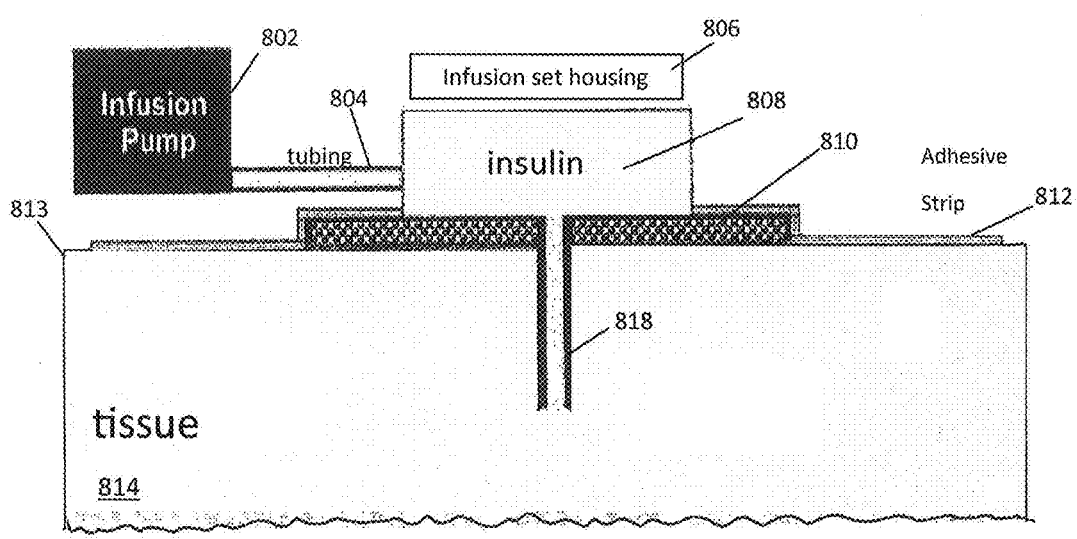
FIG. 34 shows an embodiment of an infusion set with a transcutaneously inserted cannula with ECM based collar between cannula and skin.

FIG. 33 shows an infusion system with an infusion pump 752 having tubing 754 connected to an infusion set housing 756, which includes an insulin supply/reservoir (usually to seal tube 758) frequently there is an inert cannula support (758 and 760) as well as an adhesive strip 762. This configuration does not include a collar. In FIG. 34, a one-piece collar-sleeve combination 810 is disposed on the outer surface of the tissue 814 in which the cannula is implanted. Again, an adhesive strip 812 holds the cannula in place on the outer surface 813 of the tissue 814. The infusion set cannula is inserted into the skin using a needle (which is inside the cannula) to pierce the skin, thereby allowing the cannula to move into the underlying skin layers using minimal force. Once implanted, the needle is removed and the infusion set is connected to the pump via a long plastic tubing. Once the tubing is connected to the infusion pump fluids can be infused into the tissue or vessel as needed.

Figure 35:
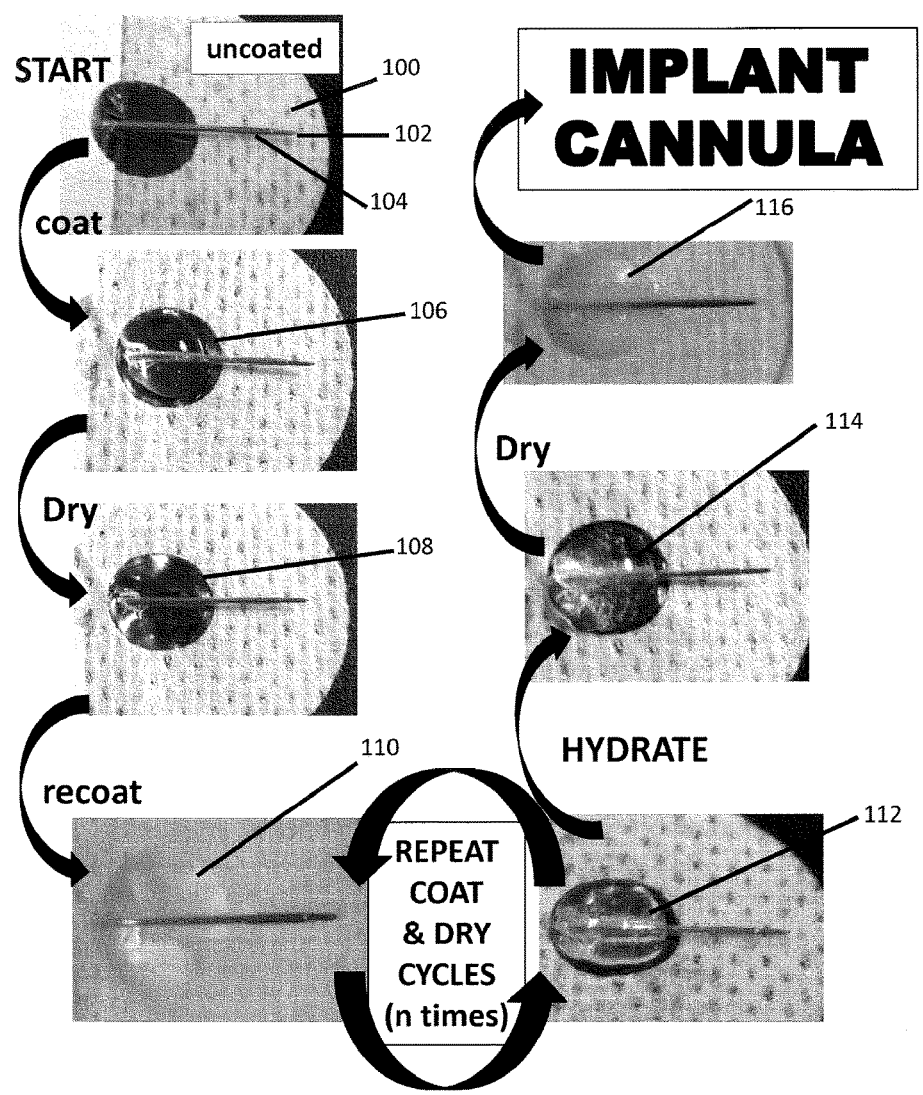
FIG. 35 depicts a demonstration of methods to create a multi-ECM layered collar for an insulin infusion cannula using multiple coating, dehydration and rehydration steps/methods.

FIGS. 35-36 show photographs demonstrating the application of coatings in accordance with embodiments described herein. The method is described above in connection with sensors.

Figure 37:
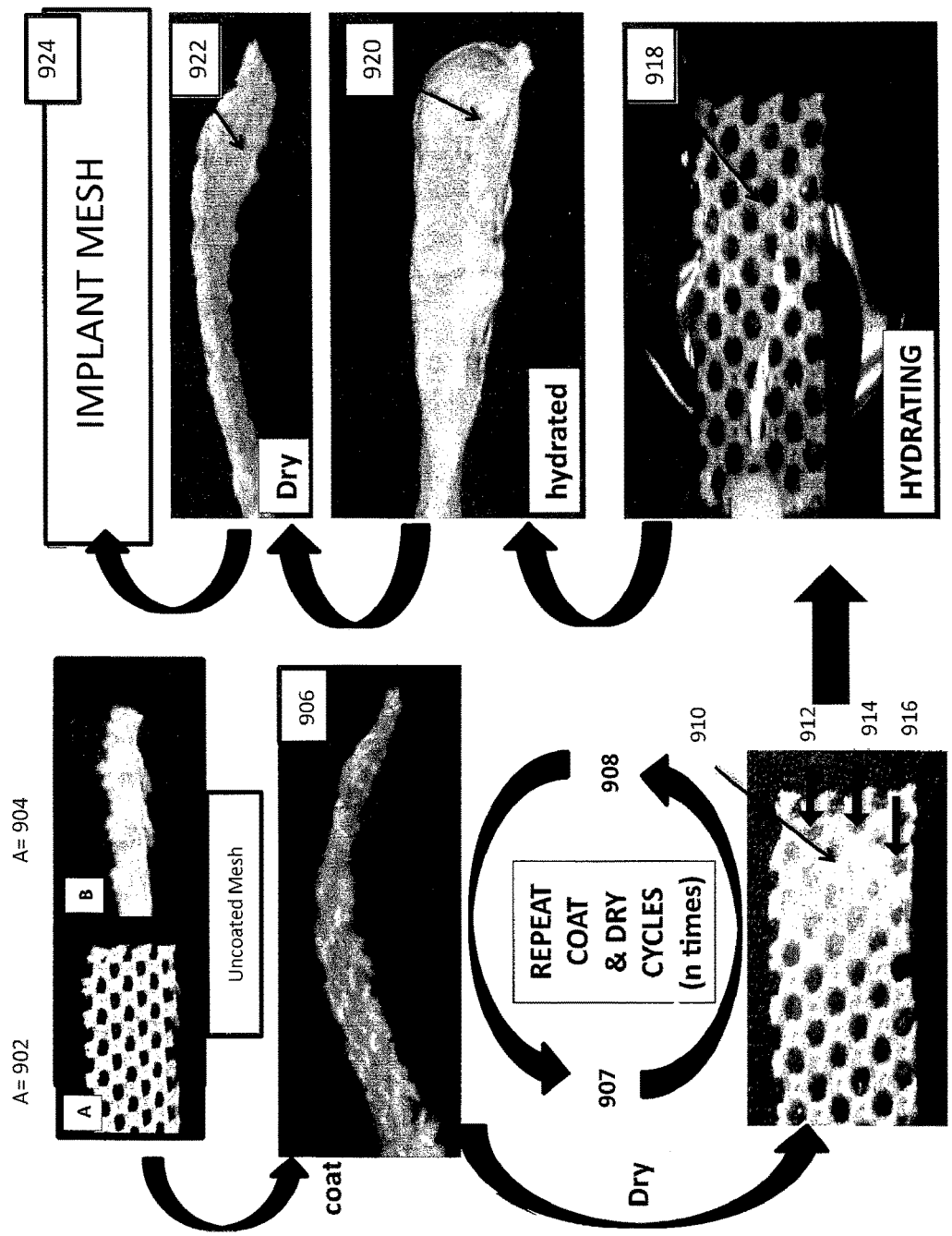
FIG. 37 depicts a demonstration of method to create a surgical mesh having a multi-ECM layered coating thereon that is applied using multiple coating, dehydration and rehydration steps/methods.

FIG. 37 describes the procedure to multi-coat surgical meshes that are used in reconstructive surgery including hernia surgery. For this procedure, surgical mesh (902 and 904) is obtained from a medical supply house, sterilized and placed in sterile containers. The mesh is suspended in a laminar hood to assure sterility. Next the mesh is dip coated by immersion in ECM, in this case in basement membrane (Matrigel) solution and suspended in the laminar flow hood to allow drying 906. The BM coated mesh is next allowed to dry, followed by repeated cycles of addition of BM and drying (907 and 908). After at least 1 cycle (in this case shown in the photographs there were 10 cycles of coating and drying), the coated mesh was rehydrated 918 in water to remove accumulated salts 920 and then allowed to dry 922. It should be noted that the coating not only covers the mesh fibers 910 but also fills the mesh pores 912, 914. Filling these pores likely will increase the biocompatibility of the surgical mesh when implanted in vivo. After drying, the coated mesh can be directly implanted in a patient or animal who need this type of mesh, or it can be rehydrated and then implanted in vivo.

Modified Basement Membrane Preparations

In embodiments, salts, glucose, individual amino acids, vitamins, and other low molecular weight components can be removed from the basement membrane to form a modified basement membrane preparation before it is coated on the device. These components can be removed from the basement membrane-media combination by a suitable technique depending upon the size of materials to be removed. Techniques for removing the low molecular weight materials include, but are not limited to; dialysis, buffer exchange, diafiltration, precipitation, gel filtration, affinity chromatography and electrophoresis. If this type of process is used, it is not necessary to rinse the basement membrane at the time of rehydration. Depending on the final use of the basement membrane, the separation technique can involve a suitable molecular weight cut-off. In embodiments, this cut-off might be 2000 daltons, or 10,000 daltons, or another value.

In this embodiment, the dehydrated modified basement membrane can be rehydrated using a liquid injected before or after the basement membrane-coated device is inserted in biological tissue, or the interstitial fluid themselves can hydrate the basement membrane.

FIG. 38 is a flow chart showing one embodiment for preparing a modified basement membrane preparation. The steps shown on the flow charts are described below in Example 13.

FIG. 39 shows formulations of two types of media used in making basement membranes sold commercially. The commercially available basement membrane are sold in a form in which they have already been placed in media, such as, but not limited to RPMI1640 from Sigma Chemical Co. or Dulbecco's Modified Eagle's Medium (DME) from Sigma Chemical Co. RPMI-1640 contains inorganic salts, amino acids, vitamins and other materials. The inorganic salts include calcium nitrate, magnesium sulfate, potassium chloride, sodium bicarbonate, sodium chloride and sodium phosphate dibasic (anhydrous). DME contains inorganic salts, amino acids, vitamins and other materials. The inorganic salts include calcium chloride, ferric nitrite, magnesium sulfate (anhydrous), potassium chloride, sodium bicarbonate, sodium chloride and sodium phosphate monobasic (anhydrous).

FIG. 40 is a set of photos showing salt crystals in basement membrane. FIG. 40A shows salt crystals after drying when no dialysis is used. FIG. 40B shows salt crystals after drying when a single dialysis step is used. FIG. 40C shows a lack of salt crystals after drying when two dialysis steps are used.

FIG. 41 includes photos showing the effect of pre-dialyzed and post-dialyzed basement membrane on tissue surrounding implanted sensors.

Example 13—Dialysis of Basement Membrane

A commercial basement membrane was obtained in which the concentration of basement membrane was 10-20 mg basement membrane/ml of media. The mouse basement membrane used in these studies was from Becton Dickenson Bioscience, sold under the name Matrigel®. The tissue culture media which contained the basement membrane when it was purchased was DME or RPMI1640 from Sigma Chemical Co. According to Sigma Chemical Co., these media typically contain greater than 10-15 mg of salts, glucose, and amino acids (in total) per ml of media.

The basement membrane was dialyzed using the procedures and equipment of Pierce (www.piercenet.com). 2 ml of basement membrane was put in a small container that had a 2000 dalton molecular weight cut-off membrane as the bottom wall. This container was placed at the top of a tube containing 48 ml of water in order that the membrane was immersed in the water.

The material was dialyzed a first time using the 2000 dalton molecular weight cut off dialysis membrane for 24 hr. (1/25 dilution) at 4 Deg. C. in water on a platform-type rotator. A portion of the material then underwent a second dialysis using a 2000 dalton molecular weight cut off dialysis membrane for 24 hr. (1/25 dilution) at 4 Deg. C., using a tube of water and the platform-type rotator. A portion of the material then underwent a final dialysis with the dilution of BM of 1/625. As a result, the media (not including the basement membrane) contained 0.016 to 0.024 mg/ml salts, glucose and amino acids.

Three separate 20-microliter samples of basement membrane (in the media) from the experiment described in the previous paragraph were placed on microscopic slides and dried for 24 hours at 37 Deg. C. The first sample was not subjected to any dialysis. The second sample was subjected to the first dialysis only, and the third sample was subjected to the both the first dialysis and the second dialysis. After drying at room temperature, the samples were examined to determine the presence and size of any salt crystals. The results are shown in FIG. 40. As can be seen in the photographs, a large crystalline conglomerate having a diameter of about 20 mm was present in the first sample that had not undergone dialysis, and the crystal diameters were about 2-3 mm. The second sample had medium-sized salt crystal conglomerates. The third sample had no easily visible salt crystals.

As shown in the photographs, the dialysis removed most of the salt from the media. It can be assumed that the other materials falling below the 2000 dalton molecular weight cut-off also were removed.

Example 14—Coating Sensor with Modified Basement Membrane Preparation

A sample of the modified basement membrane preparation that had undergone the two-stage dilution described above was coated on a glucose sensor by depositing the basement membrane on a sensor dropwise, three drops at a time and drying the coating at room temperature. This procedure was repeated until a total of about 100 microliters of basement membrane had been deposited. A mesh made of polyester was separately coated. A collar for a cannula also was formed from the modified basement membrane preparation.

After the coated sensor was dried for 24 hours, it was placed in the subcutaneous tissue of a mouse. After 14 days, a histologic evaluation of the implantation site was conducted by euthanizing the mouse, removing the tissue, processing the tissue, and evaluating it microscopically. As is shown in FIGS. 41C and 41D, there was minimal, if any, injury or inflammation of the tissue, with little, if any, degradation of the basement membrane. Because of the dialysis, it was not necessary to remove salts, glucose, and amino acids at the time of rehydration.

A control experiment was conducted using a sample of the basement membrane (in media—as sold commercially) that did not undergo any dialysis. A glucose sensor of the same type used above was coated in the manner described above. After the sensor was dried for 24 hours, it was placed in the subcutaneous tissue of a mouse. After 14 days, a histologic evaluation of the implantation site was conducted by euthanizing the mouse, removing the tissue, processing the tissue, and evaluating it microscopically. As is shown in FIGS. 41A and 41B, there was substantial injury and inflammation of the tissue, as well as extensive degradation of the basement membrane. Degradation of the basement membrane was caused by proteases and hydrolases from white blood cells that dissolve and degrade matrices including basement membrane.

Example 15

The procedures of Examples 13 and 14 were generally repeated using commercially available Trevigen basement membrane called Cultrex® Basement Membrane Extract, Type 2, PathClear® (purified from Engelbreth-Holm-Swarm (EHS) tumor). The results of salt crystal size without dialysis, after 1 stage of dialysis and after 2 stages of dialysis were similar to the results of Example 13. Examination of the tissue after 14 days showed the same effects as with the Matrigel®, i.e. tissue inflammation and basement membrane degradation when pre-dialyzed basement membrane was used, and minimal tissue inflammation and basement membrane degradation when dialyzed basement membrane was used.

Example 16

In an effort to even further increase the stability and effectiveness of the basement membrane coatings, the coatings were cross-linked utilizing glutaraldehyde as a cross-linking agent. Sensor performance was evaluated for the impact of these crosslinked coatings in vitro and in vivo.

Sensor performance was assessed over a 28-day time period in a murine CGM model and expressed as Mean Absolute Relative Difference (MARD) values. Tissue reactivity of uncrosslinked basement membrane coated sensors, crosslinked basement membrane coated sensors, and uncoated sensors was evaluated at 7, 14, 21 and 28 days post sensor implantation with standard histological techniques. These studies demonstrated that crosslinked basement membrane coatings had no effect on glucose sensor function in vitro. In vivo glucose sensor performance was significantly enhanced when the crosslinked basement membrane coatings were used. Histological evaluations of sensors coated with crosslinked basement membrane demonstrated significantly less tissue reactivity when compared to control sensors.

Basement Membrane Preparations

Basement Membrane Extract (Cultrex, Type 2) Clearpath, was purchased from Trevigen, Inc. (Gaithersburg, Md.). Cultrex Basement Membrane Extract (referred to as Cultrex, Cultrex basement membrane or Cultrex BM) is a soluble form of basement membrane purified from murine Engelbreth-Holm-Swarm tumor. The basement membrane is stored in Dulbecco's Modified Eagle's medium without phenol red, with 10-ug/ml gentamicin sulfate, at a storage and working concentration of approximately 15 mg protein/ml (Table 1). Generally the Cultrex preparations are kept frozen at −80 C, thawed in ice water, and maintained on ice for general use.

Dialysis of Basement Membrane Preparations

To eliminate salts, vitamins, amino acids and glucose present in the basement membrane preparations, the basement membrane was dialyzed against sterile deionized water with 3 changes of water using Thermo Scientific Slide-A-Lyzer Mini Dialysis devices. More specifically, 2 ml of Cultrex was dialyzed against 48 ml of water/exchange, for a total of 3 dialysis exchanges.

Coating of Glucose Sensors with Cross-Linked Basement Membrane

The modified Abbott Navigator glucose sensors which are Transdermal Amperometric sensors used in the in vitro and in vivo studies were obtained from Abbott Diabetes Care [Alameda, Calif.]. Sensors were sterilized by exposure to UV light overnight prior to administering the sensor coating. Aseptic techniques were utilized during the coating process and prior to implantation. To coat the glucose sensors with cross-linked basement membrane, the glucose sensors were mounted (FIG. 47A) and placed on a sterile polytetrafluoroethylene (PTFE) liner (FIG. 47B). Specifically, 50 uL of dialyzed Cultrex (15 mg protein/ml) was applied on one side of each sensor (FIG. 47C) and the sensors were placed in a 37° C. incubator for 2 hours, resulting in drying of the basement membrane (FIG. 47D). The glucose sensors were then turned over and an additional 50 uL of dialyzed Cultrex was applied on the opposite side of the sensors (FIG. 47E) prior to placing them in 37° C. incubator for 2 hours, resulting in drying (FIG. 47F). The resulting coated sensors were lifted off of the PTFE liner (FIG. 47G) and briefly dipped into sterile pyrogen-free water to shape the coating around the sensors (FIG. 47H) followed by drying at 37 C (FIG. 11). Next the dry coated sensor was place in a 0.2-0.4% glutaraldehyde solution (FIG. 47J) for 5 minutes followed by at least 1 hr of dialysis in sterile, pyrogen-free water, followed by drying at 37° C. for at least 2 hours (FIG. 47L) Other biocompatible solutions, such as alcohol or buffers, can be used in place of pyrogen-free water. FIG. 47K demonstrates that even after being cross-linked, the Cultrex basement membrane preparations are still gelatinous and full of liquid (i.e. they remain bio-hydrogels). FIG. 47L demonstrates that when the gluteraldehyde cross-linked Cultrex BM it forms a thin layer of dry BM which enhances both its shelf-life, as well as the ease of inserting the coated sensor into living tissue. The resulting cross-linked Cultrex was designed as X-Cultrex. This coating technique allowed for a simple and consistent coating process. The crosslinked coated glucose sensors and the control sensors, some of which were uncoated and some of which were coated with uncrosslinked basement membrane, were stored dehydrated in a tissue culture hood until in vitro testing or implantation in mice.

In Vitro Glucose Sensor Testing

In order to determine if X-Cultrex coating negatively impacted sensor performance, sensor sensitivity of uncoated glucose sensors (controls), were evaluated pre and post X-Cultrex coating in vitro. Sensor sensitivity was characterized in tissue culture medium with an initial glucose concentration of 50 mg/dL at 200 mV. Background current was allowed to stabilize for about 15 minutes before sensors were subjected to increased glucose concentrations in the culture medium. Sensors were then rinsed in sterile water and left in a tissue culture hood to dry. After the sensors completely dried they were coated with X-Cultrex as described above. Sensors were then retested in vitro using the same protocol as described above. Sensor sensitivity for both pre and post X-Cultrex coatings was determined as described below (2, 5).

Glucose Sensor Implantation and CGM

Once it was established that the sensor coating did not negatively impact sensor performance in vitro, the performance of the X-Cultrex coated sensors versus uncoated sensors was evaluated in a CGM mouse model. Coated and un-coated sensors were implanted in CD-1 mice (Jackson Laboratory, Bar Harbor, Me.) and continuous glucose monitoring (CGM) was undertaken for a period up to 28 days. Blood glucose reference measurements from the tail vein were obtained systematically over the 28-day implantation period using Bayer Contour blood glucose monitors. The Institutional Animal Care and Use Committee of the University of Connecticut Health Center (Farmington, Conn.) approved the murine studies. The sensors were not recalibrated such that their readings represent raw sensor output in nano-Amperes (nA).

Continuous Glucose Monitoring Data Analysis

Reference blood measurements were used to calculate the mean absolute relative difference (MARD) over a four-week experiment for the two groups of mice with and without basement membrane coated sensors. Equations (1)-(3) describe the MARD calculation in detail. Sensitivity (S; mg/dl/nA) is calculated for each mouse based on the reference blood glucose and the sensor output (I; nA) measurements in an initial reference stage of the experiment, i.e., k in Equation (2) is approximately 5, for the first initial five measurements across two days.

$$MARD(\text{mean}) = \left(\left(\sum_i^n \frac{|CGM_i - BG_i|}{BG_i}\right)/n\right) \times 100\%, \quad (1)$$

$$\text{Sensitivity}(S) = \left(\left(\sum_i^k (BG_i/I_i)\right)/K\right), \quad (2)$$

$$CGM_i = S \times I_i. \quad (3)$$

Histopathological Analysis of Tissue Reactions at Glucose Sensor Implantation Sites In order to evaluate tissue responses to non-Cultrex coated, Cultrex and X-Cultrex coated glucose sensors tissue samples were obtained from mice concluding CGM evaluation. Mice were euthanized and the full thickness of the skin and sensors were removed end bloc in approximately 3×3 $cm^2$ sections and immediately placed in tissue fixative. Tissues were fixed in formalin for 24 to 48 hours followed by processing, embedding in paraffin, and sectioning. The resulting 5-μm sections were then stained using standard protocols for hematoxylin and eosin stain and Masson Trichrome (fibrosis). Histopathological evaluation of tissue reactions at sites of sensor implantation was performed on mouse specimens obtained at 1-28 days post-sensor implantation. The tissue section slides were viewed and assessed by a blinded experienced histopathologist (DLK) using a modified histologic scale (2, 4, 5, 7). Histologic parameters included inflammatory response, foreign body reaction, fibrotic response, collagen organization, and neovascularization. After an initial review of all slides to gain a baseline measure of histologic parameters, each sample was re-evaluated and scored against each other to obtain a semi-quantitative measure of tissue responses to the implanted sensors. For the inflammatory response, the degree of infiltration of chronic inflammatory cells, principally lymphocytes and macrophages, surrounding the sensor were noted. Foreign body reaction was determined by the relative quantity of foreign body giant cells (FBGC) surrounding each sensor or adjoining tissue of sensor. Fibrotic change was a function of relative abundance of new collagen deposition at sites of sensor implantation, while collagen organization was determined by factors such as connective tissue density (loose versus dense) and arrangement of collagen bundles (parallel versus haphazard pattern). Neovascularization was a reflection of the number of new blood vessels per high power field (7).

Immunohistochemical Staining of Macrophages Using Anti-Mouse F4/80 Antibodies

To confirm the observed presence of macrophages in tissue sections, a mouse macrophage specific antibody designated anti-mouse F4/80 was utilized. Anti-mouse F4/80 (@F4/80) (Invitrogen Catalog # A14800) was validated using mouse spleen tissue and standard immunohistochemical (IHC) techniques.

Statistical Analysis

The mean MARD values for each group, together or separated by week, were evaluated statistically, including tests to determine if the group MARD values were normally distributed. In cases where the mean MARD values were non-normal in distribution, Mann-Whitney U tests were then conducted to determine the statistical differences between the two groups of average mean MARD values, as non-parametric equivalents to student t-tests. Microsoft Excel for Mac 2011 (version 14.1.4) and IBM SPSS Statistics 20 (release 20.0.0) were the software packages used for the calculations/graphing and statistical analyses, respectively.

Results

Impact of Cultrex Coatings on Glucose Sensor Function In Vitro and In Vivo

Previous experiments have demonstrated that glucose sensors coated with non-cross-linked Cultrex did not affect sensor function in vitro (1). Previous experiments also have demonstrated that sensors coated with Cultrex showed significantly less tissue reaction at sites of sensor implantation. These Cultrex coated sensors also showed an increased performance compared to uncoated sensors. The Cultrex sensor coating, however, began to degrade by day 21-post sensor implantation and sensor induced sensor tissue reactions were seen. It is believed that the loss of the Cultrex coatings eliminated the protective sensor coating resulting in the exposure of the underlying sensor surface. In an effort to increase the longevity of the Cultrex sensor coating, cross-linked Cultrex was used to first determine whether cross-linked Cultrex coating compromised sensor function in vitro (FIG. 47). The impact of varying coatings of Cultrex on glucose sensor performance in vitro was determined, as is described above. Sensor sensitivity remained unchanged before and after the Cultrex coating within the range of 0 to 2 mg Cultrex/sensor, and was determined to be 45.9±4.8 mg/(dL*nA) and 48.6±5.1 mg/(dL*nA), respectively. For the cross-linked Cultrex (X-Cultrex), sensor sensitivity remained very close before and after the X-Cultrex coating within the range of 0 to 3 mg X-Cultrex/sensor, and was determined to be 37.9±3.2 mg/(dL*nA) and 41.3±2.2 mg/(dL*nA), respectively.

Figure 48:
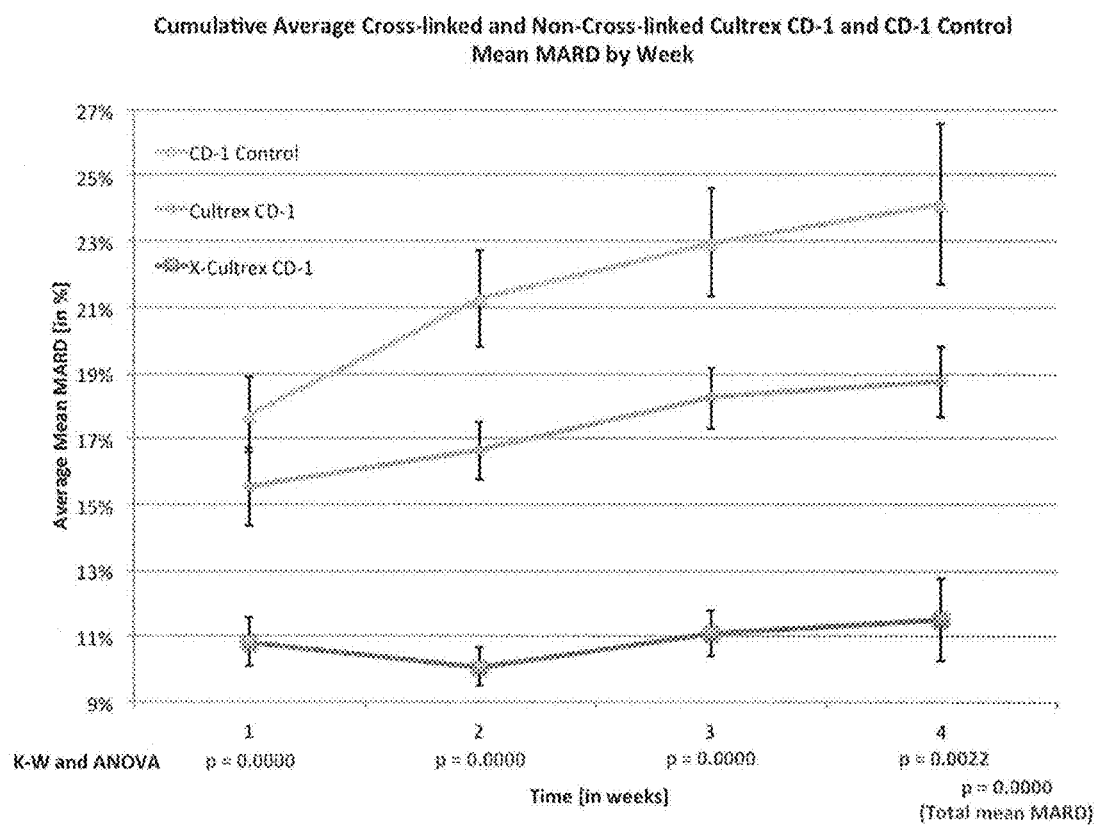
FIG. 48 is a graph showing average mean MARD over time for sensors coated with crosslinked basement membrane and sensors coated with basement membrane that is not crosslinked.

Once it had been demonstrated that the cross-linking of Cultrex coatings did not negatively affect sensor performance in vitro, the effect was determined of X-Cultrex coatings on sensor performance in vivo for a period of up to 28 days. These in vivo studies were performed utilizing an established murine model of CGM. For these studies mean absolute relative difference (MARD) values of non-cross-linked Cultrex and X-Cultrex coated sensors were used, as well as uncoated, control sensors in CD-1 mice as a measure of sensor performance and error of the CGM sensors over time; the lower the MARD values, the lower the error, the better the performance. It is important to note that no sensor recalibration occurred for these studies. Thus, MARD values used in these studies are derived from raw sensor output. As illustrated in FIG. 48, the cross-linking of the Cultrex on the sensor resulted in a significant improvement of sensor functionality when compared to uncoated or non-cross-linked Cultrex coated sensors for the entire 28 day in vivo evaluation (FIG. 48). Statistical comparisons of the sensor performance during the entire four week, 28 day post-implantation experimental time course, showed that the X-Cultrex had dramatically better MARD values compared to non-coated control and Cultrex coated sensors (FIG. 48, and FIG. 52). By the fourth week, the total average MARD value for the CD-1 mice with X-Cultrex coated sensors was 10.59% in a group of 26 mice, Cultrex coated sensors was 16.7% in a group of 34 mice, as compared to the CD-1 control mice with 20.52% on average, in a group of 39 mice (FIG. 53). These sample sizes are relatively large for such investigations. A calculation of standard deviation of the MARD values for these groups of mice indicates that the CD-1 controls present a larger standard deviation of 6.58%, while the Cultrex coated CD-1 MARD values present a smaller standard deviation of 6.14%, and the X-Cultrex coated sensors with a very low standard deviation of 2.94% (FIG. 53).

Figure 49:
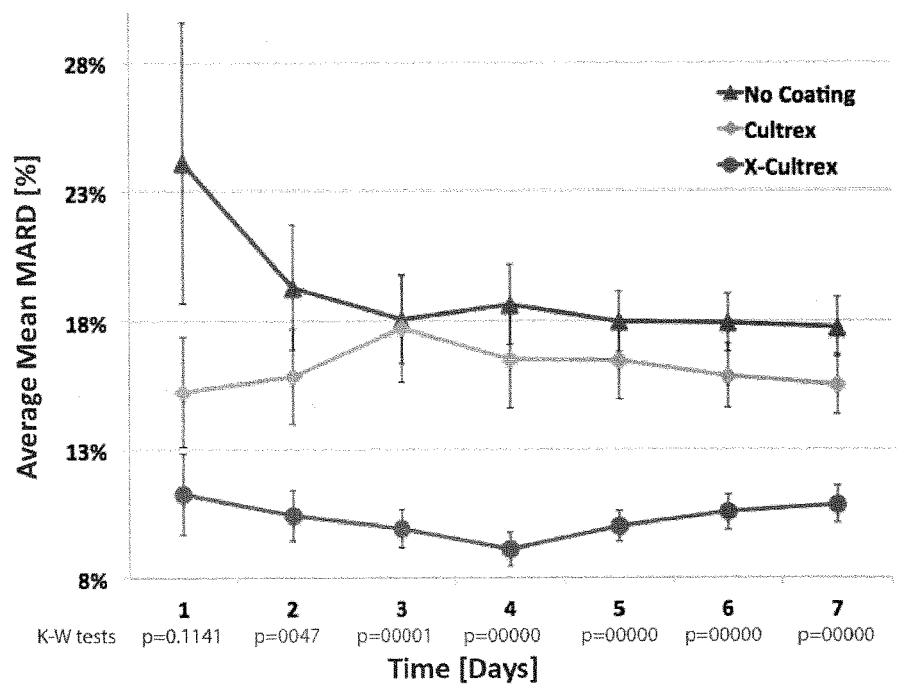
FIG. 49 is a graph showing average mean MARD over time for sensors coated with crosslinked basement membrane, sensors coated with basement membrane that is not crosslinked, and uncoated control sensors during the first 7 days post sensor implantation in a mouse model of continuous glucose monitoring (CGM).

It is noted that the overall performance of the X-Cultrex coated sensors surpassed sensor performance of Cultrex and uncoated sensors within the first 7 days of the study (FIG. 49). This is important since the high accuracy underscores the enhancing effect of X-Cultrex even within the first 7 days post sensor implantation. The sensor performance in day 1 was significantly improved with the crosslinked basement membrane when compared to uncoated sensors and sensors coated with non-crosslinked basement membrane of the same type.

As illustrated in FIG. 48, a trend analysis of the MARD values of the Cultrex and X-Cultrex coated sensors in CD-1 mice and their CD-1 control mice, over the course of the four (4) week experiment, shows a significant improvement in sensor performance, i.e. lower MARD values, for the X-Cultrex coated sensors throughout the entire experiment. The difference in MARD values among all three groups was statistically evaluated by ANOVA tests and its non-parametric equivalent, Kruskal-Wallis (K-W) tests. The differences in MARD values between any two groups were statistically evaluated by student t-tests and its non-parametric equivalent, Mann-Whitney U-tests. The MARD values for weeks 1 and 2, required the non-parametric Mann-Whitney U-tests, while week 3 and the total mean MARD values were normally distributed, hence evaluated with student t-tests. Total mean MARD values are MARD values not separated by week, i.e. each sensor/mouse has one average or mean MARD value for the entire or total experiment. The MARD values for week 4 generally required the non-parametric statistical tests, because the Cultrex coated CD-1 mice MARD values for week 4 were not normally distributed. However, both the X-Cultrex coated and control CD-1 MARD values for week 4 were normally distributed, and the statistical comparison of those two groups were evaluated with a student t-test. A statistical comparison among the three groups by total mean MARD revealed that they were significantly different, p=0.0000. Statistical comparisons between each pairing of the three groups by total mean MARD revealed that all the groups were significantly different from each other: Cultrex coated and control CD-1, p=0.0114; Cultrex and X-Cultrex coated CD-1, p=0.0000; X-Cultrex coated and control CD-1, p=0.0000. The statistical comparisons among the three groups by week demonstrated that there were significant differences during the entire four week experimental time course, i.e. p=0.0000, 0.0000, 0.0000, 0.0022, for weeks 1 through 4, respectively. The effects of X-Cultrex in improving sensor performance, even better than simply Cultrex coating, were clear in the first week (FIG. 3), since the statistical comparison between the Cultrex CD-1 and control CD-1 mice demonstrated that there was only a trending significant difference, i.e. p=0.0768 in week 1, whereas there was strong significant difference between X-Cultrex CD-1 and control CD-1 mice in week 1, p=0.0000. As expected the uncoated sensors displayed a decrease in sensor performance beyond 7-day implantation, and a rise in MARD values, as per the trend analysis graph. However, the X-Cultrex coated sensors continued to display significantly better performance over the entire same 28 days of the study (FIG. 48), and Cultrex coated sensors displayed a significantly better performance weeks 2 and 3. Particularly in the second week, a Mann-Whitney U-test, revealed a statistically significant difference between the MARD values for Cultrex coated sensors in CD-1 mice when compared to the uncoated sensors implanted in CD-1 control mice (p=0.0058), and the MARD values for X-Cultrex in week 2 even decreased relative to week 1, (p=0.0000). In the third week, a t-test revealed that the Cultrex coated sensors showed statistically significant better performance compared to CD-1 controls (p=0.0303), while X-Cultrex coated sensors continued to show very strong performance compared to CD-1 controls (p=0.0000). By the fourth week, although the Cultrex coated sensors did appear to be out performing the uncoated sensors, the MARD between them was not statistically different (p=0.1774). However X-Cultrex coated sensors again continued to show very strong performance compared to CD-1 controls (p=0.0004).

Impact of Basement Membrane Coatings on Sensor Induced Tissue Reactions at Sites of Glucose Sensor Implantations Based on the functional data described above, it is evident that the dramatic increase in the sensor performance of the X-Cultrex coated sensor was a direct result of the diminished sensor induced tissue reactions in the X-Cultrex coated sensors, i.e. increased biocompatibility and stability of the X-Cultrex coatings. Previous studies in our laboratories demonstrated that non-cross-linked Cultrex BM preparations (gel form) can be implanted in mouse subcutaneous tissue for extended periods of time without inducing significant tissue reactions (1). Unfortunately the non-cross-linked Cultrex began degrading around 14-21 days post sensor implantation resulting in increased tissue reactions at the sensor implantation site (1). As such, the biocompatibility of the non-cross-linked Cultrex in vivo suggested that it could be a strong candidate for biocompatibility coating for implanted devices, such as glucose sensors, if it was more stable and remained highly biocompatible.

To investigate whether cross-linked Cultrex enhances coating stability, while retaining biocompatibilty, the tissue reactions associated with non-coated, non-cross linked Cultrex and X-Cultrex coated sensors implanted in mouse subcutaneous tissue were evaluated over a 28 day time period (FIG. 50). As expected, from the previous studies during the first 14 days post sensor implantation, the non-cross-linked Cultrex appeared intact on the sensor surface and demonstrated significantly less tissue reaction at the implantation site (FIGS. 50, E and F). However by 21 and 28 days there was significant loss of the Cultrex coating on the sensor surface and early indication of tissue reactions being induced at the sensor implantation site (FIGS. 50, G and H). When tissue reactions induced by X-Cultrex coated sensors, X-Cultrex demonstrated that X-Cultrex was very stable and biocompatible for the tested time period up to 28 days post sensor implantation (see FIG. 50, I-T v) when compared the non-cross linked Cultrex (FIG. 50, *e-h*) as well as uncoated sensors (FIG. 50, *a-d*). To extend these observations the presence of macrophages at sensor implantation sites was evaluated. Macrophages were selected because of their clear role in biofouling of glucose sensors in vivo. For these studies immunohistochemical staining of tissue section using mouse macrophage specific anti-F4/80 antibodies. As can be seen in FIG. 51, non-Cultrex coated sensors triggered significant macrophage accumulation at the uncoated sensor implantation site (FIGS. 51 *c* and *d*). Alternatively, coating the sensors with Cultrex (FIGS. 51 *e* and *t*) or X-Cultrex (FIGS. 51 *g* and *h*) resulted in a dramatic decrease in macrophage accumulation at the coated sensor implantation sites. In conclusion, it is important to underscore the fact that these histologic studies are consistent with the sensor function study present in FIGS. 48 and 49, and support our hypothesis supporting the uses of X-Cultrex as a sensor coating in vivo.

Discussion

It is now generally accepted that glucose sensor's frequent unreliable performance is often the result of the tissue reaction induced in part by the sensor implant and in part by the initial implantation itself. Over the years various efforts have been examined with the common goal to foster device/tissue integration with minimal to no tissue reactions. These efforts include controlling the tissue reaction at sites of device location with the release of steroids (8-12) and/or growth factors. Recent efforts in our laboratory demonstrated that basement membrane (BM) based bio-hydrogels as coatings (designated as Cultrex) for glucose sensors enhance sensor biocompatibility and function in vivo. Specifically, these studies showed that Cultrex based BM sensor coatings accomplished the dual goals of 1) decreased tissue reactivity at site of glucose sensor implantation in vivo as well as 2) extended device performance in a CGM murine model. Nonetheless these accomplishments were short lived due to the degradation of the bio-hydrogel. Upon the initiation of the bio-hydrogel degradation due to the natural degradation processes related to extracellular turnover a subsequent decline in sensor performance was seen around three weeks post sensor implantation. It is believed that this degradation process exposes the original sensor surface and induces the commonly observed foreign body tissue reaction. As such, the bio-hydrogel was only able to delay the tissue reaction at the sensor implantation site. It appeared that this delay is dependent on the degradation rate of the outer sensor Cultrex coating.

In response to these observations the present studies were undertaken to investigate whether chemical crosslinking of the Cultrex would increase the stability and biocompatibility of Cultrex based biohydrogels in vivo, and thereby increase the function and lifespan of sensors and CGM. Previous studies using cross-linked collagen coatings, demonstrated marginal effects on sensor function in vivo. This lack of enhanced sensor function was likely due to tissue reactions that were induced by the cross-linked collagens, i.e. inflammation and fibrosis. These tissue reactions were likely the result of excessive crosslinking of the collagen by gluteraldehyde. Due to issues of gluteraldehyde induced tissue reactions, our strategy was to utilize low concentrations of gluteraldehyde (0.2-0.3%) and only briefly expose BM (i.e. Cultrex) to the gluteraldehyde (i.e. 5 minutes) fixative. Upon fixation the sensor/BM gluteraldehyde coating was then followed by exposure to pyrogen free water to minimize any tissue induced tissue reactions resulting from the fixative. In order to minimize effects of the fixative to the tissue, Cultrex BM was cross-linked upon the completion of post sensor Cultrex BM coating and drying. In vivo murine CGM studies demonstrated that X-Cultrex coated sensors experienced overall very strong performance compared to CD-1 controls and Cultrex coating only. This strong performance for X-Cultrex coated sensors was seen beyond the third week of study. As it relates to Cultrex coated sensors, performance in week three and four was increased when compared to control (e.g. no Cultrex coating) (FIG. 48). It is believed that the increased MARD values seen particularly in weeks three and four post sensor implantation of the Cultrex coated CD-1 mice was likely the result of the degradation of the Cultrex coating, a result of the normal tissue remodeling, which does not appear or only slightly occur in the X-Cultrex coated sensors (FIG. 48). This hypothesis was supported by the histologic studies (FIG. 50). This degradation ultimately exposes the underlying glucose sensor, triggering the regular tissue reactions including inflammation and tissue remodeling leading to further degradation of the Cultrex coating of the sensors. The use of glutaraldehyde to cross-link Cultrex appears to prevent appreciable degradation and subsequently appears to prevent tissue remodeling and inflammatory processes. Interestingly, X-Cultrex outperformed Cultrex coated sensors alone and control sensors also during the first week post sensor implantation (FIG. 49). It is believed that this is due in part to the consistence of the X-Cultrex coating to stay in place during the implantation process. It is believed that Cultrex coating sensors experience a higher rate of variability during the implantation process due to dislocating the Cultrex coating. Nevertheless, these studies emphasize that a biocompatible hydrogel such as Cultrex can facilitate an increased long-term sensor performance.

Natural bio-hydrogels present numerous binding sites for specific proteins such as growth factors and cytokines within their molecular structures (15-24). These binding sites serve a critical role in regulation of cell and tissue responses to injury including inflammation, repair and regeneration.

Conclusion—

This example demonstrated that the sensors coated with crosslinked basement membrane dramatically enhanced glucose sensor function and lifespan in vivo, and induced virtually no tissue reactions in a 28 day time period, when compared to non-cross-linked control coatings, and sensors without any coatings. These studies show that crosslinked matrix coatings such as biohydrogels can be used biocompatible coatings for implantable devices, such as glucose sensors, and other implants described above. Crosslinking protocols aid in the enhancement of biohydrogel stability and biocompatibility in vitro and in vivo without compromising loss of biocompatibility, i.e. X-Cultrex BM coatings. The data included herein suggest that cross-linked BM based bio-hydorgels represent a completely new generation of biocompatible coatings for implantable devices such as glucose sensor and a vast variety of other implantable devices.

Prophetic Example 17

The procedures of Example 16 are repeated with the exception that the glutaraldehyde is added to the basement membrane before drying, i.e. at the stage of FIGS. 47C, 47E and/or 47H. The glutaraldehyde can be added dropwise to the wet basement membraned that is already on the implantable device, or can be pre-mixed with the basement membrane before the device is coated with the basement membrane. Excess glutaraldehyde optionally can be removed by a suitable technique such as placement in pyrogen-free, sterile water or another liquid, or by the addition of glutaraldehyde reactive agents. The resulting crosslinked coating is similar to that obtained in Example 16. This technique provides an opportunity for more control of the final concentration of glutaraldehyde in the coating and may simplify a large-scale production.

Prophetic Example 18

The procedures of Example 16 are repeated with the exception that the basement membrane is crosslinked with other crosslinking agents. It is expected that reactive molecules would be cross-linked by variety of crosslinking agents, thereby changing the primary, secondary and tertiary structure of the cross-linked basement membrane by changed the crosslinking agent. In this way the functionality and biocompatibility of the coating can be altered.

Prophetic Example 19

The procedures of Example 16 are repeated with the exception that the sensor is replaced by a surgical mesh. It is expected that these meshes increase in their biocompatibility.

Prophetic Example 20

The procedures of Example 16 are repeated with the exception that the sensor is replaced by a cannula and the basement membrane is applied to the implantable portion of the cannula. It is expected that this embodiment will result is a lower degree of tissue reaction with more effective regulation of blood glucose.

Prophetic Example 21

The procedures of Example 16 are repeated with the exception that the sensor is replaced by a collar for an implantable device and the basement membrane is applied to the portion of the collar configured to be adjacent to, or inserted in, tissue. It is expected that the function, accuracy and lifespan of the sensor will be increased because of a decreased likelihood, rate or degree of infection as a result of infection caused by the transdermal device.

Example 22

To determine the stability and reactivity of X-Cultrex coated sensors in mice at time points beyond 28 days, sensors coated with cross-linked Cultrex (0.3% glutaraldehyde) were implanted subcutaneously in mice and removed at 2 months post implantation. When the implantation site was evaluated in situ significant neovascularization was seen surrounding the X-Cultrex coated sensor, specifically at the tissue X-Cultrex interface (see FIG. 54). Arrows indicate the presence of new blood vessels in tissue surrounding the X-Cultrex coated sensor. This study demonstrates that increased neovascularization surround the X-cultrex coated sensor occurs at 2 months post sensor implantation. This increased neovascularization would likely promote sensor function by providing a blood vasculature close the sensor. The presence of this vasculature close to the sensor would give a more accurate real time evaluation of blood glucose in the mice.

It is appreciated that the above-disclosed and other features and functions, or alternatives thereof, may be desirably combined into many other different systems or applications. Various presently unforeseen or unanticipated alternatives, modifications, variations, or improvements therein may be subsequently made by those skilled in the art, which are also intended to be encompassed by the following claims. Unless otherwise specifically defined in the claims, steps and components of the examples are not intended as limitations to any particular order, position, size, shape or material.

What is claimed is:

1. A surgical mesh coated with a crosslinked basement membrane preparation comprising Type IV collagen and laminin, wherein the crosslinked basement membrane preparation contains no more than 0.024 mg/ml total concentration of glucose, amino acids and salts having a molecular weight of 2000 daltons or less.

2. The surgical mesh of claim 1, wherein the crosslinked basement membrane preparation is dehydrated after being in the form of a gel at room temperature.

3. The surgical mesh of claim 1, wherein the crosslinked basement membrane preparation is dehydrated at a temperature in the range of 1-4° C. after being placed on the mesh when the basement membrane is in the form of a liquid.

4. The surgical mesh of claim 1, wherein the crosslinked basement membrane preparation is dehydrated at a temperature in the range of 10-30° C.

5. The surgical mesh of claim 1, wherein the crosslinked basement membrane preparation is applied in multiple layers, and the basement membrane preparation is dehydrated after application of each layer.

6. The surgical mesh of claim 1, wherein the mesh also comprises layers of other extracellular matrices formed thereon.

7. The surgical mesh of claim 1, wherein the crosslinked basement membrane preparation contains at least one of cells and factors, the factors being at least one member selected from the group consisting of angiogenic factors, drugs, antimicrobials, cytokines, growth factors and anti-inflammatory factors.

8. A kit comprising the surgical mesh of claim 1 enclosed in sterile packaging.

9. The surgical mesh of claim 5, wherein the crosslinked basement membrane preparation contains at least one of cells and factors, the factors being at least one member selected from the group consisting of angiogenic factors, drugs, antimicrobials, cytokines, growth factors and anti-inflammatory factors.

10. The surgical mesh of claim 1, wherein the basement membrane preparation contains a factor, including at least one of a vascular endothelial growth factor, a hepatocyte growth factor and a fibroblast growth factor.

11. A surgical mesh coated with a basement membrane preparation comprising Type IV collagen and laminin, said basement membrane preparation is crosslinked with a dialdehyde, wherein said crosslinked basement membrane preparation contains no more than 0.024 mg/ml total concentration of glucose, amino acids and salts having a molecular weight of 2000 daltons or less.

12. The surgical mesh of claim 11, wherein the basement membrane preparation is applied in multiple layers, and the basement membrane preparation is dehydrated after application of each layer.

13. The surgical mesh of claim 11, wherein the surgical mesh also comprises layers of other extracellular matrices formed thereon.

14. The surgical mesh of claim 11, wherein the crosslinked basement membrane preparation contains at least one of cells and factors, the factors being at least one member selected from the group consisting of angiogenic factors, drugs, antimicrobials, cytokines, growth factors and anti-inflammatory factors.

15. The surgical mesh of claim 14, wherein the cells and/or factors are bonded to the basement membrane preparation.

16. The surgical mesh of claim 10, wherein the basement membrane is crosslinked using a di-aldehyde.

17. The surgical mesh of claim 1, wherein the basement membrane in the preparation comprises cell culture derived basement membrane.

18. The surgical mesh of claim 11, wherein the basement membrane in the preparation comprises cell culture derived basement membrane.

* * * * *